United States Patent
Barker et al.

(10) Patent No.: US 11,541,101 B1
(45) Date of Patent: Jan. 3, 2023

(54) LEMD3 ANTAGONIZES TGF-BETA-DRIVEN SMAD2/3 TRANSCRIPTION IN A STIFFNESS-DEPENDENT FASHION IN BOTH THE NUCLEUS AND CYTOSOL

(71) Applicants: University of Virginia Patent Foundation, Charlottesville, VA (US); Emory University, Atlanta, GA (US)

(72) Inventors: Thomas H. Barker, Crozet, VA (US); Leandro Moretti, Charlottesville, VA (US); Dwight M. Chambers, Atlanta, GA (US)

(73) Assignees: University of Virginia Patent Foundation, Charlottesville, VA (US); Emory University, Atlanta, GA (US)

( * ) Notice: Subject to any disclaimer, the term of this patent is extended or adjusted under 35 U.S.C. 154(b) by 0 days.

(21) Appl. No.: 16/597,712

(22) Filed: Oct. 9, 2019

Related U.S. Application Data

(60) Provisional application No. 62/743,049, filed on Oct. 9, 2018.

(51) Int. Cl.
| | | |
|---|---|---|
| C07H 21/02 | (2006.01) |
| A61K 38/17 | (2006.01) |
| A61K 48/00 | (2006.01) |
| A61P 17/00 | (2006.01) |
| A61K 31/713 | (2006.01) |
| C12N 15/113 | (2010.01) |

(52) U.S. Cl.
CPC ........ *A61K 38/1709* (2013.01); *A61K 31/713* (2013.01); *A61K 48/0066* (2013.01); *A61P 17/00* (2018.01); *C12N 15/113* (2013.01); *C12N 2310/14* (2013.01); *C12N 2320/31* (2013.01)

(58) Field of Classification Search
CPC .............. C12N 15/113; C12N 2310/14; C12N 15/1062; C12Q 2525/203
See application file for complete search history.

(56) References Cited

U.S. PATENT DOCUMENTS

| 4,554,101 A | 11/1985 | Hopp |
| 2019/0000991 A1 | 1/2019 | Pykett et al. |
| 2019/0008909 A1 | 1/2019 | Nijmeijer et al. |

FOREIGN PATENT DOCUMENTS

| WO | WO 2005/108415 | * | 2/2005 | ......... C12N 15/1062 |
| WO | WO 2007/019107 | | 2/2007 | |
| WO | WO 2007/030652 | | 3/2007 | |
| WO | WO 2007/089798 | | 8/2007 | |
| WO | WO 2008/060374 | | 5/2008 | |

OTHER PUBLICATIONS

Bermeo et al. (Journal of Cellular Biochemistry, 118:4425-4435, 2017, 4425-4435).*
Miyagishi et al. (Nature Biotechnology, 2002, 19, 497-500).*
Abascal et al., "Alternative splicing and co-option of transposable elements: the case of tmpo/lap2alpha and znf451 in mammals." Bioinformatics, vol. 31, pp. 2257-2261 (2015).
Beyer et al., "Switch enhancers interpret TGF-beta and hippo signaling to control cell fate in human embryonic stem cells." Cell Rep., vol. 5, pp. 1611-1624 (2013).
Booth et al., "Acellular normal and fibrotic human lung matrices as a culture system for in vitro investigation." Am. J. Respir. Critical Care Medicine, vol. 186, pp. 866-876 (2012).
Bourgeois et al., "Inhibition of TGF-beta signaling at the nuclear envelope: characterization of interactions between MAN1, Smad2 and Smad3, and ppm1a." Sci. Signal, vol. 6 (2013).
Buhling et al., "Pivotal role of cathepsin k in lung fibrosis." Am. J. Pathol., vol. 164, pp. 2203-2216 (2004).
Caputo et al., "The carboxyl-terminal nucleoplasmic region of MAN1 exhibits a dna binding winged helix domain." J. Biol. Chem., vol. 281, pp. 18208-18215 (2006).
Chou et al., "Empirical Predictions of Protein Conformation." Ann. Rev. Biochem., vol. 47, pp. 251-276 (1978).
Chou et al., "Prediction of protein conformation." Biochemistry, vol. 13, pp. 222-245 (1974).
Chou et al., "Prediction of Beta-Turns." Biophys. J., vol. 26, pp. 367-384 (1979).
Collins et al., "The logic of the 26s proteasome." Cell, vol. 169, pp. 792-806 (2017).
Condorelli et al., "Juvenile elastoma without germline mutations in LEMD3 gene: A case of buschke-ollendorff syndrome?" Pediatr. Dermatol., vol. 34, pp. e345-e346 (2017).
Couto et al., "A novel LEMD3 mutation common to patients with osteopoikilosis with and without melorheostosis." Calcif. Tissue Int., vol. 81, pp. 81-84 (2007).
DePianto et al., "Heterogeneous gene expression signatures correspond to distinct lung pathologies and biomarkers of disease severity in idiopathic pulmonary fibrosis." Thorax, vol. 70, pp. 48-56 (2015).
Du et al., "Pirfenidone ameliorates murine chronic gvhd through inhibition of macrophage infiltration and TGF-beta production." Blood, vol. 129, pp. 2570-2580 (2017).
Garcia-Prieto et al., "Resistance to bleomycin-induced lung fibrosis in mmp-8 deficient mice is mediated by interleukin-10." PLoS One, vol. 5 (2010).
Gardinassi et al., "Blood transcriptional profiling reveals immunological signatures of distinct states of infection of humans with leishmania infantum." PLoS Neglected Trop. Dis., vol. 10, pp. 1-24 (2016).
Gass et al., "Buschke-ollendorff syndrome: a manifestation of a heterozygous nonsense mutation in the LEMD3 gene." J. Am. Acad. Dermatol., vol. 58, pp. S103-S104 (2008).

(Continued)

*Primary Examiner* — Amy H Bowman
(74) *Attorney, Agent, or Firm* — Jenkins, Wilson, Taylor & Hunt

(57) ABSTRACT

Methods and compositions for modulating transforming growth factor-beta (TGFβ) biological activity in a vertebrate subject in need thereof. The methods involve administering to the vertebrate subject an effective amount of a substance capable of modulating activity of LEMD3 in the vertebrate subject to thereby modulate TGFβ biological activity in the vertebrate subject.

8 Claims, 18 Drawing Sheets
(7 of 18 Drawing Sheet(s) Filed in Color)
Specification includes a Sequence Listing.

(56) References Cited

OTHER PUBLICATIONS

Grannas et al., "Crosstalk between hippo and TGFbeta: Subcellular localization of yap/taz/Smad complexes." J. Mol. Biol., vol. 427, pp. 3407-3415 (2015).
Grimm et al., "Titration of AAV-2 particles via a novel capsid ELISA: packaging of genomes can limit production of recombinant AAV-2." Gene Ther., vol. 6(7), pp. 1322-1330 (1999).
Gutierrez et al., "Novel somatic mutation in LEMD3 splice site results in buschke-ollendorff syndrome with polyostotic melorheostosis and osteopoikilosis." Pediatr. Dermatol., vol. 32, pp. e219-e220 (2015).
Harper et al., "Recreation of serine proteases with substituted isocourmarins: discovery of 3,4-dichloroisocoumarin, a new general mechanism based serine protease inhibitor." Biochemistry, vol. 24, pp. 1831-1841 (1985).
Hellemans et al., "Loss-of-function mutations in LEMD3 result in osteopoikilosis, buschke-ollendorff syndrome and melorheostosis." Nat. Genet., vol. 36, pp. 1213-1218 (2004).
Hill, "Nucleocytoplasmic shuttling of Smad proteins." Cell Res., vol. 19, pp. 36-46 (2009).
Holt et al., "Specific localization of nesprin-1-alpha2, the short isoform of nesprin-1 with a kash domain, in developing, fetal and regenerating muscle, using a new monoclonal antibody." BMC Cell Biol., vol. 17, p. 26 (2016).
Jones et al., "Idiopathic pulmonary fibrosis: recent trials and current drug therapy." Respiration, vol. 86, pp. 353-363 (2013).
Kamaraju et al., "Role of rho/rock and p38 map kinase pathways in transforming growth factor-beta-mediated Smad-dependent growth inhibition of human breast carcinoma cells in vivo." J. Biol. Chem., vol. 280, pp. 1024-1036 (2005).
King et al., "A phase 3 trial of pirfenidone in patients with idiopathic pulmonary fibrosis." N. Engl. J. Med., vol. 370, pp. 2083-2092 (2014).
King et al., "Idiopathic pulmonary fibrosis." Lancet, vol. 378(9807), pp. 1949-1961 (2011).
Klingberg et al., "Prestress in extracellular matrix sensitizes latent TGF-beta1 for activation." J. Cell Biol., vol. 207, pp. 283-297 (2014).
Kobayashi et al., "Identification and characterization of gsrp-56, a novel golgi-localization spectrin repeat-containing protein." Exp. Cell Res., vol. 312, pp. 3152-3164 (2006).
Kohlbrenner et al., "Quantification of AAV Particle Titers by Infrared Fluorescence Scanning of Coomassie-Stained Sodium Dodecyl Sulfate-Polyacrylamide Gels." Hum. Gene Ther. Meth., vol. 23(3), pp. 198-203 (2012).
Konde et al., "Structural analysis of the Smad2-MAN1 interaction that regulates transforming growth factor-beta signaling at the inner nuclear membrane." Biochemistry, vol. 49, pp. 8020-8032 (2010).
Korekawa et al., "Buschke-ollendorff syndrome associated with hypertrophic scar formation: a possible role for LEMD3 mutation." Br. J. Dermatol., vol. 166, pp. 900-903 (2012).
Kratzsch et al., "Identification of a novel point mutation in the LEMD3 gene in an infant with buschke-ollendorff syndrome." JAMA Dermatol., vol. 152, pp. 844-845 (2016).
Kristensen et al., "Serological assessment of neutrophil elastase activity on elasin during lung ecm remodeling." BMC Pulm. Med., vol. 15 (2015).
Kyte et al., "A simple method for displaying the hydropathic character of a protein." J. Mol. Biol., vol. 157, pp. 105-132 (1982).
Landrum et al., "Clinvar: public archive of interpretations of clinically relevant variants." Nucleic Acids Res., vol. 44, pp. D862-D868 (2016).
Lin et al., "MAN1, an inner nuclear membrane protein that shares the lem domain with lamina-associated polypeptide 2 and emerin." J. Biological Chemistry, vol. 275, pp. 4840-4847 (2000).
Lin et al., "MAN1, an integral protein of the inner nuclear membrane, binds Smad2 and Smad3 and antagonizes transforming growth factor-beta signaling." Hum. Mol. Genet., vol. 14, pp. 437-445 (2005).
Lin et al., "Ppm1a functions as a Smad phosphatase to terminate TGF-beta signaling." Cell, vol. 125, pp. 915-928 (2006).
Liu et al., "Feedback amplification of fibrosis through matrix stiffening and cox-2 suppression." J. Cell Biol., vol. 190, pp. 693-706 (2010).
Liu et al., "MAN1 and emerin have overlapping function(s) essential for chromosome segregation and cell division in caenorhabditis elegans." Proc. Natl. Acad. Sci. USA, vol. 100, pp. 4598-4603 (2003).
Liu et al., "Mechanosignaling through yap and taz drives fibroblast activation and fibrosis." Am. J. Physiok. Lung Cell Mol. Physiol., vol. 308, pp. L344-L357 (2015).
Lombardi et al., "The interaction between nesprins and sun proteins at the nuclear envelope is critical for force transmission between the nucleus and cytoskeleton." J. Biol. Chem., vol. 286, pp. 26743-26753 (2011).
Mansharamani et al., "Direct binding of nuclear membrane protein MAN1 to emerin in vitro and two modes of binding to barrier-to-autointegration factor." J. Biol. Chem., vol. 280, pp. 13863-13870 (2005).
Massague, "TGFbeta signaling in context." Nat. Rev. Mol. Cell Biol., vol. 13, pp. 616-630 (2012).
Morikawa et al., "TGF-beta and the TGF-beta family: Context-dependent roles in cell and tissue physiology." Cold Spring Harb. Perspect. Biol., vol. 8, Article ID a021873 (2016).
Nance et al., "Transcriptome analysis reveals differential splicing events in ipf lung tissue." PLoS One, vol. 9, pp. 1-15 (2014).
Olsen et al., "Hepatic stellate cells require a stiff environment for myofibroblastic differentiation." Am. J. Physiol. Gastrointest. Liver. Physiol., vol. 301, pp. G110-G118 (2011).
Osada et al., "XMAN1, an inner nuclear membrane protein, antagonizes BMP signaling by interacting with Smad1 in xenopus embryos." Development, vol. 130, pp. 1783-1794 (2003).
Ostlund et al., "Dependence of diffusional mobility of integral inner nuclear membrane proteins on a-type lamins." Biochemistry, vol. 45, pp. 1374-1382 (2006).
Padmakumar et al., "The inner nuclear membrane protein sun1 mediates the anchorage of nesprin-2 to the nuclear envelope." J. Cell Sci., vol. 118, pp. 3419-3430 (2005).
Pan et al., "The integral inner nuclear membrane protein MAN1 physically interacts with the r-Smad proteins to repress signaling by the transforming growth factor-beta superfamily of cytokines." J. Biol. Chem., vol. 280, pp. 15992-16001 (2005).
Park et al., "The effect of matrix stiffness on the differentiation of mesenchymal stem cells in response to TGF-beta." Biomaterials, vol. 32, pp. 3921-3930 (2011).
Peter et al., "In vitro disassembly of the nuclear lamina and m phase-specific phosphorylation of lamins by cdc2 kinase." Cell, vol. 61, pp. 591-602 (1990).
Pope et al., "Buschke-ollendorff syndrome: a novel case series and systematic review." Br. J. Dermatol., vol. 174, pp. 723-729 (2016).
Radisky et al., "Rac1b and reactive oxygen species mediate mmp-3-induced emt and genomic instability." Nature, vol. 436, pp. 123-127 (2005).
Rajgor et al., "Identification of novel nesprin-1 binding partners and cytoplasmic matrin-3 in processing bodies." Mol. Biol. of the Cell, vol. 27, pp. 3894-3902 (2016).
Rajgor et al., "Mammalian microtubule p-body dynamics are mediated by nesprin-1." J. Cell Biol., vol. 205, pp. 457-475 (2014).
Rajgor et al., "Multiple novel nesprin-1 and nesprin-2 variants act as versatile tissue-specific intracellular scaffolds." PLoS One, vol. 7, Article ID e40098 (2012).
Raju et al., "Sane, a novel lem domain protein, regulates bone morphogenetic protein signaling through interaction with Smad1." J. Biol. Chem., vol. 278, pp. 428-437 (2003).
Rho et al., "Identification of valid reference genes for gene expression studies of human stomach cancer by reverse transcription-qpcr." BMC Cancer, vol. 10, p. 240 (2010).
Richeldi et al., "Efficacy and safety of nintedanib in pulmonary fibrosis." N. Engl. J. Med., vol. 370, pp. 2071-2082 (2014).
Rinker et al., "Microparticle-mediated sequestration of cell-secreted proteins to modulate chondrocytic differentiation." Acta Biomater., vol. 68, pp. 125-136 (2017).

(56) References Cited

OTHER PUBLICATIONS

Ruijter et al., "Fluorescent-increase kinetics of different fluorescent reporters used for qpcr depend on monitoring chemistry, targeted sequence, type of dna input and per efficiency." Mikrochim. Acta, vol. 181, pp. 1689-1696 (2014).
Samarakoon et al., "TGF-beta1-induced plasminogen activator inhibitor-1 expression in vascular smooth muscle cells requires pp60(c-src)/egfr(y845) and rho/rock signaling." J. Mol. Cell Cardiol., vol. 44, pp. 527-538 (2008).
Santos et al., "Identification of a novel human lap1 isoform that is regulated by protein phosphorylation." PLoS One, vol. 9, Article ID e113732 (2014).
Shi et al., "Substrate stiffness influences TGF-beta1-induced differentiation of bronchial fibroblasts into myofibroblasts in airway remodeling." Mol. Med. Rep., vol. 7, pp. 419-424 (2013).
Song et al., "Prosper: An integrated feature-based tool for predicting protease substrate cleavage sites." PLoS One, vol. 7, pp. 1-23 (2012).
Srivastava et al., "Overexpression of cathepsin k in mice decreases collagen deposition and lung resistance in response to bleomycin-induced pulmonary fibrosis." Respir. Res., vol. 9, p. 54 (2008).
Stahnke et al., "Suppression of TGF-beta pathway by pirfenidone decreases extracellular matrix deposition on ocular fibroblasts in vitro." PLoS One, vol. 12, Article ID e0172592 (2017).
Starr et al., "Role of anc-1 in tethering nuclei to the actin cytoskeleton." Science, vol. 298, pp. 406-409 (2002).
Szeto et al., "Yap/taz are mechanoregulators of TGF-beta-Smad signaling and renal fibrogenesis." J. Am. Soc. Nephrol., vol. 27, pp. 3117-3128 (2016).
Vancheri et al., "Nintedanib with add-on pirfenidone in idiopathic pulmonary fibrosis: Results of the injourney trial." Am. J. Respir. Crit. Mare Med., vol. 197, pp. 356-363 (2017).
Varelas et al., "Taz controls Smad nucleocytoplasmic shuttling and regulates human embryonic stem-cell self-renewal." Nat. Cell Biol., vol. 10, pp. 837-848 (2008).
Wagner et al., "The *Drosophila melanogaster* lem-domain protein MAN1." Eur. J. Cell Biol., vol. 85, pp. 91-105 (2006).
Walton et al., "Targeting TGF-beta mediated Smad signaling for the prevention of fibrosis." Front Pharmacol., vol. 8, p. 461 (2017).
Wang et al., "Unsupervised gene expression analyses identify ipf-severity correlated signatures, associated genes and biomarkers." BMC Pulm. Med., vol. 17 (2017).
Wipff et al., "Myofibroblast contraction activates latent TGF-beta1 from the extracellular matrix." J. Cell. Biol., vol. 179, pp. 1311-1323 (2007).
Wu et al., "Intracellular trafficking of MAN1, an integral protein of the nuclear envelope inner membrane." J. Cell Sci., vol. 115, pp. 1361-1371 (2002).
Yadegari et al., "Buschke-ollendorff syndrome: absence of LEMD3 mutation in an affected family." Arch Dermatol., vol. 146, pp. 63-68 (2010).
Yamashita et al., "Matrix metalloproteinase 3 is a mediator of pulmonary fibrosis." Am. J. Pathol., vol. 179, pp. 1733-1745 (2011).
Yuste-Chaves et al., "Buschke-ollendorff syndrome with striking phenotypic variation resulting from a novel c.2203c>t nonsense mutation in LEMD3." Pediatr. Dermatol., vol. 28, pp. 447-450 (2011).
Zeisberg et al., "Cellular mechanisms of tissue fibrosis. 1. common and organ-specific mechanisms associated with tissue fibrosis." Am. J. Physiol. Cell. Physiol., vol. 304, pp. C216-C225 (2013).
Zhang et al., "Isoforms of the nuclear envelope protein nurim are differentially expressed during heart development in mice." Gene, vol. 627, pp. 123-128 (2017).
Zhang et al., "Nesprins: a novel family of spectrin-repeat-containing proteins that localize to the nuclear membrane in multiple tissues." J. Cell Sci., vol. 114, pp. 4485-4498 (2001).
Zuo et al., "Gene expression analysis reveals matrilysin as a key regulator of pulmonary fibrosis in mice and humans." Proc. Natl. Acad. Sci. USA, vol. 99, pp. 6292-6297 (2002).
Zurla et al., "Enhancer RNAs: Methods and Protocols" (Ørom, U. A., ed), pp. 155-170, Springer New York, New York, NY (2017).
Fukuda et al., "Localization of matrix metalloproteinases-1, -2 and -9 and tissue inhibitor of metalloproteinase-2 in interstitial lung diseases." Lab Invest., vol. 78, pp. 687-698 (1998) Abstract.

\* cited by examiner

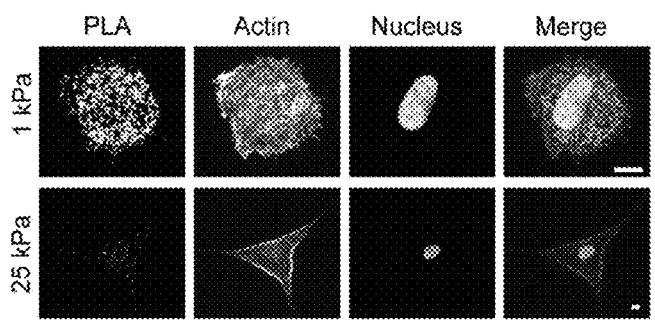
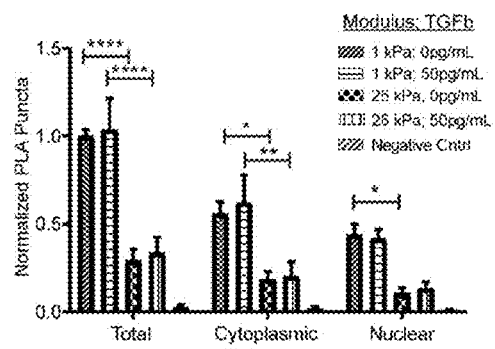
Fig. 2A
Fig. 2B
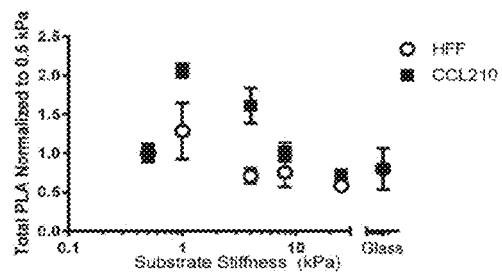
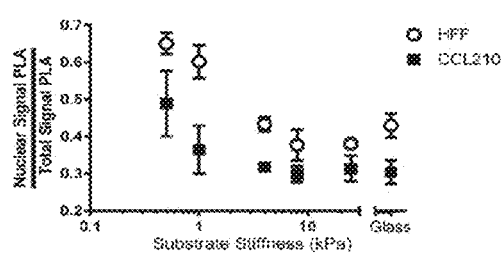
Fig. 2C
Fig. 2D
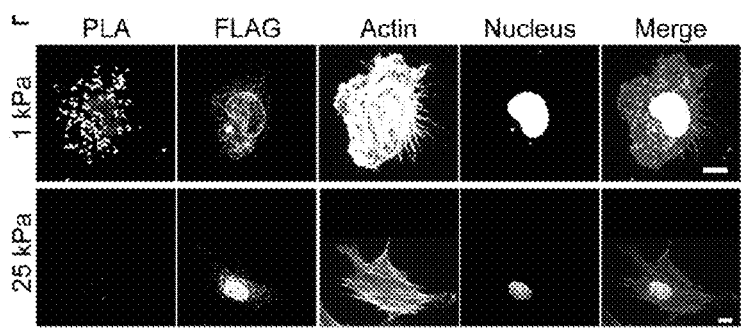
Fig. 2E
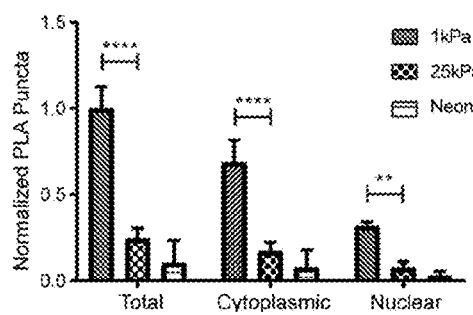
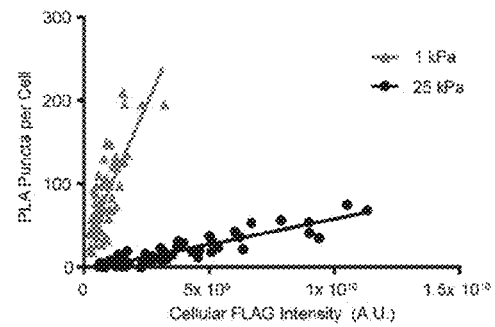
Fig. 2F
Fig. 2G

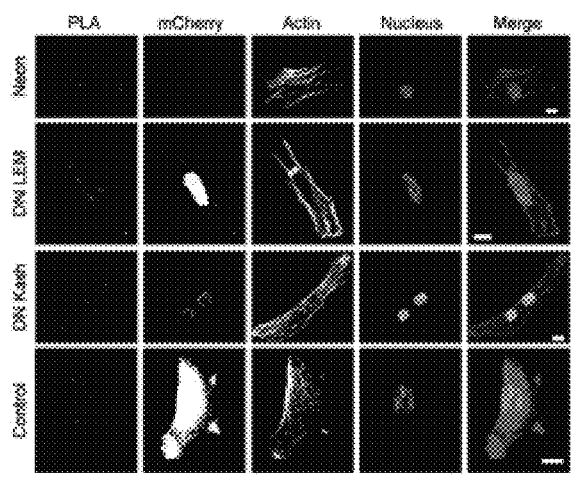
Fig. 3A
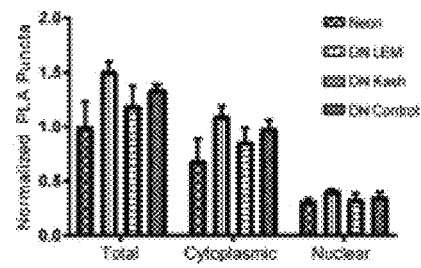
Fig. 3B
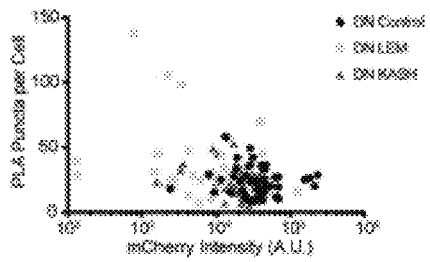
Fig. 3C
Fig. 3D
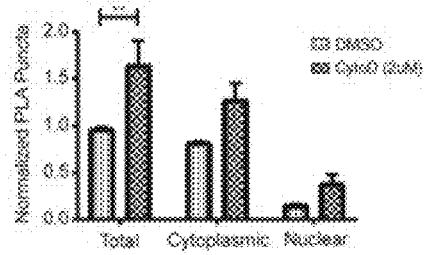
Fig. 3E
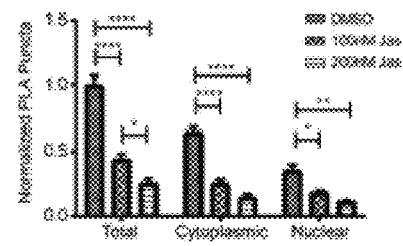
Fig. 3F

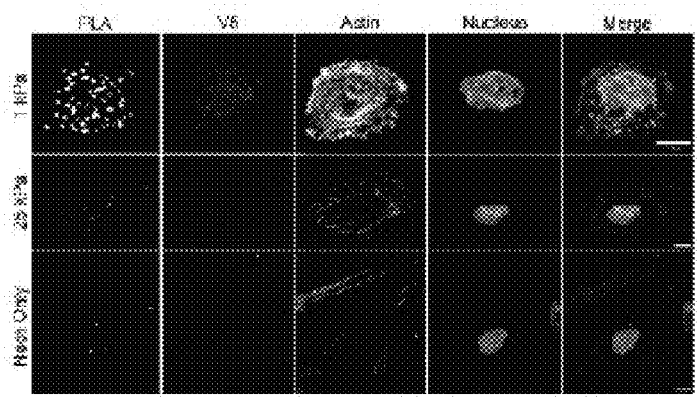 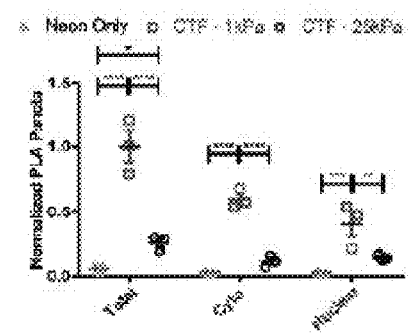
Fig. 5A    Fig. 5B
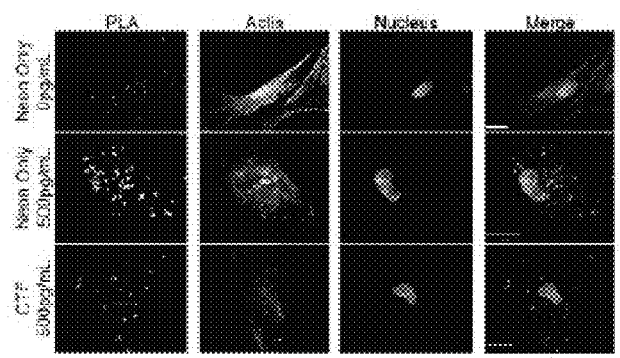 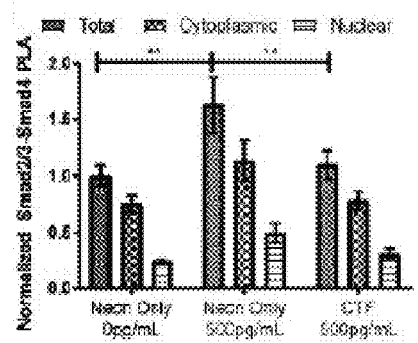
Fig. 5C    Fig. 5D
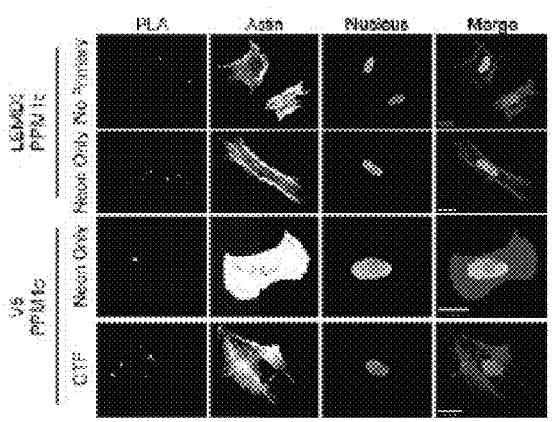 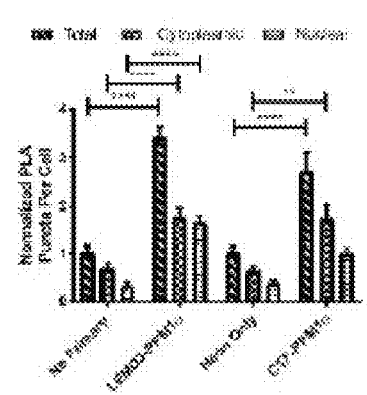
Fig. 5E    Fig. 5F

LEMD3 ANTAGONIZES TGF-BETA-DRIVEN SMAD2/3 TRANSCRIPTION IN A STIFFNESS-DEPENDENT FASHION IN BOTH THE NUCLEUS AND CYTOSOL

CROSS REFERENCE TO RELATED APPLICATIONS

This application claims the benefit of U.S. Provisional Patent Application Ser. No. 62/743,049, filed Oct. 9, 2018, the disclosure of which is incorporated herein by reference in its entirety.

GOVERNMENT INTEREST

This invention was made with government support under Grant Nos. HL127283 and HL132585 awarded by the National Institutes of Health. The government has certain rights in the invention.

TECHNICAL FIELD

The presently disclosed subject matter relates to compositions and methods for modulating transforming growth factor-beta (TGFβ) biological activity in a vertebrate subject in need thereof. In particular, the presently disclosed subject matter relates to compositions and methods useful for modulating activity of LEMD3 in a vertebrate subject 20 to thereby modulate TGFβ biological activity in the vertebrate subject.

BACKGROUND

Transforming growth factor beta (TGFβ) plays roles in human development, wound repair, and pathology. For example, over-activation of TGFβ signaling has been implicated 25 as a pathologic driver of fibrosis in several organ systems including the lung, kidneys, skin and liver (1-3). Recently, the FDA approved the use of pirfenidone in pulmonary fibrosis, which acts in part to antagonize TGFβ signaling. Pirfenidone has led to a slowing of disease progression, indicating that this is a promising yet not fully realized therapeutic axis for addressing fibrotic pathologies. (4-7).

Thus, there continues to be a long felt need in the art for compositions and methods useful to modulate TGFβ signaling for therapeutic interventions. The presently disclosed subject matter addresses these and other needs in the art.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides a method of modulating transforming growth factor-beta (TGFβ) biological activity in a vertebrate subject in need thereof. In some embodiments, the method comprises administering to the vertebrate subject an effective amount of a substance capable of modulating activity of LEMD3 in the vertebrate subject to thereby modulate TGFβ biological activity in the vertebrate subject.

In some embodiments, the substance that modulates the LEMD3 activity comprises an isolated LEMD3 polypeptide. In some embodiments, the administering further comprises administering an effective amount of a substance that modulates expression of LEMD3-encoding nucleic acid molecule in the vertebrate. In some embodiments, the substance that modulates expression of a LEMD3-encoding nucleic acid molecule comprises an effective amount of a siRNA, a vector encoding the siRNA, or combinations thereof.

In some embodiments, the administering further comprises administering to said vertebrate subject a vector comprising a nucleic acid sequence encoding a LEMD3 polypeptide operatively linked to a promoter, wherein production of the LEMD3 polypeptide in the subject results in modulation of TGFβ biological activity. In some embodiments, the vector further comprises a vector selected from the group consisting of a plasmid vector and a viral vector. In some embodiments, the vector further comprises a liposome complex.

In some embodiments, the LEMD3 polypeptide comprises a polypeptide selected from the group consisting of a polypeptide having an amino acid sequence as set forth in SEQ ID NO:24, a fragment thereof, a polypeptide having an amino acid sequence having 95% homology to SEQ ID NO:24, and a fragment thereof. In some embodiments, the fragment comprises SEQ ID NO: 25 or SEQ ID NO:27, a fragment of SEQ ID NO: 25 or SEQ ID NO:27, or a sequence having about 95% homology to SEQ ID NO:25 or SEQ ID NO:27.

In some embodiments, the nucleic acid sequence is selected from the group consisting of: (a) a nucleic acid sequence encoding a polypeptide comprising an amino acid sequence as set forth in SEQ ID NOs:24, 25, or 29; a fragment thereof, a polypeptide having an amino acid sequence having 95% homology to SEQ ID NOs: 24, 25, or 29, and a fragment thereof; (b) a nucleic acid sequence as set forth in any of SEQ ID NOs: 26, 27, or 28, or its complementary strands; (c) a nucleic acid sequence having 95% homology to a nucleic acid sequence as set forth in any of SEQ ID NOs: 26, 27, or 28, and which encodes a LEMD3 polypeptide; and (d) a nucleic acid sequence differing from an isolated nucleic acid molecule of (a), (b), or (c) above due to degeneracy of the genetic code, and which encodes a LEMD3 polypeptide encoded by the isolated nucleic acid molecule of (a), (b), or (c) above.

In some embodiments, the amino acid sequence comprises at least one modification selected from the group consisting of an amino acid deletion, an amino acid addition, an amino acid substitution, and combinations thereof.

In some embodiments, the vertebrate subject is suffering from fibrosis. In some embodiments, the subject is a mammal.

In some embodiments, the presently disclosed subject matter provides a method of treating fibrosis in a vertebrate subject in need thereof, the method comprising the step of administering to the vertebrate subject an effective amount of a substance capable of modulating activity of LEMD3 in the vertebrate subject. In some embodiments, the subject is a mammal.

In some embodiments, the substance that modulates the LEMD3 activity comprises a LEMD3 polypeptide. In some embodiments, the step of administering further comprises administering to said vertebrate subject a vector comprising a nucleic acid sequence encoding a LEMD3 polypeptide operatively linked to a promoter. In some embodiments, the vector further comprises a vector selected from the group consisting of a plasmid vector and a viral vector. In some embodiments, the vector further comprises a liposome complex.

In some embodiments, the LEMD3 polypeptide comprises a polypeptide selected from the group consisting of a polypeptide having an amino acid sequence as set forth in SEQ ID NO:24, a fragment thereof, a polypeptide having an amino acid sequence having 95% homology to SEQ ID NO:24, and a fragment thereof. In some embodiments, the fragment comprises SEQ ID NO: 25 or SEQ ID NO:27, a fragment of SEQ ID NO: 25 or SEQ ID NO:27, or a sequence having 95% homology to SEQ ID NO:25 or SEQ ID NO:27.

In some embodiments, the nucleic acid sequence is selected from the group consisting of: (a) a nucleic acid sequence encoding a polypeptide comprising an amino acid sequence as set forth in SEQ ID NOs:24, 25, or 29; a fragment thereof, a polypeptide having an amino acid sequence having 95% homology to SEQ ID NOs: 24, 25, or 29, and a fragment thereof; (b) a nucleic acid sequence as set forth in any of SEQ ID NOs: 26, 27, or 28, or its complementary strands; (c) a nucleic acid sequence having 95% homology to a nucleic acid sequence as set forth in any of SEQ ID NOs: 26, 27, or 28, and which encodes a LEMD3 polypeptide; and (d) a nucleic acid sequence differing from an isolated nucleic acid molecule of (a), (b), or (c) above due to degeneracy of the genetic code, and which encodes a LEMD3 polypeptide encoded by the isolated nucleic acid molecule of (a), (b), or (c) above.

In some embodiments, the amino acid sequence comprises at least one modification selected from the group consisting of an amino acid deletion, an amino acid addition, an amino acid substitution, and combinations thereof.

In some embodiments, the presently disclosed subject matter provides a composition comprising a substance capable of modulating activity of LEMD3 in a vertebrate subject, wherein the substance is selected from the group consisting of: an isolated and purified LEMD3 polypeptide; (b) an effective amount of a siRNA that modulates expression of a LEMD3-encoding nucleic acid molecule, a vector encoding the siRNA, or combinations thereof; and (c) a vector comprising a nucleic acid sequence encoding a LEMD3 polypeptide operatively linked to a promoter. In some embodiments, the composition comprises a pharmaceutically acceptable diluent or vehicle.

In some embodiments, the LEMD3 polypeptide comprises a polypeptide selected from the group consisting of a polypeptide having an amino acid sequence as set forth in SEQ ID NO:24, a fragment thereof, a polypeptide having an amino acid sequence having 95% homology to SEQ ID NO:24, and a fragment thereof. In some embodiments, the fragment comprises SEQ ID NO: 25 or SEQ ID NO:27, a fragment of SEQ ID NO: 25 or SEQ ID NO:27, or a sequence having 95% homology to SEQ ID NO:25 or SEQ ID NO:27.

In some embodiments, the nucleic acid sequence is selected from the group consisting of: (a) a nucleic acid sequence encoding a polypeptide comprising an amino acid sequence as set forth in SEQ ID NOs:24, 25, or 29; a fragment thereof, a polypeptide having an amino acid sequence having 95% homology to SEQ ID NOs: 24, 25, or 29, and a fragment thereof; (b) a nucleic acid sequence as set forth in any of SEQ ID NOs: 26, 27, or 28, or its complementary strands; (c) a nucleic acid sequence having 95% homology to a nucleic acid sequence as set forth in any of SEQ ID NOs: 26, 27, or 28, and which encodes a LEMD3 polypeptide; and (d) a nucleic acid sequence differing from an isolated nucleic acid molecule of (a), (b), or (c) above due to degeneracy of the genetic code, and which encodes a LEMD3 polypeptide encoded by the isolated nucleic acid molecule of (a), (b), or (c) above.

In some embodiments, the amino acid sequence comprises at least one modification selected from the group consisting of an amino acid deletion, an amino acid addition, an amino acid substitution, and combinations thereof.

In some embodiments, the vector encoding the siRNA comprises: a promoter operatively linked to a nucleic acid molecule encoding the siRNA molecule; and a transcription termination sequence.

In some embodiments, the presently disclosed subject matter provides a kit comprising a composition in accordance with the presently disclosed subject matter and at least one reagent and/or device for introducing the composition into a cell, tissue, and/or subject. In some embodiments, the kit further comprises instructions for introducing the composition in a cell, tissue, or subject.

Accordingly, it is an object of the presently disclosed subject matter to provide compositions and methods for modulating transforming growth factor-beta (TGFβ) biological activity. This and other objects are achieved in whole or in part by the presently disclosed subject matter. Further, objects of the presently disclosed subject matter having been stated above, other objects and advantages of the presently disclosed subject matter will become apparent to those skilled in the art after a study of the following description, Figures, and EXAMPLES. Additionally, various aspects and embodiments of the presently disclosed subject matter are described in further detail below.

BRIEF DESCRIPTION OF THE FIGURES

The patent or application file contains at least one drawing executed in color. Copies of this patent or patent application publication with color drawings will be provided by the United States Patent and Trademark Office upon request and payment of the necessary fee.

In FIG. 1A, fibroblasts demonstrated mechano-sensitivity to ECM stiffness through cytoskeletal compliance matching as measured by AFM on increasingly stiff matrices (p=0.001). In FIG. 1B, fibroblasts stably transfected with Smad-responsive luciferase demonstrated a dose-dependent, stiffness modulation of their TGFβ responsiveness. Increasing doses of TGFβ were associated with a softer sigmoidal inflection point (p=0.07) and cells demonstrated a dose-response to TGFβ on stiff surfaces (p<0.0001). In FIG. 1C, LEMD3 expression was correlated with a stiffer transition point in TGFβ-stiffness responsiveness (p<0.0001) and with decreased luminescence (p=0.04). In FIG. 1 D, cytoskeletal depolymerization but not myosin II inhibition was associated with a decreased and flattened luminescent response of fibroblasts to TGFβ. LEMD3 KD does not rescue actin-depolymerization phenotype. Treatments with cytochalasin D did not converge to a sigmoidal model and the data is represented as mean with standard error of the mean to convey the heterogenity of the results. All cell stiffness/morphology phenotypes and stiffness model parameters were statistically analyzed using an ANOVA—Test for Trends analysis. All data represented by the mean with SEM unless otherwise noted.

FIGS. 2A through 2G show that LEMD3-Smad2/3 interactions are inversely correlated to substrate stiffness and occur in the nucleus and cytoplasm. In FIG. 2A, micrographs of LEMD3-Smad2/3 PLA interactions on soft (top row, 1 kPa) and stiff (bottom row, 25 kPa) matrices (PLA in green, f-Actin in blue, nucleus in white). In FIG. 2B, quantification of PLA interactions grouped by substrate stiffness and by TGFβ dose. Total LEMD3-Smad2/3 interactions were negatively correlated to substrate stiffness (p<0.0001 for 1 kPa vs 25 kPa for both 0 pg/mL and 50 pg/mL TGFβ) but not correlated to TGFβ dose. Cytoplasmic (p=0.0164 for 0 pg/mL TGFβ. p=0.0087 for 50 pg/mL TGFβ) and nuclear compartment (p=0.0428 for 0 pg/mL TGFβ, p=0.1228 for 50 pg/mL TGFβ) interactions were also negatively correlated to substrate stiffness. In FIG. 2C, total HFFs and CCL210s LEMD3-Smad2/3 interactions by PLA normalized to 0.5 kPa on surfaces with stiffness of 0.5, 1, 4, 8, 25 kPa and glass. Each fibroblast population showed a biphasic trend, centered around a peak of LEMD3-Smad2/3 interactions at 1 kPa. CCL210 demonstrated greater dynamic range in interaction frequency and a slower loss of interactions on stiffer substrates than HFFs. In FIG. 2D, subcellular location of LEMD3-Smad2/3 PLA interactions in HFFs and CCL210s from FIG. 2C. Each cell line demonstrated a cytoplasmic shift in location with increasing substrate stiffness (p<0.0001 and p=0.0199 for HFFs and CCL210s, respectively; ANOVA—Test for trend). In FIG. 2E, micrographs of V5-Smad2/3 PLA interactions with pFLAG-LEMD3-V5 on soft (top row) and stiff (bottom row) matrices (PLA in green, f-actin in blue, FLAG in red, nucleus in white). In FIG. 2F, V5-Smad2/3 PLA interactions were also negatively correlated with substrate stiffness (for 1 kPa vs 25 kPa: Total PLA—p<0.0001, Cytoplasmic PLA—p<0.0001, Nuclear PLA—p=0.0018) and also occurred in the cytoplasm. In FIG. 2G, V5-Smad2/3 PLA interactions were a significantly higher on soft substrates independent of the degree of pFLAG-LEMD3-V5 expression (difference in linear regression slopes—p<0.0001). All PLA groups were statistically compared using a 2-way ANOVA with Tukey post-test unless noted. All scale bars are 10 μm. All data represented by the mean with SEM except FIG. 2G where individual data points are plotted.

FIGS. 3A through 3F show that LEMD3-Smad2/3 interactions are negatively associated with actin polymerization but not nucleus-cytoplasm coupling or LEMD3-lamin coupling. In FIG. 3A, micrographs of LEMD3-Smad2/3 PLA in electroporated cells (top row), mCherry-DN LEM expressing cells ($2^{nd}$ row), mCherry-DN Kash expressing cells ($3^{rd}$ row), or mCherry only expressing cells (bottom row), all on glass (PLA in green, f-actin in blue, mCherry in red, nucleus in white). In FIG. 3B, no significant differences in PLA frequency were seen in the nucleus or cytoplasm of cells expressing either DN LEM or DN Kash relative to mCherry control cells. In FIG. 3C, no correlation between DN LEM or DN Kash expression level and PLA frequency in transfected cells. In FIG. 3D, micrographs of LEMD3-Smad2/3 PLA in cells treated with cytochalasin D (top rows, g-actin stabilizer) on glass or jasplakinolide (bottom rows, f-actin stabilizer) on 1 kPa gels (PLA in green, f-actin in blue, nucleus in white). In FIG. 3E, cytochalasin D treatment significantly increased the total frequency (p=0.0089) of PLA interactions per cell on glass. In FIG. 3F, jasplakinolide (Jas) treatment significantly decreased the total frequency of LEMD3-Smad2/3 interactions in a dose-dependent fashion (p<0.0001 for DMSO vs. 100 nM Jas or 200 nM Jas, p=0.0312 for 100 nM Jas vs. 200 nM Jas), and decreased the cytoplasmic (p<0.0001 for DMSO vs. 100 nM Jas or 200 nM Jas) and nuclear frequencies (p=0.002 for DMSO vs. 200 nM Jas, p=0.0466 for DMSO vs. 100 nM Jas) of LEMD3-Smad2/3 interactions on 1 kPa surfaces. All groups were statistically compared using a 2-way ANOVA with Tukey post-test. All scale bars are 10 μm. All data represented by the mean with SEM except Panel (C) where individual data points are plotted.

In FIG. 4A, Peptide spectral matches (PSMs) were normalized from a 60 kDa FLAG fragment of LEMD3 by PSM frequencies measured in full length LEMD3. Normalized PSM frequency revealed three distinct zones: over-enriched (left shaded region), under-enriched (unshaded region), and absent (right shaded region). FIG. 4B shows a LEMD3 cartoon showing relative position of the two deletion mutants and known protein domains: LEM, transmembrane (TMs 1&2), and RRM domains, and FLAG and V5 epitope tags. FIG. 4C shows western blots from full length and each deletion mutant using N-terminal FLAG tag (top two blots) and C-terminal V5 tag (bottom two blots) at 12 and 24 hours after electroporation. FLAG blots consistently produced a 60 kDa fragment, while V5 blots produced 85 kDa, 60 kDa, and 46 kDa fragments. FIG. 4D shows representative western blots for protease and cell cycle inhibitor experiments using N-terminal FLAG tag (top two blots) and C-terminal V5 tag (bottom two blots). FIG. 4E shows the quantification of blots from FIG. 4D, showing that 60 kDa FLAG fragment was significantly reduced relative to the full-length protein when cells were treated with DCI (p=0.0153), MG-132 (p=0.0238), Cathepsin-G inhibitor (p=0.0075), or roscovitine (p=0.0051). V5-tagged 46 kDa fragment was similar in that DCI (p<0.0001) and MG-132 (p=0.0238) treatments decreased its abundance, but dissimilar in that roscovitine increased its abundance (p<0.0001). V5-tagged 85 kDa fragment was increased with MMP inhibitor treatment (p=0.0004) and E64D treatment (p=0.0044). All treatment groups, except MG-132, were tested statistically using ANOVA—Test for Trends with a correction for multiple hypotheses using a False Discovery Rate (FDR) of α=0.05. MG-132 was compared to DMSO treated lysates with a Mann-Whitney test and then also corrected using the FDR approach above. All data in Panel (E) represented by the mean with SEM.

FIGS. 5A through 5F show C-Terminal fragments of LEMD3 bind Smad2/3 and antagonize Smad2/3-Smad4 complexes. FIG. 5A shows representative images of V5-Smad2/3 PLA reactions imaged in fibroblasts transfected with pFLAG-LEMD3p.Δ21-669-V5 (top two rows) and electroporation control cells (bottom row, "Neon Only") on 1 kPa and 25 kPa hydrogel surfaces (PLA in green, f-actin in blue, V5 in red, nucleus in white). FIG. 5B shows PLA interactions from (A) between the V5 tag of a C-terminal fragment ("CTF") of LEMD3 (pFLAG-LEMD3p.Δ21-669-V5) and Smad2/3, normalized to the total interactions observed on 1 kPa hydrogels. HFFs on 1 kPa hydrogels have significantly more interactions overall (p<0.0001), in the cytosol (p<0.0001), and in the nucleus (p=0.0082) relative to fibroblasts on 25 kPa hydrogels. All transfected cells had more PLA interactions than electroporation-only ("Neon") populations (p<0.0001 and p<0.0227 for 1 kPa and 25 kPa hydrogels, respectively). Scale bars are 11 μm. All statistical testing done with 2-way ANOVA with Tukey's post-test. FIG. 5C shows representative images from HFFs on 1 kPa hydrogels assayed for Smad2/3-Smad4 interactions. Cells in the 2nd and $3^{rd}$ rows were treated with 500 pg/mL TGFβ for 1 hour before fixation, while cells in the first row were untreated. Cells in the 3$^{rd}$ row were electroporated with pFLAG-LEMD3p.Δ21-669-V5 while cells in the top two rows were electroporation control cells (PLA in green, f-actin in blue, nucleus in white). All scale bars are 17 μm. FIG. 5D shows normalized quantification of data from FIG. 5C. Fibroblasts treated with 500 pg/mL TGFβ and overexpressing the CTF of LEMD3 had significantly less Smad2/3-Smad4 complexes than untransfected cells treated with 500 pg/mL TGFβ (p=0.0081). Untransfected TGFβ fibroblasts treated with 500 pg/mL also had significantly more Smad2/3-Smad4 complexes than untransfected fibroblasts (p=0.001). All statistical testing done with a 2-way ANOVA with Tukey's post-test. FIG. 5E shows interactions between PPM1α and endogenous LEMD3 or its CTF assayed by PLA on glass surfaces. The first and 2nd rows used antibody pairs between PPM1α and endogenous LEMD3. The 3$^{rd}$ and 4$^{th}$ rows used antibody pairs between PPM1α and V5 tag on cells transfected with pFLAG-LEMD3p.Δ21-669-V5 (PLA in green, f-actin in blue, nucleus in white). All scale bars are 17 μm. FIG. 5F shows normalized quantification of the interaction rates between LEMD3 or its CTF by subcellular compartment. Both endogenous LEMD3 and its CTF interacted with PPM1α as demonstrated by PLA frequencies above their respective negative controls (for "Total" interactions: p<0.0001 for both LEMD3 vs. No Primary and for CTF vs. Neon Only, respectively). Both LEMD3 and CTF transfected cells also had significantly higher PPM1α interaction rates than their respective controls in the cytoplasm (for "Cytoplasmic" rates: p<0.0001 and p=0.0081 for LEMD3 and CTF pairs, respectively), but only endogenous LEMD3 had statistically significant higher interaction rate in the nucleus (for "Nuclear" rates: p<0.0001 and p=0.2569 for endogenous LEMD3 and CTF-expressing fibroblasts, respectively). All statistical testing was performed by a 2-way ANOVA with Sidak's post-test. All data represented by the mean with SEM.

FIGS. 6A and 6B show LEMD3-Smad2/3 PLA frequency imaged at high-magnification (63×) (A) and low-magnification (20×) (B) in non-IPF (top row) and IPF (bottom row) tissue (PLA in green, f-actin in blue, autofluorescence in red, nuclei in white). In FIG. 6C, quantification of sub-cellular localization of LEMD3-Smad2/3 PLA events from FIG. 6A showed a cytoplasmic shift in PLA interactions in IPF patients (p=0.0307, Mann-Whitney test), mirroring in vitro trends seen in FIG. 2C. FIG. 6D shows quantification of total LEMD3-Smad2/3 PLA frequency from FIG. 6B showed a similar frequency of interactions between IPF and non-IPF patients (p=0.5783, Mann-Whitney test). IPF tissue had a higher intra-patient variability (Coeff. of Variance=67% and 30% for IPF and non-IPF patients, respectively) and more extreme dispersion overall (kurtosis=4.765 and −0.1391 for IPF and non-IPF patients, respectively). 22% of IPF tissue areas sampled formed a unique low-interaction "tail" (<25% of the mean IPF interaction frequency, denoted by dotted line), which was absent in non-IPF tissues. All scale bars are 10 μM. Bars in FIGS. 6C and 6D represent grand medians.

FIGS. 9A and 9B show representative western blots and quantification from plasmid over-expression (FIG. 9A) and siRNA knockdown experiments (FIG. 9B). pFLAG-LEMD3-V5 electroporation significantly increased full length LEMD3 (p=0.0018 for HFF vs. 1 pg pFLAG-LEMD3-V5, p=0.0012 for Neon Only vs. 1 μg pFLAG-LEMD3-V5, ANOVA with Tukey post-test). siLEMD3 delivered by Lipofectamine 2000 (L2K) significantly decreased LEMD3 expression relative to siGFP control (p=0.0248, Student's T-test). All data represented by the mean with SEM. In FIG. 10A, Phospho-Smad3 to Smad3 ratios were measured by western blot in HFFs on tissue culture plastic. HFFs treated with 100 pg/mL TGFβ for 90 minutes had an increased pSmad3/Smad3 ratio relative to untreated fibroblasts (p=0.0506). HFFs treated with 100 pg/mL TGFβ and 25 nM or 200 nM siRNA against LEMD3 ("siLEMD3") had a higher pSmad3/Smad3 ratio than cells treated with a concentration matched siRNA against GFP ("siGFP"; p=0.1103 and p=0.0057 for 25 nM and 200 nM, respectively, Student's T-test). TGFβ dosed HFFs electroporated with pFLAG-LEMD3-V5 ("FL-OE") or pFLAG-LEMD3p.Δ21-669-V5 ("CTF-OE") had diminished pSmad3/Smad3 ratios relative to TGFβ treated HFFs (p=0.0124 and p=0.2116 for CTF-OE and FL-OE, respectively) but were not statistically different from the electroporation-only ("Neon Only") control. FIG. 10B shows representative blots for Smad2/3 and phospho-Smad2/3. Smad3 is the lower band at ≈50 kDa. All data represented by the mean with SEM.

FIG. 12A shows western blots of cytosolic (GAPDH) and nuclear (LaminA/C) compartment markers from a fractionated lysate. Cytosolic markers were observed in the nuclear lysate but no nuclear markers were observed in the cytosolic lysate. FIG. 12B is a LEMD3 western blot on whole cell lysate or enriched lysates for the cytoplasmic or nuclear fractions. An about 50 kDa native LEMD3 fragment was found in the cytoplasm and possibly the nucleus, while full length LEMD3 was only found in the nucleus.

In FIG. 13A, fibroblasts transfected with pFLAG-LEMD3-V5 were assayed by western blot for the relative abundance (fraction of total V5 signal in that lane) in the full length protein or in the 85 kDa, 60 kDa, or 45 kDa fragments after 24 hours on 1 kPa and 25 kPa hydrogels or tissue culture plastic. Fibroblasts cultured on 1 kPa and 25 kPa hydrogels have significantly less full length LEMD3 than cells cultured on tissue culture plastic ($p=0.0062$ and $p=0.0031$ for 1 kPa and 25 kPa hydrogels, respectively) but do not vary significantly in the abundance of any identified fragment. Cells on 25 kPa hydrogels have nearly twice as much of the 45 kDa fragment than cells from 1 kPa hydrogels ($p=0.5196$). FIG. 13B shows representative blots of the experimental lysates. All stiffness in a given protein mass group were statistically compared using ANOVA with Tukey post-test. Data point represented by "#" in Full Length, 1 kPa was determined to be an outlier (Grubb's method, $\alpha=0.05$) and is plotted for completeness but excluded from analysis. All data represented by the mean with SEM.

FIG. 14A shows representative western blots and quantification of LEMD3 protein from soft (2 kPa) and stiff (25 kPa) hydrogels using GAPDH as a loading control. No significant difference was observed between stiffness conditions. FIG. 14B shows LEMD3 mRNA quantification from cells on soft (2 kPa) or stiff (25 kPa) hydrogels using 18S as a housekeeping gene. No significant difference was observed between stiffness conditions. All data represented by the mean with SEM.

DETAILED DESCRIPTION

Figure 1A:
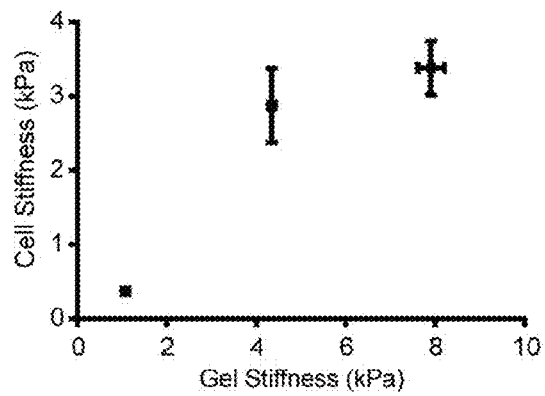
FIGS. 1A through 1D show that LEMD3 modifies the stiffness response of fibroblasts to activated TGFβ.

Transforming Growth Factor-beta (TGFβ) signaling is an important driver of fibrotic pathology in multiple organ systems including the lung, skin, liver and kidneys. TGFβ signaling and extracellular matrix (ECM) stiffness form an unvirtuous pathologic circuit where matrix stiffness drives activation of latent TGFβ and TGFβ signaling drives cellular stress and matrix synthesis. Additionally, ECM stiffness also appears to sensitize cells to exogenously activated TGFβ through unknown mechanisms. In accordance with aspects of the presently disclosed subject matter, the effect of ECM stiffness on the putative inner nuclear membrane protein LEMD3 was explored. LEMD3, a known inhibitor of TGFβ superfamily signaling, is physically connected to the cell's actin cytoskeleton. Disclosed herein is the showing that fibroblasts' LEMD3-Smad2/3 interactions were inversely correlated with ECM stiffness and TGFβ-driven luciferase activity; and, that LEMD3 expression was correlated to the mechanical response of the TGFβ-driven luciferase. It was found that actin polymerization but not cellular stress or LEMD3-nuclear-cytoplasmic couplings were necessary for LEMD3's stiffness phenotype. Intriguingly, many LEMD3-Smad2/3 interactions in the cytosol were discovered. It is shown that LEMD3 was proteolytically post-translationally modified into protein fragments. It was subsequently confirmed that a consensus C-terminal LEMD3 fragment bound Smad2/3 in a stiffness-dependent manner throughout the cell and was sufficient for the antagonism of Smad2/3's signaling. From human lung core biopsies, it was shown that nuclear and cytosolic interactions were present in tissue and found that fibrotic tissue had locally diminished and cytoplasmically shifted LEMD3-Smad2/3 interactions, in agreement with the in vitro studies. Thus, in some aspects, the presently disclosed subject matter reveals fundamental biology of LEMD3 and TGFβ and provides a target to antagonize pathologic TGFβ signaling in fibrosis.

I. GENERAL CONSIDERATIONS

TGFβ is deposited in the extracellular matrix (ECM) in an inactive state in latent-TGFβ associated protein complexes. In order to activate TGFβ, cells can mechanically disengage TGFβ from the latent complex through αv integrin mediated mechanical stress, after which TGFβ acts in a paracrine fashion. Stiffer ECMs allow for more force transmission to the latent complex and potentiate the liberation of TGFβ. This allows for pathological feedback whereby TGFβ signaling drives matrix synthesis and cellular stress, and a stiffer matrix increases the free amount of TGFβ available to cells. (8, 9) In addition to activating TGFβ, several in vitro studies have indicated that a stiff ECM potentiates cellular responses to exogenously activated (pre-activated) TGFβ. (10-13). In some aspects, the presently disclosed subject matter explored this cellular potentiation to TGFβ to identify additional targets of possible therapeutic intervention along the TGFβ signaling pathway (e.g., targets that particularly address matrix-driven sensitization to TGFβ, not matrix-driven activation of TGFβ).

In some aspects, the presently disclosed subject matter explored rigidity-driven cellular sensitization to TGFβ on LEM domain containing protein 3 (LEMD3). LEMD3 is an integral, inner nuclear membrane protein and a compelling target for two reasons: 1) it is a known inhibitor of TGFβ signaling; and 2) it is biophysically connected to the cell's cytoskeleton, which is remodeled in an ECM stiffness dependent fashion. LEMD3 binds and inactivates the downstream transcription factor partners of both TGFβ and bone morphogenic protein (BMP), the receptor proteins mothers against decapentaplegic (Smads) 2&3 and 1&5&8, respectively. (14-21) LEMD3's RNA recognition motif (RRM)

domain, on its C-terminal end, competes with other transcription factors for binding to Smad2/3 and promotes Smad2/3 dephosphorylation and nuclear export by acting as a coordinating scaffold for Protein Phosphatase, $Mg^{2+}/Mn^{2+}$ Dependent 1α ("PPM1α") (16, 22).

In humans, heterozygous loss of LEMD3 is frequently, but not always (23), associated with the development of Buschke-Ollendorf syndrome (BOS), in which patients develop some constellation of cutaneous collagenomas and elastomas (from aberrant TGFβ signaling) and osteopoikilosis (from aberrant BMP signaling), hyperostic lesions in long bones, which can mimic osteoblastic metastatic lesions radiographically. (20, 24-32) Depending on the penetrance and specific genotype, heterozygous loss of LEMD3 can also be associated with more severe ECM pathologies, such as melorheostosis, a progressive sclerosis frequently in long bones that can lead to disfigurement and joint destruction. (20, 24)

In addition to its clear role in antagonizing TGFβ signaling both in vitro and in vivo, LEMD3 is retained in the inner nuclear membrane through its connection to the nuclear lamin superstructure by the activity of its N-terminal end, which contains the molecule's Lapb2/Emerin/MAN1 (LEM) domain. (14, 33-37) This connection creates a direct biophysical link to the cell's actin microfilament network through the nesprinsun Linker of Nucleus and Cytoskeleton (LINC) complex. (38-40)

Given LEMD3's role in antagonizing Smad2/3 and its biophysical connection to the cell's cytoskeleton, it was hypothesized that LEMD3's inhibition of Smad2/3 would be reduced by cytoskeletal stress thereby potentiating TGFβ signaling in an ECM stiffness-dependent fashion. Here, dermal fibroblasts displayed ECM stiffness-dependent TGFβ responsiveness, and LEMD3 knockdown or over-expression modulated this stiffness responsiveness. The presently disclosed subject matter also showed that LEMD3's interactions with Smad2/3 were negatively regulated by ECM stiffness and were independent of TGFβ dosing. LEMD3-Smad2/3 interactions were increased by disruption of the actin cytoskeleton, but these complexes were not potentiated by disruption of the LINC complex or over-expression of the LEM domain. Unexpectedly, it was discovered cytosolic interactions between LEMD3 and Smad2/3, which called into question basic assumptions about the current understanding of LEMD3's biology and its regulation of TGFβ. N- and C-terminal LEMD3 fragments were identified and genetically localized, which separated LEMD3's Smad-binding RRM and lamin-binding LEM domains. It was established that these fragments were created through post-translational proteolysis by a serine protease and were differentially regulated by lamin integrity. It was verified that a consensus C-terminal fragment of LEMD3 bound Smad2/3 in a stiffness-dependent fashion, antagonized Smad2/3's ability to complex with Smad4, and showed that both endogenous LEMD3 and this LEMD3 fragment bound in the cytoplasm a protein phosphatase previously shown to be coordinated by LEMD3 to antagonize TGFβ signaling. Finally, correlates were found between the in vitro findings and human lung tissue from idiopathic pulmonary fibrosis (IPF) and non-IPF patients. Interactions between LEMD3 and Smad2/3 demonstrated greater intra-patient/total variability in frequency and were more frequent in the cytoplasm in human lung core biopsies from IPF patients relative to non-IPF tissues. Additionally, IPF tissues had unique low-frequency LEMD3-Smad2/3 interaction regions, possibly indicative of local fibrotic disease. The presently disclosed subject matter provides novel aspects of LEMD3 biology as well as identifies a target for TGFβ antagonism relevant to fibrosis that complements current medical management.

Pulmonary fibrosis (PF) is a disease in which lung tissue becomes thick, stiff and scarred over time. Scarred lung tissue hinders the movement of oxygen from the lungs into the bloodstream, thus reducing the amount of available oxygen in circulation for the body (see e.g., the website of the National Heart, Lung, and Blood Institute; King et al., 2011, Lancet 378(9807):1949-1961). Idiopathic Pulmonary Fibrosis (IPF; Raghu & Mikacenic, 2018, Pathogenesis of idiopathic pulmonary fibrosis. Available from the website of UPTODATE®, Wolters Kluwer, Riverwoods, Ill., United States of America), one of at least 200 different forms of PF, is a chronic state of fibrosis that leads to an irreversible decline in lung functionality. IPF affects 1 out of 200 adults over the age of 65, with 50,000 adults diagnosed and another 40,000 deaths from IPF each year (Pulmonary Fibrosis Foundation, 2018). Immediate treatment is required in order to slow the progression of IPF.

II. DEFINITIONS

Headings are included herein for reference and to aid in locating certain sections. These headings are not intended to limit the scope of the concepts described therein under, and these concepts may have applicability in other sections throughout the entire specification.

In describing and claiming the presently disclosed subject matter, the following terminology will be used in accordance with the definitions set forth below.

The terminology used herein is for the purpose of describing particular embodiments only and is not intended to be limiting of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the presently disclosed subject matter and the claims.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The articles "a" and "an" are used herein to refer to one or to more than one (i.e., to at least one) of the grammatical object of the article. By way of example, "an element" means one element or more than one element.

The term "about", as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In some embodiments, the term "about" means plus or minus 10% of the numerical value of the number with which it is being used. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about".

The terms "additional therapeutically active compound" or "additional therapeutic agent", as used in the context of the presently disclosed subject matter, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated. Disease and disorders being treated by the additional therapeutically active agent include, for example, fibrosis. The additional compounds may also be used to treat symptoms associated with the injury, disease, or disorder, including, but not limited to, pain and inflammation.

As use herein, the terms "administration of" and or "administering" a compound should be understood to mean providing a composition of the presently disclosed subject matter to a subject in need of treatment.

The term "adult" as used herein, is meant to refer to any non-embryonic or non-juvenile subject. For example, the term "adult adipose tissue stem cell", refers to an adipose stem cell, other than that obtained from an embryo or juvenile subject.

As used herein, an "agent" is meant to include something being contacted with a cell population to elicit an effect, such as a drug, a protein, a peptide. An "additional therapeutic agent" refers to a drug or other compound used to treat an illness and can include, for example, an antibiotic or a chemotherapeutic agent.

As used herein, an "agonist" is a composition of matter which, when administered to a mammal such as a human, enhances or extends a biological activity attributable to the level or presence of a target compound or molecule of interest in the mammal.

An "antagonist" is a composition of matter which when administered to a mammal such as a human, inhibits a biological activity attributable to the level or presence of a compound or molecule of interest in the mammal.

As used herein, "alleviating a disease or disorder symptom", means reducing the severity of the symptom or the frequency with which such a symptom is experienced by a patient, or both.

As used herein, amino acids are represented by the full name thereof, by the three letter code corresponding thereto, and/or by the one-letter code corresponding thereto, as summarized in Table 2:

Table 1

Amino Acids and Codes Therefor

| Full Name | 3-Letter Code | 1-Letter Code | Full Name | 3-Letter Code | 1-Letter Code |
|---|---|---|---|---|---|
| Aspartic Acid | Asp | D | Threonine | Thr | T |
| Glutamic Acid | Glu | E | Glycine | Gly | G |
| Lysine | Lys | K | Alanine | Ala | A |
| Arginine | Arg | R | Valine | Val | V |
| Histidine | His | H | Leucine | Leu | L |
| Tyrosine | Tyr | Y | Isoleucine | Ile | I |
| Cysteine | Cys | C | Methionine | Met | M |
| Asparagine | Asn | N | Proline | Pro | P |
| Glutamine | Gln | Q | Phenylalanine | Phe | F |
| Serine | Ser | S | Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to, salts, amino acid derivatives (such as amides), and substitutions. Amino acids contained within the peptides of the presently disclosed subject matter, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the presently disclosed subject matter.

The term "amino acid" is used interchangeably with "amino acid residue", and may refer to a free amino acid and to an amino acid residue of a peptide. It will be apparent from the context in which the term is used whether it refers to a free amino acid or a residue of a peptide.

Amino acids have the following general structure:

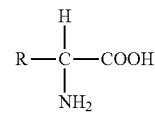

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the presently disclosed subject matter follows the conventional practice wherein the amino group is presented to the left and the carboxy group to the right of each amino acid residue. In the formulae representing selected specific embodiments of the presently disclosed subject matter, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

The term "antagomir" refers to a small RNA or DNA (or chimeric) molecule to antagonize endogenous small RNA regulators like microRNA (miRNA). These antagonists bear complementary nucleotide sequences for the most part, which means that antagomirs should hybridize to the mature microRNA (miRNA). They prevent other molecules from binding to a desired site on an mRNA molecule and are used to silence endogenous microRNA (miR). Antagomirs are therefore designed to block biological activity of these post-transcriptional molecular switches. Like the preferred target ligands (microRNA, miRNA), antagomirs have to cross membranes to enter a cell. Antagomirs also known as anti-miRs or blockmirs.

MicroRNAs are generally about 16-25 nucleotides in length. In some embodiments, miRNAs are RNA molecules of 22 nucleotides or less in length. These molecules have been found to be highly involved in the pathology of several types of cancer. Although the miRNA molecules are generally found to be stable when associated with blood serum and its components after EDTA treatment, introduction of locked nucleic acids (LNAs) to the miRNAs via PCR further increases stability of the miRNAs. LNAs are a class of nucleic acid analogues in which the ribose ring is "locked" by a methylene bridge connecting the 2'-O atom and the 4'-C atom of the ribose ring, which increases the molecule's affinity for other molecules. miRNAs are species of small non-coding single-stranded regulatory RNAs that interact with the 3'-untranslated region (3'-UTR) of target mRNA molecules through partial sequence homology. They participate in regulatory networks as controlling elements that direct comprehensive gene expression. Bioinformatics analysis has predicted that a single miRNA can regulate hundreds of target genes, contributing to the combinational and subtle regulation of numerous genetic pathways.

The term "antimicrobial agents" as used herein refers to any naturally-occurring, synthetic, or semi-synthetic compound or composition or mixture thereof, which is safe for human or animal use as practiced in the methods of this presently disclosed subject matter, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the presently disclosed subject matter include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

The term "autologous", as used herein, refers to something that occurs naturally and normally in a certain type of tissue or in a specific structure of the body.

The term "basal medium", as used herein, refers to a minimum essential type of medium, such as Dulbecco's Modified Eagle's Medium, Ham's F12, Eagle's Medium, RPMI, AR8, etc., to which other ingredients may be added. The term does not exclude media which have been prepared or are intended for specific uses, but which upon modification can be used for other cell types, etc.

The term "biocompatible", as used herein, refers to a material that does not elicit a substantial detrimental response in the host.

The term "biodegradable", as used herein, means capable of being biologically decomposed. A biodegradable material differs from a non-biodegradable material in that a biodegradable material can be biologically decomposed into units which may be either removed from the biological system and/or chemically incorporated into the biological system.

As used herein, the term "fragment" of the polypeptide of the presently disclosed subject matter encompasses natural or synthetic portions of the full-length protein, which in some embodiments are capable of specific or selective binding to their natural ligand or of performing a function of the protein. Truncations, alternatively spliced version, and indeed combition of any natural or synthetic portions of the full-length protein are encompassed by the term "fragment".

The term "biological sample", as used herein, refers to samples obtained from a subject, including, but not limited to, skin, hair, tissue, blood, plasma, cells, sweat and urine.

The term "bioresorbable", as used herein, refers to the ability of a material to be resorbed in vivo. "Full" resorption means that no significant extracellular fragments remain. The resorption process involves elimination of the original implant materials through the action of body fluids, enzymes, or cells. Resorbed calcium carbonate may, for example, be redeposited as bone mineral, or by being otherwise re-utilized within the body, or excreted. "Strongly bioresorbable", as the term is used herein, means that at least 80% of the total mass of material implanted is resorbed within one year.

The terms "cell" and "cell line", as used herein, may be used interchangeably. All of these terms also include their progeny, which are any and all subsequent generations. It is understood that all progeny may not be identical due to deliberate or inadvertent mutations.

The terms "cell culture" and "culture", as used herein, refer to the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture", "organ culture", "organ system culture" or "organotypic culture" may occasionally be used interchangeably with the term "cell culture".

The phrases "cell culture medium", "culture medium" (plural "media" in each case) and "medium formulation" refer to a nutritive solution for cultivating cells and may be used interchangeably.

As used herein, the term "chemically conjugated", or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene comprises the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if when the two regions are arranged in an antiparallel fashion, at least one nucleotide residue of the first region is capable of base pairing with a residue of the second region. In some embodiments, the first region comprises a first portion and the second region comprises a second portion, whereby, when the first and second portions are arranged in an antiparallel fashion, at least about 50%, and in some embodiments at least about 75%, at least about 90%, or at least about 95% of the nucleotide residues of the first portion are capable of base pairing with nucleotide residues in the second portion. More in some embodiments, all nucleotide residues of the first portion are capable of base pairing with nucleotide residues in the second portion.

A "compound", as used herein, refers to any type of substance or agent that is commonly considered a drug, or a candidate for use as a drug, combinations, and mixtures of the above, as well as polypeptides and constructs of the presently disclosed subject matter.

A "computer-readable medium" is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

A "conditioned medium" is one prepared by culturing a first population of cells or tissue in a medium, and then harvesting the medium. The conditioned medium (along with anything secreted into the medium by the cells) may then be used to support the growth or differentiation of a second population of cells.

As used herein, the term "conservative amino acid substitution" is defined herein as an amino acid exchange within one of the five groups summarized in Table 2.

TABLE 2

Conservative Amino Acid Substitutions

| Group | Characteristics | Amino Acids |
|---|---|---|
| A. | Small aliphatic, nonpolar or slightly polar residues | Ala, Ser, Thr, Pro, Gly |
| B. | Polar, negatively charged residues and their amides | Asp, Asn, Glu, Gln |
| C. | Polar, positively charged residues | His, Arg, Lys |
| D. | Large, aliphatic, nonpolar residues | Met Leu, Ile, Val, Cys |
| E. | Large, aromatic residues | Phe, Tyr, Trp |

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A tissue "normally comprises" a cell if one or more of the cell are present in the tissue in an animal not afflicted with a disease or disorder.

"Cytokine", as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

The term "delivery vehicle" refers to any kind of device or material which can be used to deliver cells in vivo or can be added to a composition comprising cells administered to an animal. This includes, but is not limited to, implantable devices, aggregates of cells, matrix materials, gels, etc.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compositions in the form of a combination, such as compositions, the amount of each compositions, when administered in combination with another compositions(s), may be different from when that composition is administered alone. Thus, an effective amount of a combination of composition refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

As used herein, an "essentially pure" preparation of a particular protein or peptide is a preparation wherein at least about 95%, and in some embodiments at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term"fragment", as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, in some embodiments, at least about 100 to about 200 nucleotides, in some embodiments, at least about 200 nucleotides to about 300 nucleotides, yet in some embodiments, at least about 300 to about 350, in some embodiments, at least about 350 nucleotides to about 500 nucleotides, yet in some embodiments, at least about 500 to about 600, in some embodiments, at least about 600 nucleotides to about 620 nucleotides, yet in some embodiments, at least about 620 to about 650, and most in some embodiments, the nucleic acid fragment will be greater than about 650 nucleotides in length.

As used herein, a "functional" biological molecule is a biological molecule in a form in which it exhibits a property by which it is characterized. A functional enzyme, for example, is one which exhibits the characteristic catalytic activity by which the enzyme is characterized.

The term "growth factor" as used herein means a bioactive molecule that promotes the proliferation of a cell or tissue. Growth factors useful in the presently disclosed subject matter include, but are not limited to, transforming growth factor-alpha (TGF-α), transforming growth factor-beta (TGF-β), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor, stem cell factor (SCF), keratinocyte growth factor (KGF), skeletal growth factor, bone matrix derived growth factors, and bone derived growth factors and mixtures thereof. Some growth factors may also promote differentiation of a cell or tissue.

TGF, for example, may promote growth and/or differentiation of a cell or tissue. Note that many factors are pleiotropic in their activity and the activity can vary depending on things such as the cell type being contacted, the state of proliferation or differentiation of the cell, etc.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'-ATTGCC-5' and 3'-TATGGC-5' share 50% homology.

As used herein, "homology" is used synonymously with "identity".

The determination of percent identity between two nucleotide or amino acid sequences can be accomplished using a mathematical algorithm. For example, a mathematical algorithm useful for comparing two sequences is the algorithm of Karlin & Altschul, 1990, modified as in Karlin & Altschul, 1993). This algorithm is incorporated into the NBLAST and XBLAST programs of Altschul et al., 1990, and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al., 1997. Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

The term "ingredient" refers to any compound, whether of chemical or biological origin, that can be used in cell culture media to maintain or promote the proliferation, survival, or differentiation of cells. The terms "component", "nutrient", "supplement", and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "inhibit", as used herein, means to suppress or block an activity or function such that it is lower relative to a control value. The inhibition can be via direct or indirect mechanisms. In some embodiments, the activity is suppressed or blocked by at least 10% compared to a control value, more in some embodiments by at least 25%, and in some embodiments by at least 50%.

The term "inhibitor" as used herein, refers to any compound or agent, the application of which results in the inhibition of a process or function of interest, including, but not limited to, expression, levels, and activity. Inhibition can be inferred if there is a reduction in the activity or function of interest. The term "modulator" encompasses the term "inhibitor".

The term "inhibit a complex", as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time. The term "modulate a complex" encompasses the term "inhibit a complex".

The term "inhibit a protein", as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound or cells of the presently disclosed subject matter by any number of routes and approaches including, but not limited to, intravitreal, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

The term "injury" refers to any physical damage to the body caused by violence, accident, trauma, or fracture, etc., as well as damage by surgery.

As used herein, an "instructional material" includes a publication, a recording, a diagram, or any other medium of expression which can be used to communicate the usefulness of the peptide of the presently disclosed subject matter in the kit for effecting alleviation of the various diseases or disorders recited herein. Optionally, or alternately, the instructional material may describe one or more methods of alleviating the diseases or disorders in a cell or a tissue of a vertebrate subject, such as a mammal. The instructional material of the kit of the presently disclosed subject matter may, for example, be affixed to a container which contains the identified compound presently disclosed subject matter or be shipped together with a container which contains the identified compound. Alternatively, the instructional material may be shipped separately from the container with the intention that the instructional material and the compound be used cooperatively by the recipient.

Used interchangeably herein are the terms: 1) "isolate" and "select"; and 2)"detect" and "identify".

The term "isolated", when used in reference to compositions and cells, refers to a particular composition or cell of interest, or population of cells of interest, at least partially isolated from other cell types or other cellular material with which it naturally occurs in the tissue of origin. A composition or cell sample is "substantially pure" when it is at least 60%, or at least 75%, or at least 90%, and, in certain cases, at least 99% free of materials, compositions, cells other than composition or cells of interest. Purity can be measured by any appropriate method, for example, by fluorescence-activated cell sorting (FACS), or other assays which distinguish cell types. Representative isolation techniques are disclosed herein for antibodies and fragments thereof.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, a "ligand" is a compound that specifically or selectively binds to a target compound. A ligand (e.g., an antibody or peptide sequence) "specifically binds to", "is specifically immunoreactive with", "having a selective binding activity", "selectively binds to" or "is selectively immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically or selectively binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal anti-bodies specifically immunoreactive with an antigen. See Harlow & Lane, 1988, for a description of immunoassay formats and conditions that can be used to determine specific immunoreactivity.

A "receptor" is a compound that specifically or selectively binds to a ligand.

A ligand or a receptor (e.g., an antibody or peptide sequence)"specifically binds to", "is specifically immunoreactive with", "having a selective binding activity", "selectively binds to" or "is selectively immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically or selectively binds under hybridization conditions to a compound polynucleotide comprising a complementary sequence; an antibody specifically or selectively binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow & Lane 1988 for a description of immunoassay formats and conditions that can be used to determine specific or selective immunoreactivity. See also the EXAMPLES set forth herein below for additional formats and conditions that can be used to determine specific or selective immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

Micro-RNAs are generally about 16-25 nucleotides in length. In some embodiments, miRNAs are RNA molecules of 22 nucleotides or less in length. These molecules have been found to be highly involved in the pathology of several types of cancer. Although the miRNA molecules are generally found to be stable when associated with blood serum and its components after EDTA treatment, introduction of locked nucleic acids (LNAs) to the miRNAs via PCR further increases stability of the miRNAs. LNAs are a class of nucleic acid analogues in which the ribose ring is "locked" by a methylene bridge connecting the 2'-O atom and the 4'-C atom of the ribose ring, which increases the molecule's affinity for other molecules. miRNAs are species of small non-coding single-stranded regulatory RNAs that interact with the 3'-untranslated region (3'-UTR) of target mRNA molecules through partial sequence homology. They participate in regulatory networks as controlling elements that direct comprehensive gene expression. Bioinformatics analysis has predicted that a single miRNA can regulate hundreds of target genes, contributing to the combinational and subtle regulation of numerous genetic pathways.

The term "modulate", as used herein, refers to changing the level of an activity, function, or process. The term "modulate" encompasses both inhibiting and stimulating an activity, function, or process. The term "modulate" is used interchangeably with the term "regulate" herein. By "modulate" is intended an increase, decrease, or other alteration of any or all biological activities or properties of LEMD3. A composition that has an ability to modulate LEMD3 biological activity has utility in the treatment of disorders and conditions associated with the biological activity of LEMD3, including modulating transforming growth factor-beta (TGFβ) biological activity.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil).

As used herein, the term "nucleic acid" encompasses RNA as well as single and double-stranded DNA and cDNA. Furthermore, the terms, "nucleic acid", "DNA", "RNA" and similar terms also include nucleic acid analogs, i.e. analogs having other than a phosphodiester backbone. For example, the so-called "peptide nucleic acids", which are known in the art and have peptide bonds instead of phosphodiester bonds in the backbone, are considered within the scope of the presently disclosed subject matter. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences".

The term "nucleic acid construct", as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T".

The term "otherwise identical sample", as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample. By analogy, the term "otherwise identical" can also be used regarding regions or tissues in a subject or in an unaffected subject.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of cells, a drug, or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "physiologically acceptable" ester or salt means an ester or salt form of the active ingredient which is compatible with any other ingredients of the pharmaceutical composition, which is not deleterious to the subject to which the composition is to be administered.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

The term "prevent", as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

The term "propagate" means to reproduce or to generate.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross & Mienhofer, 1981 for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl, or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. Representative purification techniques are disclosed herein for antibodies and fragments thereof.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell". A gene which is expressed in a recombinant host cell wherein the gene comprises a recombinant polynucleotide, produces a "recombinant polypeptide".

A "recombinant polypeptide" is one which is produced upon expression of a recombinant polynucleotide.

The term "regulate" refers to either stimulating or inhibiting a function or activity of interest.

As used herein, term "regulatory elements" is used interchangeably with "regulatory sequences" and refers to promoters, enhancers, and other expression control elements, or any combination of such elements.

A "sample", as used herein, refers in some embodiments to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In some embodiments, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

The term "standard", as used herein, refers to something used for comparison. For example, a standard can be a known standard agent or compound which is administered or added to a control sample and used for comparing results when measuring said compound in a test sample. Standard can also refer to an "internal standard", such as an agent or compound which is added at known amounts to a sample and is useful in determining such things as purification or recovery rates when a sample is processed or subjected to purification or extraction procedures before a marker of interest is measured.

The term "stimulate" as used herein, means to induce or increase an activity or function level such that it is higher relative to a control value. The stimulation can be via direct or indirect mechanisms. In some embodiments, the activity or function is stimulated by at least 10% compared to a control value, more in some embodiments by at least 25%, and in some embodiments by at least 50%.

The term "stimulator" as used herein, refers to any composition, compound or agent, the application of which results in the stimulation of a process or function of interest.

A "subject" of diagnosis or treatment is an animal, including a human. It also includes pets and livestock.

As used herein, a "subject in need thereof" is a patient, animal, mammal, or human, who will benefit from the method of this presently disclosed subject matter.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "substantially homologous amino acid sequences" includes those amino acid sequences which have at least about 95% homology, in some embodiments at least about 96% homology, more in some embodiments at least about 97% homology, in some embodiments at least about 98% homology, and most in some embodiments at least about 99% or more homology to an amino acid sequence of a reference sequence. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the presently disclosed subject matter.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. In some embodiments, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M NaPO4, 1 mM EDTA at 50° C. with washing in 2× standard saline citrate (SSC), 0.1% SDS at 50° C.; in some embodiments in 7% (SDS), 0.5 M NaPO4, 1 mM EDTA at 50° C. with washing in 1×SSC, 0.1% SDS at 50° C.; in some embodiments 7% SDS, 0.5 M NaPO4, 1 mM EDTA at 50° C. with washing in 0.5×SSC, 0.1% SDS at 50° C.; and more in some embodiments in 7% SDS, 0.5 M NaPO4, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984), and the BLASTN or FASTA programs (Altschul et al., 1990a; Altschul et al., 1990b; Altschul et al., 1997). The default settings provided with these programs are suitable for determining substantial similarity of nucleic acid sequences for purposes of the presently disclosed subject matter.

The term "substantially pure" describes a compound, e.g., a protein or polypeptide which has been separated from components which naturally accompany it. Typically, a compound is substantially pure when at least 10%, more in some embodiments at least 20%, more in some embodiments at least 50%, more in some embodiments at least 60%, more in some embodiments at least 75%, more in some embodiments at least 90%, and most in some embodiments at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

A "surface active agent" or "surfactant" is a substance that has the ability to reduce the surface tension of materials and enable penetration into and through materials.

The term "symptom", as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The use of the phrase "tissue culture dish or plate" refers to any type of vessel which can be used to plate cells for growth or differentiation.

"Tissue" means (1) a group of similar cells united to perform a specific function; (2) a part of an organism consisting of an aggregate of cells having a similar structure and function; or (3) a grouping of cells that are similarly characterized by their structure and function, such as muscle or nerve tissue.

The term "topical application", as used herein, refers to administration to a surface, such as the skin. This term is used interchangeably with "cutaneous application" in the case of skin. A "topical application" is a "direct application".

By "transdermal" delivery is meant delivery by passage of a drug through the skin or mucosal tissue and into the bloodstream. Transdermal also refers to the skin as a portal for the administration of drugs or compounds by topical application of the drug or compound thereto. "Transdermal" is used interchangeably with "percutaneous".

The term "transfection" is used interchangeably with the terms "gene transfer", "transformation", and "transduction", and means the intracellular introduction of a polynucleotide. "Transfection efficiency" refers to the relative amount of the transgene taken up by the cells subjected to transfection. In practice, transfection efficiency is estimated by the amount of the reporter gene product expressed following the transfection procedure.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat", as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein, the term "wound" relates to a physical tear, break, or rupture to a tissue or cell layer. A wound may occur by any physical insult, including a surgical procedure or as a result of a disease, disorder condition.

Methods useful for the practice of the presently disclosed subject matter which are not described herein are also known in the art. Useful methods include those described in PCT International Patent Application Publication Nos. WO 2007/019107; WO 2007/030652; WO 2007/089798; WO 2008/060374, the methods of which are hereby incorporated by reference.

III. EXEMPLARY EMBODIMENTS

The presently disclosed subject matter also provides in some embodiments methods and compositions for treating diseases and/or disorders in subjects. Reference is made to the Examples as set forth herein below for exemplary diseases and disorders.

In some embodiments, the presently disclosed subject matter provides compositions and methods useful for modulating transforming growth factor-beta (TGFβ) biological activity in a vertebrate subject in need thereof. In some embodiments, the presently disclosed methods comprise administering to the vertebrate subject an effective amount of a substance capable of modulating activity of LEMD3 in the vertebrate subject to thereby modulate TGFβ biological activity in the vertebrate subject. In some embodiments, the vertebrate subject is suffering from fibrosis, including but not limited to pulmonary fibrosis, such as but not limited to IPF. In some embodiments, the subject is a mammal.

In some embodiments, the presently disclosed subject matter provides a method of treating fibrosis in a vertebrate subject in need thereof. In some embodiments, the method comprises the step of administering to the vertebrate subject an effective amount of a substance capable of modulating activity of LEMD3 in the vertebrate subject. In some embodiments, the subject is a mammal. In some embodiments, the fibrosis is pulmonary fibrosis, such as but not limited to IPF.

By "modulate" is intended an increase, decrease, or other alteration of any or all biological activities or properties of a biochemical entity, such as LEMD3. Increasing a biological property can include increasing a level of LEMD3.

In some embodiments, the substance that modulates the LEMD3 activity comprises a LEMD3 polypeptide. That is, a LEMD3 polypeptide modulates in vivo LEMD3 biological activity by providing LEMD3 biological activity such as by increasing a level of LEMD3 polypeptide in vivo.

In some embodiments, the step of administering further comprises administering an effective amount of a substance that modulates expression of LEMD3-encoding nucleic acid molecule in the vertebrate subject. In some embodiments, the substance that modulates expression of a LEMD3-encoding nucleic acid molecule comprises an effective amount of a siRNA, a vector encoding the siRNA, or combinations thereof. Representative siRNAs are disclosed in SEQ ID NOs:1-4. Antisense oligonucleotide-based approaches and miRNA-based approaches can also be employed.

In some embodiments, the step of administering further comprises administering to the vertebrate subject a construct comprising a nucleic acid sequence encoding a LEMD3 polypeptide operatively linked to a promoter, wherein production of the LEMD3 polypeptide in the subject results in modulation of TGFβ biological activity. In some embodiments, the LEMD3 polypeptide is overexpressed. In some embodiments, the construct further comprises a vector selected from the group consisting of a plasmid vector and a viral vector. In some embodiments, the construct further comprises a liposome complex.

In some embodiments, the LEMD3 polypeptide comprises a polypeptide having an amino acid sequence as set forth in SEQ ID NO:24, which is the full length amino acid sequence of LEMD3. In some embodiments, fragments and homologs of SEQ ID NO:24 are provided. In some embodiments, the fragment or homolog is derived from the C-terminal or N-terminal end of a LEMD3 polypeptide. In some embodiments, a fragment or homolog comprises the RRM domain of LEMD3, which set forth in SEQ ID NO:29, as this sequence contributes to binding and sequestering of the deleterious SMADs. In some embodiments, a LEMD3 polypeptide comprises a fragment or homolog of SEQ ID NO: 29.

In some embodiments, a representative C-terminal LEMD3 fragment (CTF) comprises SEQ ID NO: 25. This representative CTF fragment comprises 20 N-terminal amino acids and the RRM domain (SEQ ID NO: 29), except that the initial valine (V) of the RRM domain is omitted. In some embodiments, fragments and homologs of SEQ ID NO:25 are provided. In some embodiments, the fragment or homolog is derived from the C-terminal or N-terminal end of a LEMD3 polypeptide of SEQ ID NO: 25. In some embodiments, a fragment or homolog comprises the RRM domain of LEMD3, which set forth in SEQ ID NO:29, or a fragment or homolog of SEQ ID NO: 29.

In some embodiments, the nucleic acid sequence is selected from the group consisting of (a) a nucleic acid sequence encoding a polypeptide having an amino acid sequence as set forth in SEQ ID NOs: 24, 25, or 29, or a fragment or homolog thereof (b) a nucleic acid sequence as set forth in any of SEQ ID NOs: 26 (nucleic acid sequence encoding full length LEMD3), 27 (nucleic acid sequence encoding LEMD3 CTF of SEQ ID NO:25), or 28 ((nucleic acid sequence encoding RRM domain of LEMD3 as set forth in SEQ ID NO: 29), or its complementary strands; (c) a homologous nucleic acid sequence to a nucleic acid sequence as set forth in any of SEQ ID NOs:26, 27, or 28, and which encodes a LEMD3 polypeptide; and (d) a nucleic acid sequence differing from an isolated nucleic acid molecule of (a), (b), or (c) above due to degeneracy of the genetic code, and which encodes a LEMD3 polypeptide encoded by the isolated nucleic acid molecule of (a), (b), or (c) above.

In some embodiments, the presently disclosed subject matter provides a composition comprising a substance capable of modulating activity of LEMD3 in a vertebrate subject. In some embodiments, the substance is selected from the group consisting of (a) a LEMD3 polypeptide; (b) an effective amount of a siRNA that modulates expression of a LEMD3-encoding nucleic acid molecule, a vector encoding the siRNA, or combinations thereof; and (c) a construct comprising a nucleic acid sequence encoding a LEMD3 polypeptide operatively linked to a promoter.

In some embodiments, the LEMD3 polypeptide comprises a polypeptide having an amino acid sequence as set forth in SEQ ID NO:24, which is the full length amino acid sequence of LEMD3. In some embodiments, fragments and homologs of SEQ ID NO:24 are provided. In some embodiments, the fragment or homolog is derived from the C-terminal or N-terminal end of a LEMD3 polypeptide. In some embodiments, a fragment or homolog comprises the RRM domain of LEMD3, which set forth in SEQ ID NO:29, as this sequence contributes to binding and sequestering of the deleterious SMADs. In some embodiments, a LEMD3 polypeptide comprises a fragment or homolog of SEQ ID NO: 29.

In some embodiments, a representative C-terminal LEMD3 fragment (CTF) comprises SEQ ID NO: 25. This representative CTF fragment comprises 20 N-terminal amino acids and the RRM domain (SEQ ID NO: 29), except that the initial valine (V) of the RRM domain is omitted. In some embodiments, fragments and homologs of SEQ ID NO:25 are provided. In some embodiments, the fragment or homolog is derived from the C-terminal or N-terminal end of a LEMD3 polypeptide of SEQ ID NO: 25. In some embodiments, a fragment or homolog comprises the RRM domain of LEMD3, which set forth in SEQ ID NO:29, or a fragment or homolog of SEQ ID NO: 29.

In some embodiments, the nucleic acid sequence is selected from the group consisting of (a) a nucleic acid sequence encoding a polypeptide having an amino acid sequence as set forth in SEQ ID NOs: 24, 25, or 29, or a fragment or homolog thereof, (b) a nucleic acid sequence as set forth in any of SEQ ID NOs: 26 (nucleic acid sequence encoding full length LEMD3), 27 (nucleic acid sequence encoding LEMD3 CTF of SEQ ID NO:25), or 28 ((nucleic acid sequence encoding RRM domain of LEMD3 as set forth in SEQ ID NO: 29), or its complementary strands; (c)

a homologous nucleic acid sequence to a nucleic acid sequence as set forth in any of SEQ ID NOs:26, 27, or 28, and which encodes a LEMD3 polypeptide; and (d) a nucleic acid sequence differing from an isolated nucleic acid molecule of (a), (b), or (c) above due to degeneracy of the genetic code, and which encodes a LEMD3 polypeptide encoded by the isolated nucleic acid molecule of (a), (b), or (c) above. In some embodiments, the vector encoding the siRNA comprises: a promoter operatively linked to a nucleic acid molecule encoding the siRNA molecule; and a transcription termination sequence. Representative siRNAs are disclosed in SEQ ID NOs:1-4. Antisense oligonucleotide-based approaches and miRNA based approaches can also be employed.

The presently disclosed subject matter provides LEMD3 polypeptides and biologically active fragments and homologs thereof as well as methods for preparing and testing new polypeptides for the properties disclosed herein. In some embodiments, the fragments are mammalian. In some embodiments, the fragments are human.

In some embodiments, a LEMD3 polypeptide or biologically active fragment or homolog thereof is useful for treating a disease or disorder associated with the TGFβ pathway disclosed herein. In some embodiments, the pathway involves Smad2/3.

In some embodiments, the presently disclosed subject matter uses a biologically active LEMD3 polypeptide or biologically active fragment or homolog thereof. In some embodiments, the isolated polypeptide comprises a mammalian molecule at least about 30% homologous to a polypeptide having the amino acid sequence of at least one of the sequences disclosed herein. In some embodiments, the isolated polypeptide is at least about 35% homologous, more in some embodiments, about 40% homologous, more in some embodiments, about 45% homologous, in some embodiments, about 50% homologous, more in some embodiments, about 55% homologous, in some embodiments, about 60% homologous, more in some embodiments, about 65% homologous, in some embodiments, more in some embodiments, about 70% homologous, more in some embodiments, about 75% homologous, in some embodiments, about 80% homologous, more in some embodiments, about 85% homologous, more in some embodiments, about 90% homologous, in some embodiments, about 95% homologous, more in some embodiments, about 96% homologous, more in some embodiments, about 97% homologous, more in some embodiments, about 98% homologous, and most in some embodiments, about 99% homologous to at least one of the peptide sequences disclosed herein.

The presently disclosed subject matter further encompasses modification of the LEMD3 and fragments thereof disclosed herein, including amino acid deletions, additions, and substitutions, particularly conservative substitutions. The presently disclosed subject matter also encompasses modifications to increase in vivo half-life and decrease degradation in vivo. Substitutions, additions, and deletions can include, for example, 1, 2, 3, 4, 5, 6, 7, 8, 9, 10, 11, 12, 13, 14, 15, 16, 17, 18, 19, 20, 21, 22, 23, 24, and 25 changes as long as the activity disclosed herein remains substantially the same.

The presently disclosed subject matter includes an isolated nucleic acid comprising a nucleic acid sequence encoding a LEMD3 polypeptide of the presently disclosed subject matter, or a fragment or homolog thereof. In some embodiments, the nucleic acid sequence encodes a peptide comprising a LEMD3 polypeptide sequence of the presently disclosed subject matter, or a biologically active fragment of homolog thereof.

In some embodiments, a homolog of a polypeptide (full length or fragment) of the presently disclosed subject matter is one with one or more amino acid substitutions, deletions, or additions, and with the sequence identities described herein. In some embodiments, the substitution, deletion, or addition is conservative.

In some embodiments, the subject is a mammal. In some embodiments, the mammal is a human.

The presently disclosed subject matter encompasses the use of purified isolated, recombinant, and synthetic polypeptides. The presently disclosed subject matter also provides in some embodiments recombinant nucleic acids and substantially homologous nucleic acid sequences thereto. In some embodiments, the peptide or nucleic acid is present in the pharmacologically acceptable carrier. In some embodiments, the presently disclosed polypeptides, fragments, and homologs thereof can comprise a tag sequence, linker sequence, spacer sequence and/or other additional sequence that can be used in to facilitate expression, stability, purification, isolation, or other desired feature or aspect. Multiple copies of such sequences can be employed. Such sequences can be added to the N-terminus, the C-terminus, or both of a polypeptide, fragment, or homolog thereof of the presently disclosed subject matter.

One of ordinary skill in the art will appreciate that based on the sequences of the components of the LEMD3 polypeptides disclosed herein they can be modified independently of one another with conservative amino acid changes, including, insertions, deletions, and substitutions.

In some embodiments, a composition (e.g., comprising a polypeptide, fragment thereof, construct, and/or vector) of the presently disclosed subject matter, or a combination thereof, can be administered by a route selected from, including, but not limited to, intravenously, intrathecally, locally, intramuscularly, topically, orally, intra-arterially, parenterally, etc. Administration can be more than once. One of ordinary skill in the art can determine how often to administer the compound, the dose to be used, and what combination of other agents it can be administered with such as therapeutic agents and/or other drugs or compounds such as antimicrobial agents, anti-inflammatory agents, etc. One of ordinary skill in the will be able to determine when or if to use an additional agent and the route of administration.

In some embodiments, the present compostions are administered by injection. The parenteral route for administration of the composition is in accordance with known methods, e.g., injection or infusion by intravenous, intraperitoneal, intramuscular, intra-arterial, subcutaneous, or intralesional routes. The composition may be administered continuously by infusion or by bolus injection. A typical composition for intravenous infusion could be made up to contain 10 to 50 ml of sterile 0.9% NaCl or 5% glucose optionally supplemented with a 20% albumin solution and between 10 ug and 50 mg, in some embodiments between 50 ug and 10 mg, of a composition of the presently disclosed subject matter. A typical pharmaceutical composition for intramuscular injection would be made up to contain, for example, 1-10 ml of sterile buffered water and between 10 ug and 50 mg, in some embodiments between 50 ug and 10 mg, of the composition of the presently disclosed subject matter. Methods for preparing parenterally administrable compositions are well known in the art and described in more detail in various sources, including, for example, Genaro 1985, which is incorporated herein by reference in its entirety for all purposes.

When used in vivo for therapy, the compositions of the subject presently disclosed subject matter are administered to the subject in therapeutically effective amounts (i.e., amounts that have desired therapeutic effect). They will normally be administered parenterally. The dose and dosage regimen will depend upon the degree of the disease or disorder, the characteristics of the particular composition used, e.g., its therapeutic index, the patient, and the patient's history. Advantageously the composition is administered continuously over a period of 1-2 weeks. Optionally, the administration is made during the course of adjunct therapy such as antimicrobial treatment, or administration of tumor necrosis factor, interferon, or other cytoprotective or immunomodulatory agent.

For parenteral administration, the composition will be formulated in a unit dosage injectable form (solution, suspension, emulsion) in association with a pharmaceutically acceptable parenteral vehicle. Such vehicles are inherently nontoxic, and non-therapeutic. Examples of such vehicle are water, saline, Ringer's solution, dextrose solution, and 5% human serum albumin. Nonaqueous vehicles such as fixed oils and ethyl oleate can also be used. Liposomes can be used as carriers. The vehicle can contain minor amounts of additives such as substances that enhance isotonicity and chemical stability, e.g., buffers and preservatives. The compositions will typically be formulated in such vehicles at concentrations of about 1.0 mg/ml to about 10 mg/ml.

The compositions used are formulated and dosages established in a fashion consistent with good medical practice taking into account the condition or disorder to be treated, the condition of the individual patient, the site of delivery of the composition, the method of administration, and other factors known to practitioners. The compositions are prepared for administration according to the description of preparation for administration, infra.

The polypeptides of the presently disclosed subject matter may be readily prepared by standard, well-established techniques, such as solid-phase peptide synthesis (SPPS) as described by Stewart et al., 1984; Bodanszky & Bodanszky, 1984. At the outset, a suitably protected amino acid residue is attached through its carboxyl group to a derivatized, insoluble polymeric support, such as cross-linked polystyrene or polyamide resin.

"Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions that will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method that utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

To ensure that the proteins or peptides obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic or other assay is used to monitor purification at each stage in the procedure. Protein purification methods are well known in the art, and are described, for example in Deutscher et al. 1990.

Peptide Modification and Preparation

Peptide preparation is described in the Examples. It will be appreciated, of course, that the proteins or peptides of the presently disclosed subject matter may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include C1-C5 branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines ($—NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Acid addition salts of the presently disclosed subject matter are also contemplated as functional equivalents. Thus, a peptide in accordance with the presently disclosed subject matter treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the presently disclosed subject matter.

The presently disclosed subject matter also provides for analogs of proteins. Analogs can differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. To that end, 10 or more conservative amino acid changes typically have no effect on peptide function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the presently disclosed subject matter are not limited to products of any of the specific exemplary processes listed herein.

The presently disclosed subject matter includes the use of beta-alanine (also referred to as β-alanine, β-Ala, bA, and βA, having the structure:

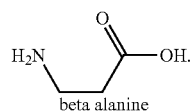
beta alanine

Sequences are provided herein which use the symbol "βA", but in the Sequence Listing submitted herewith "βA" is provided as "Xaa" and reference in the text of the Sequence Listing indicates that Xaa is beta alanine.

It will be appreciated, of course, that the polypeptides, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

S Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include C1-C5 branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—NH2), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the presently disclosed subject matter are also contemplated, for example, inverted peptides in which all amino acids are substituted with D-amino acid forms.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al., 1990.

As discussed, modifications or optimizations of peptide ligands of the presently disclosed subject matter are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Amino Acid Substitutions

In certain embodiments, the disclosed methods and compositions may involve preparing polypeptides with one or more substituted amino acid residues.

In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the presently disclosed subject matter are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, one can make the following isosteric and/or conservative amino acid changes in the parent polypeptide sequence with the expectation that the resulting polypeptides would have a similar or improved profile of the properties described above: Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from C1-C10 branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see e.g., Chou & Fasman, 1974, Biochemistry, 13:222-245; 1978, Arm. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser, Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr, Tyr and Trp. (See e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser, Ala and Lys; Ser and Thr; Lys and Arg; Val and Leu; Leu and Ile; Ile and Val; Phe and Tyr. Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

Gene Therapy Formats and Preparation Thereof

Gene therapy constructs against proteins, polypeptides, or peptide fragments thereof of the presently disclosed subject matter may be generated using methods that are well known in the art. By way of example and not limitation, LEMD3 genes can be used for gene therapy in accordance with the presently disclosed subject matter. Exemplary gene therapy methods are described in U.S. Patent Publication Nos. US20190000991A1 and US20190008909A1, the contents of each of which are herein incorporated by reference.

Briefly, gene therapy directed toward modulation of LEMD3 levels, to thereby affect or modulate the biological activity of TGFβ in a target cell or tissue is described. In some embodiments, a therapeutic method of the presently disclosed subject matter a process for modulation of LEMD3 levels comprising the steps of: (a) delivering to the cell an effective amount of a DNA molecule comprising a polynucleotide that encodes a polypeptide that modulates the biological activity of LEMD3; and (b) maintaining the cell under conditions sufficient for expression of said polypeptide.

In accordance with the presently disclosed subject matter a LEMD3 gene sequence itself is employed to introduce a LEMD3 gene product, a convenient method of introduction will be through the use of a recombinant vector that incorporates the desired gene, together with its associated control sequences. The preparation of recombinant vectors is well known to those of skill in the art and described in many references, such as, for example, Green et al., eds. (2014) *Molecular Cloning: A Laboratory Manual*, Cold Spring Harbor Laboratory Press, Cold Spring Harbor, N.Y., incorporated herein in its entirety.

It is understood that the DNA coding sequences to be expressed, in this case those encoding the LEMD3 gene products, are positioned in a vector adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter.

Thus, a promoter is a region of a DNA molecule typically within about 100 nucleotide pairs upstream of (i.e., 5' to) the point at which transcription begins (i.e., a transcription start site). That region typically contains several types of DNA sequence elements that are located in similar relative positions in different genes. Another type of discrete transcription regulatory sequence element is an enhancer. An enhancer imposes specificity of time, location and expression level on a particular coding region or gene. A major function of an enhancer is to increase the level of transcription of a coding sequence in a cell that contains one or more transcription factors that bind to that enhancer. An enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Approaches for operatively linking an enhancer-promoter to a coding sequence are well known in the art; the precise orientation and location relative to a coding sequence of interest is dependent, inter alia, upon the specific nature of the enhancer-promoter. An enhancer-promoter used in a vector construct of the presently disclosed subject matter can be any enhancer-promoter that drives expression in a cell to be transfected. By employing an enhancer-promoter with well-known properties, the level and pattern of gene product expression can be optimized.

For introduction of, for example, a human LEMD3 gene, a vector construct that will deliver the gene to the affected cells is desired. Viral vectors can be used. These vectors can be an adenoviral, a retroviral, a vaccinia viral vector, adeno-associated virus, or lentivirus; these vectors are preferred because they have been successfully used to deliver desired sequences to cells and tend to have a high infection efficiency. Suitable vector-LEMD3 gene constructs are adapted for administration as pharmaceutical compositions, as described herein below. Viral promoters can also be of use in vectors of the presently disclosed subject matter, and are known in the art.

Upon a review of the instant disclosure, a therapeutically effective amount of a gene of interest is well within the reach of the skilled person. By way example with regard to dosing of adenoviral vectors, a representative dosage corresponds to at least $1 \times 10^{12}$ capsids/kg of body weight, at least $5 \times 10^{12}$ capsids/kg of body weight, or at least $1 \times 10^{13}$ capsids/kg of body weight. AAV Quantification of AAV capsid particle titers is easily determined and is well known in the art (i.a. Kohlbrenner et al., Hum Gene Ther Meth. June 2012, Vol. 23, No. 3: 198-203; Grimm et al., Gene Ther., Vol. 6, Nr. 7, p, 1322-1330, 1999).

Pharmaceutical Compositions and Administration

The presently disclosed subject matter is also directed to methods of administering the compounds of the presently disclosed subject matter to a subject.

Pharmaceutical compositions comprising the present compounds are administered to a subject in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal approaches.

In accordance with one embodiment, a method of treating a subject in need of such treatment is provided. The method comprises administering a pharmaceutical composition comprising at least one composition of the presently disclosed subject matter to a subject in need thereof. Compositions provided by the methods of the presently disclosed subject matter can be administered with known compounds or other medications as well.

The pharmaceutical compositions useful for practicing the presently disclosed subject matter may be administered to deliver a dose of between 1 ng/kg/day and 100 mg/kg/day.

The presently disclosed subject matter encompasses the preparation and use of pharmaceutical compositions comprising a compound useful for treatment of the diseases and disorders disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The compositions of the presently disclosed subject matter may comprise at least one active polypeptide, one or more acceptable carriers, and optionally other polypeptides or therapeutic agents.

For in vivo applications, the compositions of the presently disclosed subject matter may comprise a pharmaceutically acceptable salt. Suitable acids which are capable of forming such salts with the compounds of the presently disclosed subject matter include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, anthranilic acid, cinnamic acid, naphthalene sulfonic acid, sulfanilic acid and the like.

Pharmaceutically acceptable carriers include physiologically tolerable or acceptable diluents, excipients, solvents, or adjuvants. The compositions are in some embodiments sterile and nonpyrogenic. Examples of suitable carriers include, but are not limited to, water, normal saline, dextrose, mannitol, lactose or other sugars, lecithin, albumin, sodium glutamate, cysteine hydrochloride, ethanol, polyols (propylene glycol, polyethylene glycol, glycerol, and the like), vegetable oils (such as olive oil), injectable organic esters such as ethyl oleate, ethoxylated isostearyl alcohols, polyoxyethylene sorbitol and sorbitan esters, microcrystalline cellulose, aluminum methahydroxide, bentonite, kaolin, agar-agar and tragacanth, or mixtures of these substances, and the like.

The pharmaceutical compositions may also contain minor amounts of nontoxic auxiliary pharmaceutical substances or excipients and/or additives, such as wetting agents, emulsifying agents, pH buffering agents, antibacterial and antifungal agents (such as parabens, chlorobutanol, phenol, sorbic acid, and the like). Suitable additives include, but are not limited to, physiologically biocompatible buffers (e.g., tromethamine hydrochloride), additions (e.g., 0.01 to 10 mole percent) of chelants (such as, for example, DTPA or DTPA-bisamide) or calcium chelate complexes (as for example calcium DTPA or CaNaDTPA-bisamide), or, optionally, additions (e.g., 1 to 50 mole percent) of calcium or sodium salts (for example, calcium chloride, calcium ascorbate, calcium gluconate or calcium lactate). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions. Pharmaceutical compositions according to the presently disclosed subject matter can be prepared in a manner fully within the skill of the art.

The compositions of the presently disclosed subject matter or pharmaceutical compositions comprising these compositions may be administered so that the compositions may have a physiological effect. Administration may occur enterally or parenterally; for example, orally, rectally, intracisternally, intravaginally, intraperitoneally, locally (e.g., with powders, ointments or drops), or as a buccal or nasal spray or aerosol. Parenteral administration is an approach. Particular parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, and direct application to the target area, for example by a catheter or other placement device.

Where the administration of the composition is by injection or direct application, the injection or direct application may be in a single dose or in multiple doses. Where the administration of the compound is by infusion, the infusion may be a single sustained dose over a prolonged period of time or multiple infusions.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the presently disclosed subject matter is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

A pharmaceutical composition of the presently disclosed subject matter may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the presently disclosed subject matter will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the presently disclosed subject matter may further comprise one or more additional pharmaceutically active agents. Particularly contemplated additional agents include anti-emetics and scavengers such as cyanide and cyanate scavengers.

Controlled- or sustained-release formulations of a pharmaceutical composition of the presently disclosed subject matter may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the presently disclosed subject matter are known in the art and described, for example in Genaro, 1985, which is incorporated herein by reference.

Typically, dosages of the compound of the presently disclosed subject matter which may be administered to an animal, in some embodiments a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. In some embodiments, the dosage of the compound will vary from about 1 mg to about 10 g per kilogram of body weight of the animal. In another aspect, the dosage will vary from about 10 mg to about 1 g per kilogram of body weight of the animal.

The compositions may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type of cancer being diagnosed, the type and severity of the condition or disease being treated, the type and age of the animal, etc.

Suitable preparations include injectables, either as liquid solutions or suspensions, however, solid forms suitable for solution in, suspension in, liquid prior to injection, may also be prepared. The preparation may also be emulsified, or the compositions encapsulated in liposomes. The active ingredients are often mixed with excipients which are pharmaceutically acceptable and compatible with the active ingredient. Suitable excipients are, for example, water saline, dextrose, glycerol, ethanol, or the like and combinations thereof. In addition, if desired, the preparation may also include minor amounts of auxiliary substances such as wetting or emulsifying agents, pH buffering agents, and/or adjuvants.

The presently disclosed subject matter also includes a kit comprising the composition of the presently disclosed subject matter and an instructional material which describes adventitially administering the composition to a cell or a tissue of a subject. In some embodiments, this kit comprises a (in some embodiments sterile) solvent suitable for dissolving or suspending the composition of the presently disclosed subject matter prior to administering the compound to the subject and/or a device suitable for administering the composition such as a syringe, injector, or the like or other device as would be apparent to one of ordinary skill in the art upon a review of the instant disclosure.

As used herein, an "instructional material" includes a publication, a recording, a diagram, or any other medium of expression which can be used to communicate the usefulness of the peptide of the presently disclosed subject matter in the kit for effecting alleviation of the various diseases or disorders recited herein. Optionally, or alternately, the instructional material may describe one or more methods of using the compositions for diagnostic or identification purposes or of alleviation the diseases or disorders in a cell or a tissue of a mammal. The instructional material of the kit of the presently disclosed subject matter may, for example, be affixed to a container which contains the multimeric peptide of the presently disclosed subject matter or be shipped together with a container which contains the peptide. Alternatively, the instructional material may be shipped separately from the container with the intention that the instructional material and the composition be used cooperatively by the recipient.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Experimental Procedures for Examples

Primary Fibroblast Cultures and Transfection, Human Lung Biopsies, and Other Reagents—Primary human foreskin fibroblasts (HFFs) were procured from ATCC (ATCC SCRC-1041, ATCC, Manassas, Va.) and routinely cultured in DMEM (ThermoFisher, Waltham, Mass.) supplemented with 15% FBS and 1% penicillin/streptomycin (ThermoFisher, Waltham, Mass.) in 5% $CO_2$ at 37 C in a humified incubator to passage (13). CCL210s, a primary human pulmonary fibroblast line, were procured from ATCC (ATCC CCD-19Lu, ATCC, Manassas, Va.) and routinely cultured in EMEM (ThermoFisher, Waltham, Mass.) supplemented with 10% FBS and 1% penicillin/streptomycin (ThermoFisher, Waltham, Mass.). For DNA transfections, 50,000 HFFs were resuspended in 10 uL of Buffer R and electroporated using a 1700V, 20 ms pulse width, 1 pulse program with 1 µg DNA in a Neon transfection system (ThermoFisher, Waltham, Mass.). For siRNA transfections, 8,000-10,000 cells/cm² were treated with 25 nM or 200 nM siRNA with Lipofectamine2000 (ThermoFisher, Waltham, Mass.) according to the manufacturer's recommendations. IPF and non-IPF human lung core biopsies were generously provided by Dr. Eric White and the Lung Tissue Research Consortium (NHLBI: HHSN2682016000021). Selected cores all came from distal sections of lung parenchyma. Human subjects approval for this tissue was obtained through the University of Michigan Institutional Review Board. This study abides with the Declaration of Helsinki principles. For information on the oligos, antibodies, and uncommon chemicals used in this work, please refer to the Tables 1, 2, and 3 for supplier and use information.

Generation of Recombinant Constructs—LEMD3 Constructs: LEMD3 constructs were derived from the pSVK3-FLAG-MAN1 construct, kindly provided by Dr. Howard Worman (Addgene plasmid #26002). (33) Site directed mutagenesis (SDM) was performed using the Q5 SDM kit (New England Biolabs, Ispwich, Mass.) according to their protocol, including the use of "NEB BaseChanger" applet to design primers and select PCR conditions. Primers and associated melting points for each mutagenesis are listed in Table 3. Constructs were confirmed with Sanger sequencing (MacrogenUSA, Rockville, Md.).

DN LEM Construct. DN Kash and DN Control plasmids (pCDHEF1-MCS1-puro-mCherry-Nesprin-1αKASH and pCDH-EF1-MCS1-puro-mCherry, respectively) were kindly provided by Dr. Jan Lammerding and are described in detail in (40). The DN LEM construct was created by Gibson Assembly of the N-terminal LEM domain cDNA from LEMD3 (without FLAG) from pSVK3-FLAG-MAN1 into the frame occupied by Nesprin-1αKASH in the pCDHEF1-MCS1-puro-mCherry-Nesprin-1αKASH construct with primers and PCR conditions as described in Table 3.

Western Blotting—For non-phosphoprotein western blots: cell lysates from tissue culture plastic or from 2 or 25 kPa, 150 cm Petrisoft dishes (Matrigen, Brea, Calif.) were either: harvested directly in 4× protein loading buffer (Licor, Lincoln, Nebr.) supplemented with protease and phosphatase in-hibitors (#A32959, ThermoFisher, Waltham, Mass.) according to the manufacturer's instructions; or, processed with the NE-PER compartment isolation kit (ThermoFisher, Waltham, Mass.) according to the manufacturer's instruction. Lysates were treated with 0.3 µL of benzonuclease (ThermoFisher, Waltham, Mass.) for 15 minutes at room temperature with vigorous shaking. Samples were heated to 95 C for 5 minutes and run on a 4-12% Bis-Tris gel in 1×MES buffer and run for 70 minutes at 150V. The gel was then transferred to a nitro-cellulose membrane using the XCell Blot Module (ThermoFisher, Waltham, Mass.) at 25V for 65 min-utes. Membranes were air-dried for an hour, blocked with 5% non-fat milk in 1×PBS for an hour at room temperature, and then incubated with primary antibodies as described in Table 3 in 1×PBS-T with 1% milk for 16-24 hours at 4 C. Near-IR or HRP conjugated secondaries as described in Table 4 were then incubated with the blot and imaged subsequently on either an Odyssey CLx system for near-IR dyes (Licor, Lincoln, Nebr.) or a ChemiDoc MP system (Bio-Rad, Hercules, Calif.) with SuperSignal West Femto reagents (ThermoFisher, Waltham, Mass.) for HRP secondaries according to the manufacturer's instructions. Band analysis was performed using the associated Licor or Biorad software.

For phospho-protein western blots: The procedure above was followed with the following changes: Cells were treated with 100 µg/mL TGFβ 90 minutes before lysis. Membranes were incubated in and washed in buffers formulated with TBS instead of PBS. Membranes were blocked in 5% BSA in 1×TBS and all antibody incubations were done in 1% BSA in 1×TBS-T.

For recombinant LEMD3 western blots: Two samples of HFFs were prepared and electro-porated as above and plated onto each plastic or hydrogel surface for 12 hours (protease inhibitor experiments) or 24 hours (LEMD3 fragment abundance and deletion mutant experiments) before harvesting. qPCR—RNA was isolated from cultured cells using RNEasy Plus Mini kits (Qiagen, Hilden, Germany) according to the manufacturer's instructions. cDNA libraries were constructed using RT2 First Strand kit (Qiagen, Hilden, Germany) according to the manufacturer's instruction. 25 µL qPCR reactions were prepared using SYBR Green Master Mix (ThermoFisher, Waltham, Mass.) with 250 nM primers, listed in Table 3 and 10 ng input cDNA. Reactions were carried out on a StepOnePlus (ThermoFisher, Waltham, Mass.) for 40 cycles. Melt curves were visually inspected after each run to confirm a single, defined peak in the derivated intensity plot. Data from each run was imported into LinRegPCR, which performed baseline correction and measured PCR efficiency by amplicon group as described in (81). The relative number of transcripts was calculated by dividing the Cq threshold by the PCR efficiency for the reaction raised to the power of Cq, the cycle number at which the threshold is reached for a given target. For relative quantification be-tween conditions, LEMD3 transcripts were either: normalized for each condition to the mean of two reference genes, 18S and ACTB, if the samples were all from a single stiffness condition; or, normalized to 18S alone if substrate stiffness was an experimental condition.

Smad-Driven Luciferase Assays—HFFs were transfected with Cignal Lenti Reporter virus (Qiagen, Hilden, Germany) with a MOI of 40 and subsequently selected using 400 ng/mL puromycin until untransduced HFFs died. Stably transfected HFFs, with or without additional LEMD3-focused genetic treatments as described above, were plated at 10,000 cells/well on a HTS plate (Matrigen, Brea, Calif.) containing glass surfaces and polyacrylamide gels, which ranged in stiffness from 0.2 kPa to 50 kPa, all functionalized with 10 µg/mL plasma-purified human fibronectin according to the manufacturer's instruction. Cells adhered to the surfaces for 4 hours in serum-free DMEM supplemented with 1% BSA and 1% penicillin/streptomycin. Media was then supplemented with the desired amounts of TGFβ and, when applicable, with cytoskeletal agents as described in the results. HFFs were then incubated for 16 hours at 37 C before the luciferase re-action. Wells were supplemented to 2 mM VivoGlo d-luciferin (Promega, Madison, Wis.) using a plate reader controlled auto-injector system and light production was subsequently quantified every 5 minutes for 30 minutes on a Synergy H4 plate reader (BioTek, Winooski, Vt.). The raw luciferase signal was the median intensity measured over this timecourse minus the intensity from luciferase-transfected cells not treated with TGFβ to account for any TGFβ elaborated and activated by the cells in situ. Cells were then fixed with 4% paraformaldehyde, permeabilized with 0.1% Triton X-100, and then stained with 1:10,000 Hoechst 33342 in 1×PBS for 30 minutes at room temperature (ThermoFisher, Waltham, Mass.). The raw luciferase signal was then normalized to the nuclear signal, which was inside a linear standard curve form cells plated on glass and on polyacrylamide within each plate. Data for each condition was then fit to a three-parameter logistic equation using a least-squares minimization fit in Prism (Graph-Pad, La Jolla, Calif.). For curves that did not converge with this model, individual data points are shown as the mean with the standard error of the mean to illustrate data heterogeneity. Otherwise, the trends across the maximal luciferase signal ("Top" variable from the model) or the mid-transition point observed between "Bottom" and "Top" signals ("EC50" variable from the model, called "transition point" in text), were statistically compared using an ANOVA with "Test for Trends," which restricts the hypothesis testing to a particular order of the data-sets (e.g. max luciferase signal as a function of increasing TGFβ dose or transition point as a function of increased LEMD3 expression). Each data point represents at least three biological replicates.

Proximity Ligation Assays—Ex vivo PLA: lung biopsy samples were prepared by OCT embedding flash-frozen tissue (Tissue-Tek, Sakura Finetek, Torrance, Calif.) and preparing 10 µm cryosections on a CryoStar NX70 (Thermo Fisher, Waltham, Mass.). Sections were fixed for 10 minutes at 4 C in 2% paraformaldehyde in 1×PBS. Protein-protein proximity ligation assays (PLA) were performed with anti-body pairs listed in Table 4 as described previously in (42) with the following modifications: all primary antibody incu-bations were done for 16-24 hours at 4 C, sections were blocked in 0.5% Tween-20, 0.1% Triton X-100, 0.5% gela-tin, 5% donkey serum, 2% bovine serum albumin (BSA), and 5 µg/mL poly dI-dC DNA in PBS, and sections were actin counter-stained with 1:40 phalloidin-488 (Ther-moFisher, Waltham, Mass.) for 30 minutes at room tem-perature following the PLA reaction using the IF protocol rec-ommended by Sigma's PLA Resource Center. Slides were analyzed using an Axiovert 200M microscope (Carl Zeiss Microscopy, Jena, Germany) with an UltraVIEW spinning disk (PerkinElmer, Waltham, Mass.) and Flash 4.0v2 cMOS camera (Hamamatsu Photonics, Hamamatsu City, Japan). Low resolution images (20×) were collected using a 0.8NA Plan-Apochromat, and high resolution images (63×) were collected using a 1.4NA Plan-Apochro-mat objective (Carl Zeiss Microscopy, Jena, Germany). Image acquisition and analysis was preformed in Volocity (PerkinElmer, Waltham, Mass.). To analyze the incidence of LEMD3-Smad2/3 interactions between IPF and non-IPF biopsies at least 6 random points were chosen by Volocity in each section and registered to a serial section of the same tissue which was prepared as a no primary antibody PLA control. Tiled images with 20% overlap were acquired at 20×, covering a 628 µm by 334 µm area with z-slices acquired every 0.6 µm. The PLA signal was processed in Volocity using a consistent intensity threshold to identify PLA puncta, which were then spatially filtered by excluding PLA signal not associated with the actin or DAPI tissue-based signals. The remaining PLA signal was processed using the "Subtract" function to remove tissue autofluores-cence, measured inde-pendently in an unused spectral win-dow (615 nm, width 70 nm). The PLA signal was then normalized to the measured nuclear volume in the image slice. Relative PLA incidence between conditions was cal-culated by subtracting the normalized PLA signals between experimental and no primary antibody at each co-registered pair of points. High resolution imaging (63×) of each tissue was preformed over at least 6 randomly chosen areas, each 111 µm by 106 µm with z-slices acquired every 0.2 µm, to measure the cytosolic and nuclear PLA compartments in tissue. Signal processing was similar to the low resolution processing described above except that the PLA signal was subdivided using the "Exclude Non-Touching" function in Volocity to measure nuclear and non-nuclear associated signal.

In vitro PLA: Protein-protein PLA was per-formed with antibody pairs listed in Table 4 as described in (42) with the following modifications: cells were plated on FN-coated glass or hydrogels (Matrigen, Brea, Calif.). All primary antibody in-cubations were performed for 16-24 hours at 4 C and cells were counter-stained with 1:40 phalloidin-488 or phalloidin-546 in 1×PBS for 30 minutes at room tempera-ture and/or further processed for IF imaging using the procedure recommended in Sigma's PLA Resource Center. For all recombinant LEMD3 and C-terminal fragment experiments, HFFs were electroporated as above and allowed to culture for 24 hours on 10 µg/mL fibronectin coated glass or hydrogels before fixation. For LEMD3-phospho-Smad2/3, LEMD3-Smad2/3+TGFβ and for Smad2/3-Smad4 PLA assays: cells were treated 90 minutes before fixation with 50 µg/mL for LEMD3- and CTF-Smad2/3 assays, 100 µg/mL TGFβ for LEMD3-phospho-Smad2/3 experiments and 500 µg/mL TGFβ for Smad2/3-Smad4 experiments. For FLAG post-staining of PLA processed tissues, cells were blocked with unlabelled Affi-niPure donkey anti-rabbit antibodies (Jackson ImmunoRe-search, West Grove, Pa.) at a 1:10 dilution in 1×PBS-T at room temperature for 1 hour before further IF processing with 1:1000 rabbit anti-FLAG (#F7425, Sigma-Aldrich, Darmstadt, Germany) for 1 hour in PBS-T at room tempera-ture. Following three washes with PBS-T for 5 minutes, each sample was stained with 1:500 goat anti-rabbit 546 in PBS-T for 1 hour at room temperature, washed again and then counter-stained as above. For V5 post-staining of PLA processed samples, cells were incubated with 1:200 647 labelled anti-V5 antibody (R&D Systems, Minneapolis, Minn.) diluted in PBS-T at room tem-perature for 1 hour before washing three times in PBS-T for 5 minutes each and then counter-stained as above. Imaging and analysis were performed as described for high-resolution ex vivo PLA signals except that no tissue autofluorescence signal was measured or needed to be subtracted and, when appro-priate, other IF signal (e.g. FLAG) were measured in parallel. For cells on Matrigen HTS plates (FIGS. 2c & 2d), the conflu-ence of cells prevented identifying individual cell boundar-ies. Instead the PLA signal was quantified as the PLA volume divided by the nuclear intensity for each image. Each data point represents at least 3 unique surfaces with at least 12 cells measured per surface. For Smad2/3-Smad4 experiments, only two independent hydrogels were analyzed for the "CTF 500 µg/mL" and "Neon 500 µg/mL" groups due to loss of hydrogels during processing. Each bar in FIG. 5D represents the mean with standard error of the mean for all the cells analyzed from that condition.

Atomic Force Microscopy and Cell Morphology—Ex-periments were conducted on an MFP-3D atomic force microscope (AFM) (Asylum Research, Santa Barbara, Calif.) on an inverted opti-cal microscope (Nikon, Melville, N.Y.). MCLT 0-10 cantilevers (Bruker Nano, Camarillo, Calif.) were functionalized manually with 4.47 µm polysty-rene beads. Probes were calibrated before each experiment using a combination of glass indention and thermal fluctua-tion measurements. Cellular and hydrogel measurements were acquired using a 2 nN rel-ative force trigger with a tip velocity of 2 µm/s. Hydrogels were measured over a 400 µm2 space without cells, sampled as a 4×4 array. Young's modulus was calculated using custom scripts in MATLAB (The Math Works, Waltham, Mass.) that use a linearized Hertz approach for force-indentation measurements 40-60 nm into each surface. Cells and hydrogels were assumed to be incompressible (Poisson's ratio, v, =0.5). After AFM analysis, cells were fixed in 4% PFA for 10 minutes and stained with 1:40 Phalloidin-488 and 1:1000 Hoescht 33342 for 30 minutes. Cell spread area and morphology were analyzed from im-ages taken at 63× in Volocity (as above). Each data point represents at least 3 unique surfaces with at least 10 cells per surface.

Mass Spectroscopy on LEMD3 Fragments—LEMD3 fragments were affinity purified from RIPA extracted lysates using FLAG (clone M2, #A2220, Sigma-Aldrich, Darmstadt, Germany) or V5 (clone V5-10, #A7345, Sigma-Aldrich, Darmstadt, Germany) affinity agarose according to the instructions of the manufacturer. Purified fragments were separated by SDS-PAGE on a 4-12% Bis-Tris gel in 1×MES buffer and visualized by Simply-Blue staining (Thermo Fischer, Waltham, Mass.). In gel digestion, nano-LC-MS/MS, and peptide identi-fication was performed as previously described (82) with the following modifications. Reverse phase chromatography was performed using an in-house packed column (40 cm long×75 μm ID×360 OD, Dr. Maisch GmbH ReproSil-Pur 120 C18 AQ 1.9 μm beads) and a 120 min. gradient. The Raw files were searched using the Mascot algorithm (ver. 2.5.1) against a protein database constructed by combining the FASTA file for LEMD3 with a contaminant database (cRAP, downloaded 11-21-16 from http://www.thegpm.org) via Proteome Discoverer 2.1. Only peptide spectral matches with expectation value of less than 0.01 ("High Confidence") were used.

Example 1

Figure 1B:
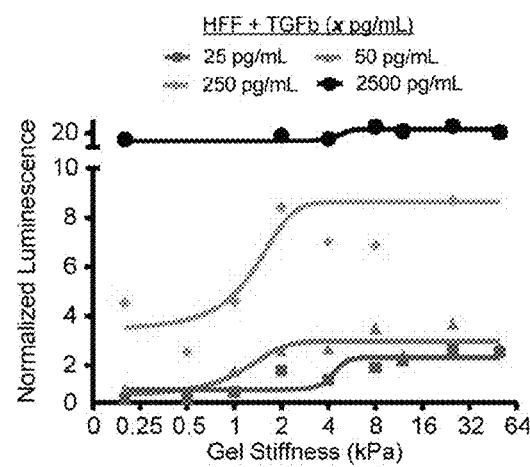

Fibroblast TGFβ Responsiveness is Potentiated by ECM Stiffness and Inhibited by LEMD3 Expression We sought to validate that fibroblasts in our system displayed stiffness-dependent TGFβ responsiveness using primary human dermal fibroblasts (HFFs) stably transfected with a Smad-driven luciferase. First, we characterized stiffness and morphology phenotypes associated with mechanotransduction using optical microscopy and atomic force microscopy (AFM). With increasing stiffness, fibroblasts underwent cellular compliance matching ($p=0.0022$) and increased their cell spread surface area ($p=0.1801$) and polarization ($p=0.0263$) seen in FIG. 1A and FIG. 8, respectively. Luciferase transfected HFFs showed a sigmoidal responsiveness to recombinant human TGFβ as a function of substrate stiffness (FIG. 1B). This stiffness potentiation was dose-dependent with increasing pg/mL doses of TGFβ appearing to shift the transition point of the sigmoid towards softer substrates ("soft-shift", $p=0.07$, FIG. 1B). Transition points in the pg/mL dose-range occurred at stiffness over a range from ≈1-4 kPa. These cells also showed the expected TGFβ dose-response (increasing luminescence with increasing TGFβ dose) on stiff substrates ($p<0.0001$, FIG. 1B). With regard to stiffness-dependent modulation of TGFβ signaling, this Example improves the resolution of prior work by more finely probing the stiffness space across a range from 0.5 kPa to 50 kPa. (10-13)

Figure 9A:
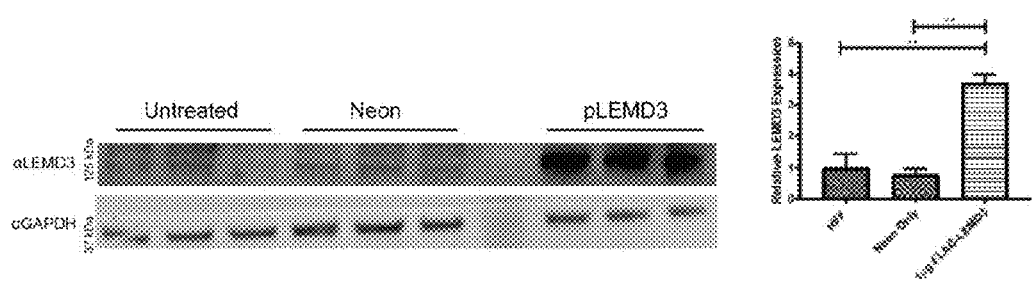
FIGS. 9A and 9B show over-expression and knockdown of LEMD3 using pFLAG-LEMD3-V5 and siRNA.
Figure 9B:
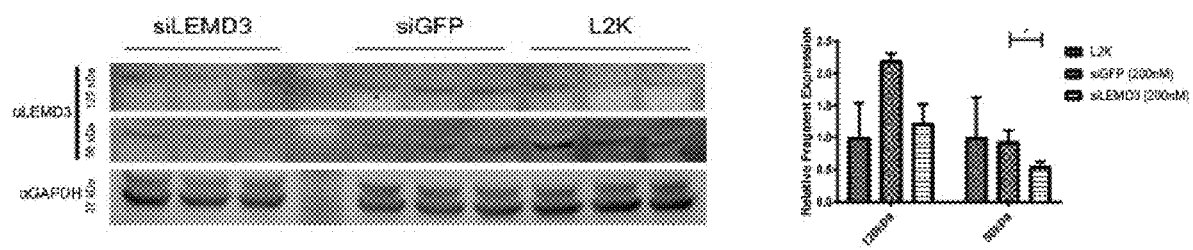

Having confirmed the TGFβ/stiffness phenotype, we tested how modulating LEMD3 alters the stiffness responsiveness of fibroblasts using Lipofectamine 2000 delivered siRNA against LEMD3 ("siLEMD3") and electroporation with pFLAG-LEMD3-V5 (LEMD3 over-expression plasmid with N-terminal FLAG epitope tag and C-terminal V5 epitope tag). Increasing LEMD3 expression (FIG. 9A) induced a decrease in maximal luminescence ($p=0.04$, FIG. 1C) and a "stiff-shift" in the stiffness response's sigmoidal transition point ($p<0.0001$, FIG. 1C). There was a corresponding "soft-shift" in the transition point ($p<0.0001$, FIG. 1C) and increase in maximal luminescence ($p=0.04$, FIG. 1C) when LEMD3 expression was decreased through siRNA treatment (FIG. 9B). There were no significant differences in either maximal luminescence or the stiffness transition point of the sigmoid model between HFFs treated with Lipofectamine2000, electroporated control HFFs ("Neon HFF"), or HFFs treated with concentration matched siRNA against GFP ("siGFP").

Figure 1C:
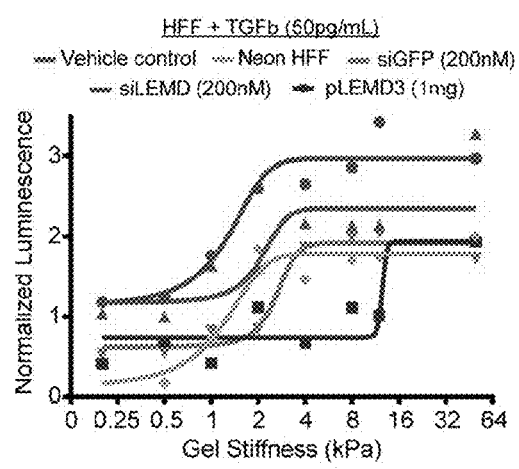
Figure 10A:
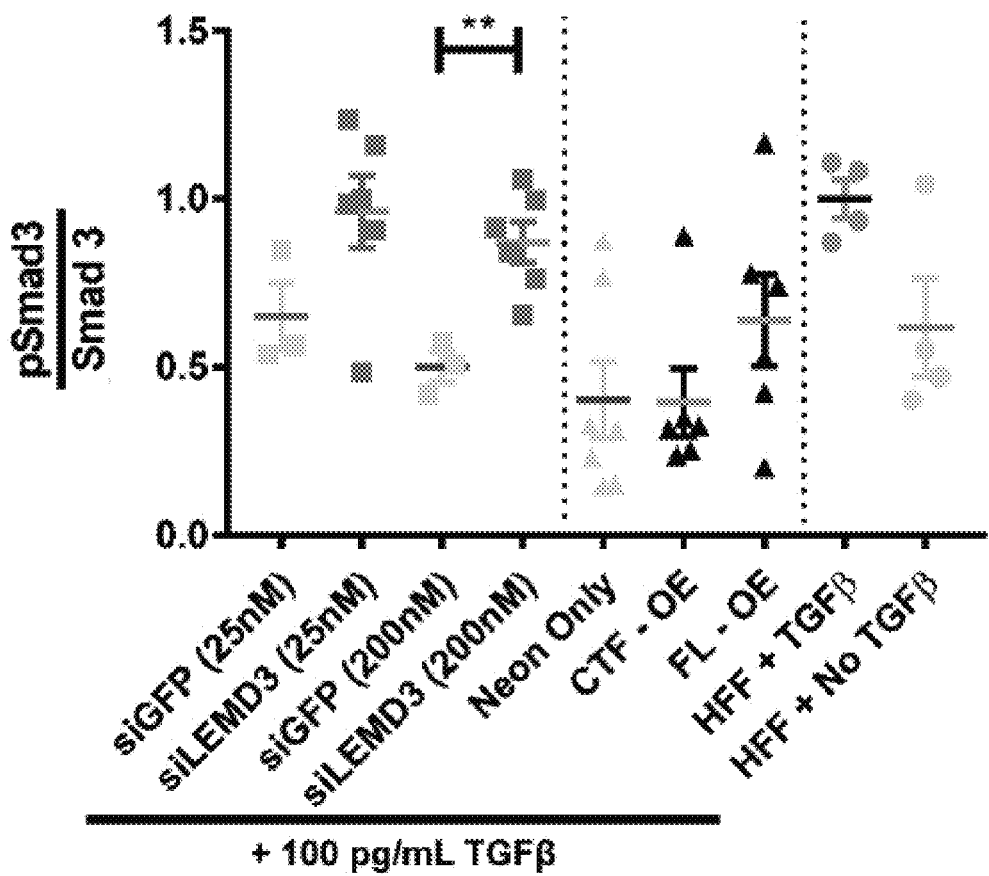
FIGS. 10A and 10B show that LEMD3 negatively regulates Smad3 phosphorylation.
Figure 10B:
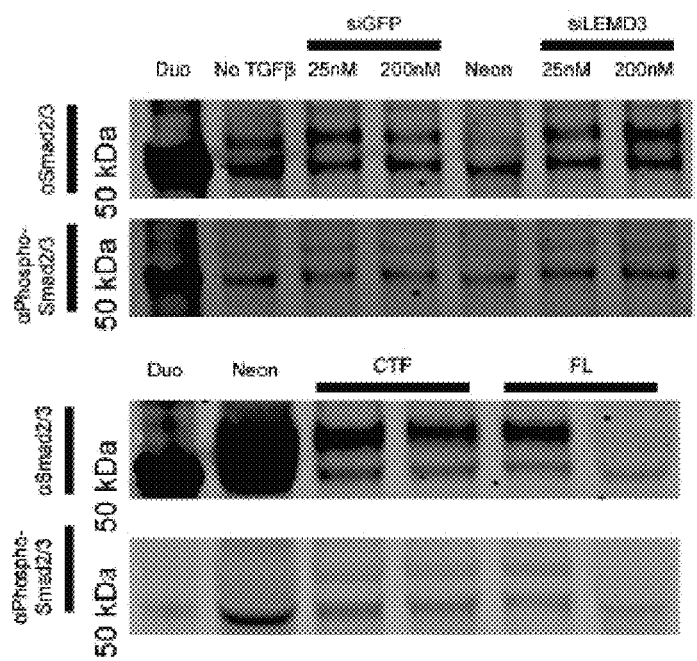

To connect LEMD3's TGFβ antagonism seen in FIG. 1C to Smad2/3's activation, we investigated the effect LEMD3's modulation on Smad3 phosphorylation (FIGS. 10A-10B). 100 μg/mL TGFβ treatment for 90 minutes increased the ratio of phospho-Smad3 to total Smad3 relative to untreated HFFs ($p=0.0506$, FIGS. 10A-10B). Treatment with either Lipofectamine 2000 or electroporation reduced the phosphor-Smad3/Smad3 ratio, but treatments with 25 nM and 200 nM siRNA against LEMD3 increased the phospho-Smad3/Smad3 ratio relative to siRNA against GFP ($p=0.1103$ and $p=0.0057$ for 25 nM and 200 nM siRNA groups, respectively, FIGS. 10A and 10B). Electroporation with pFLAG-LEMD3-V5 or a C-terminal fragment (pFLAG-LEMD3p.Δ21-669-V5, "CTF"), previously shown to be sufficient for Smad2/3 binding and de-phosphorylation (16, 18, 19, 21, 41), decreased the pSmad3/Smad3 ratio; however, as in FIG. 1C, there was no difference between electroporation controls and electroporation with any LEMD3 plasmids on tissue culture plastic. The stiffness-dependence of LEMD3's inhibition of TGFβ here is a novel finding.

Figure 1D:
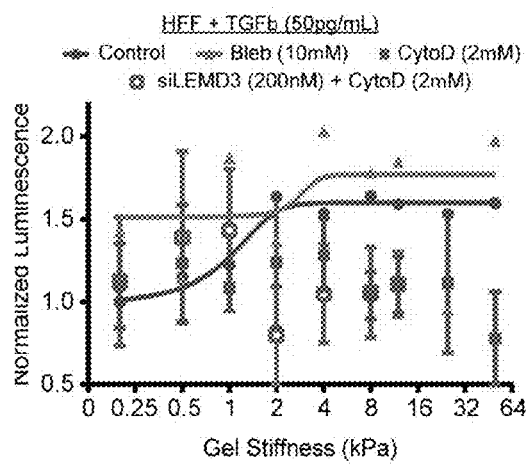

To test which components of the cell's microfilament cytoskeleton control the stiffness response of HFFs to TGFβ, chemical inhibition of the structural (cytochalasin D, a g-actin stabilizer) and contractility machinery (blebbistatin, a myosin II inhibitor) was used. Stiffness-dependent TGFβ responses required actin polymerization but did not require cellular contractility (FIG. 1D). Treatment with 10 μM blebbistatin (a myosin II inhibitor) did not significantly shift the transition point nor increase the maximal luminescence of cells relative to HFFs treated with TGFβ alone. Cells treated with 2 μM cytochalasin D showed a low, flat luminescent profile over increasing ECM stiffness, and the data did not converge to a sigmoidal model. Interestingly, siRNA against LEMD3 did not rescue the cytochalasin D phenotype, though the degree of LEMD3 knockdown may not have been sufficient (FIG. 9B). These data indicate that the actin cytoskeleton, but not cellular stress per se, is needed for stiffness-modulated TGFβ signaling.

Example 2

Figure 11:
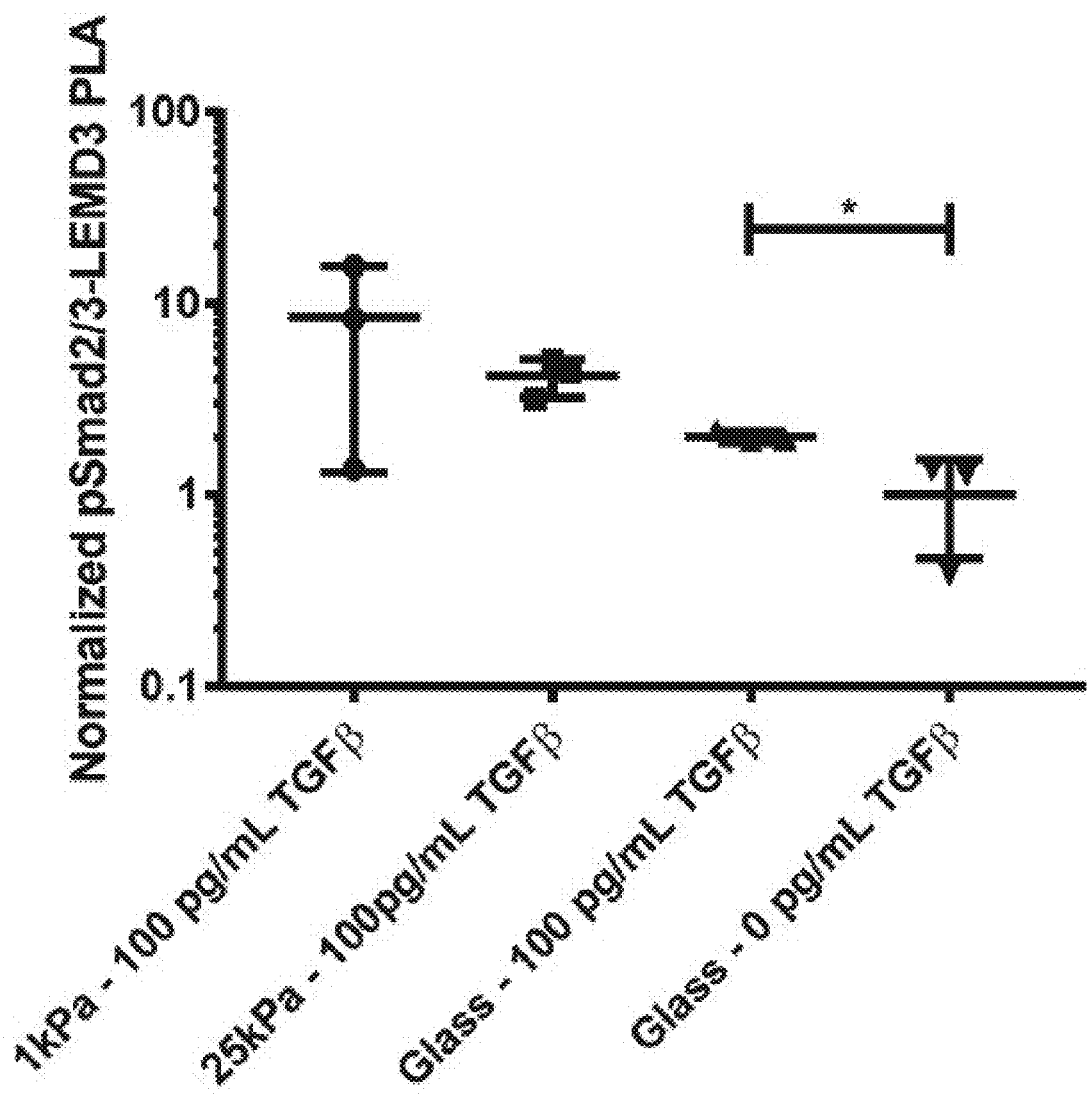
FIG. 11 shows LEMD3 binds phospho-Smad2/3 in a stiffness-dependent fashion. PLA interactions between phospho-Smad2/3 and LEMD3, normalized to HFFs on glass without TGFβ treatment, were stiffness- and TGFβ dose-dependent. Fibroblasts on glass treated with 100 pg/mL TGFβ have significantly more LEMD3-phospho-Smad2/3 interactions than cells without TGFβ treatment. (p=0.0333, Student's T-test). There was also a significant decrease in interactions with increasing stiffness (p=0.0305, ANOVA-Test for trends).

LEMD3-SMAD2/3 Complexes are Inversely Correlated to Substrate Stiffness and Occur Throughout the Cell Given that LEMD3 modulated the stiffness response of fibroblasts to TGFβ, we used proximity ligation assays (PLA, methodologically reviewed in (42)) to examine the stiffness dependence of LEMD3-Smad2/3 interactions on hydrogels whose stiffness is representative of physiologic (1 kPa) and fibrotic (25 kPa) lung tissue in humans. (43) LEMD3-Smad2/3 interactions were negatively correlated with substrate stiffness in both the cytoplasm and the nucleus (FIGS. 2A & 2B). This negative correlation was independent of TGFβ dosing (50 μg/mL, inside the range of stiffness-responsive doses identified in FIG. 1B), consistent with previous findings that LEMD3-Smad2/3 interactions are phosphorylation-independent. (21) While LEMD3-Smad2/3 interactions were unperturbed by TGFβ dosing, we explicitly tested the ability of LEMD3 to bind phospho-Smad2/3 (FIG. 11). We found that HFFs treated with 100 µg/mL TGFβ on glass had significantly higher LEMD3-phospho-Smad2/3 interactions than untreated fibroblasts (p=0.0333, FIG. 11) and that there was a significant negative correlation between substrate stiffness and LEMD3-phospho-Smad2/3 interactions (p=0.0305, FIG. 11). These data reveal the stiffness-dependence of LEMD3-Smad2/3 interactions. The data also confirm previous observations that LEMD3 can bind both phosphorylated and unphosphorylated Smad2/3. (21)

We extended our findings by performing the PLA assay across a finer range of stiffness with both HFFs and CCL210s, an adult, pulmonary-derived fibroblast line (FIG. 2C). Both CCL210s and HFFs showed a biphasic response to stiffness with peak values at 1 kPa. CCL210s demonstrated a greater dynamic range in response to stiffness as well as a more gradual loss of PLA interactions on progressively stiffer substrates relative to HFFs. Additionally, the abrupt loss of LEMD3-Smad2/3 interactions between 1 kPa and 4 kPa in HFFs was inversely correlated with the stiffness dependence of the sigmoidal transition point of the luciferase signal measured in FIG. 1B.

Interestingly, we found that approximately half of the PLA interactions on both substrates occurred in the cytoplasm of the cells. Across a broader range of stiffness, we found that the nuclear proportion of LEMD3-Smad2/3 interactions was inversely correlated to substrate stiffness in both HFFs (p<0.0001) and CCL210s (p=0.0199), as seen in FIG. 2D. Given that LEMD3 is thought to be an integral protein of the inner nuclear membrane, we validated our findings through V5-Smad2/3 PLA in cells transfected with pFLAG-LEMD3-V5 (FIGS. 2E & 2F). Near identical trends were observed with this independent PLA reaction—a reduction in PLA frequency overall (p<0.0001, FIG. 2F), and reductions in both the cytoplasm (p<0.0001, FIG. 2F) and nuclear (p=0.0018, FIG. 2F) compartments with increasing substrate stiffness. To control for the degree of recombinant LEMD3 expressed across stiffness conditions, we found a significant difference in the linear regression between PLA puncta per cell and the per-cell FLAG intensity in cells on both soft and stiff surfaces (p<0.0001, FIG. 2G). The steeper slope observed for cells on soft substrates confirmed a higher rate of LEMD3-Smad2/3 complex formation per arbitrary unit of LEMD3 expressed (as measured by the fused FLAG epitope) relative to stiff substrates.

Example 3

LEMD3-Smad2/3 Complexes are Inhibited by Actin Polymerization and not Potentiated by Disrupting Cytoplasmic-Nuclear-Lamina-LEMD3 Coupling We hypothesized that the frequency of LEMD3-Smad2/3 complexes would be decreased by transmission of ECM-driven cytoskeletal tension to LEMD3 through a two-part physical linkage: 1) the nesprin-sun LINC complex joining the nuclear lamina and actin cytoskeleton; and, 2) through nuclear lamina-LEMD3 couping via the LEM domain. We tested this hypothesis by disrupting the molecular linkages at either the level of the LINC complex, by expressing a previously validated dominant negative nesprin construct, DN-Kash-mCherry, (40) or by disrupting LEMD3-lamin interactions, by expressing a novel DN-LEM-mCherry constructs and assessing LEMD3-Smad2/3 complex formation by PLA. Neither DN Kash nor DN LEM expression increased the LEMD3-Smad2/3 PLA frequency relative to mCherry-only expressing fibroblasts on glass (FIGS. 3A & 3B). To assess if our findings were biased by the degree of DN Kash or DN LEM expression, we correlated PLA puncta against the mCherry expression of the fusion protein per cell. None of the Pearson's coefficients (r=−0.251 and r=−0.087 for DN Kash and DN LEM, respectively, FIG. 3C) varied significantly from 0 (p=0.0579 and p=0.43 for DN-Kash and DN-LEM, respectively, FIG. 3C), indicating that the degree of dominant-negative protein expression was not a likely explanation for our findings. These results also corroborated findings in FIG. 1D, where cellular contractility inhibition, through blebbistatin antagonism of myosin II, did not significantly modify the TGFβ stiffness-response of fibroblasts.

Figure 8:
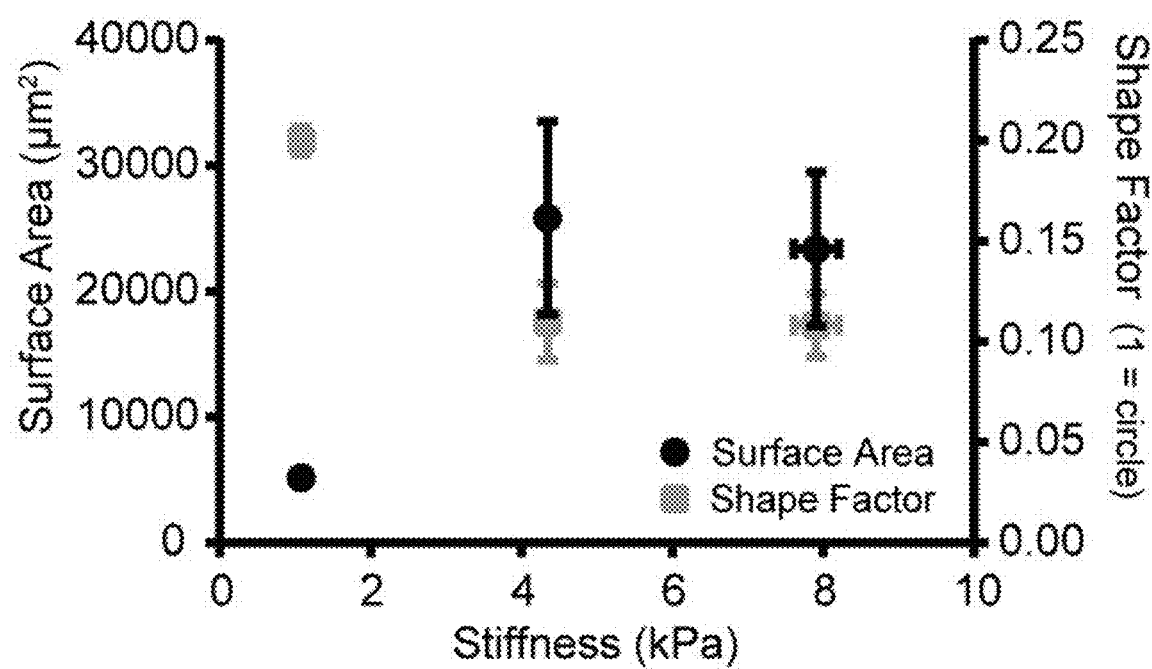
FIG. 8 shows that fibroblasts spread and polarize in response to substrate stiffness. Fibroblasts demonstrated mechano-sensitivity to ECM stiffness as shown by increased cell spreading (p=0.1801, ANOVA—Test for Trends) and polarization (p=0.0263, ANOVA—Test for Trends). All data represented by the mean.

Because g-actin stabilizing agents did modify the fibroblast stiffness-response (FIG. 1D), we examined the effect of actin polymerization on LEMD3-Smad2/3 complex formation by PLA. Actin polymerization was significantly negatively correlated to the frequency of LEMD3-Smad2/3 complexes (FIG. 3D-3F). Fibroblasts on glass treated with 2 µM cytochalasin D for 90 minutes demonstrated an increase in the total frequency of LEMD3-Smad2/3 complexes overall (p=0.0089, FIG. 3E). The frequency of LEMD3-Smad2/3 complexes also increased in the cytosolic (p=0.0871, FIG. 3E) and nuclear compartments (p=0.5657, FIG. 3E). Conversely, f-actin stabilization through jasplaki nolide treatment for 2 hours on 1 kPa hydro-gels demonstrated a dose-dependent decrease in LEMD3-Smad2/3 interactions (p<0.0001 for vehicle/DMSO treated cells vs both 100 nM and 200 nM jasplakinolide, and p=0.0312 for 100 nM vs 200 nM jasplakinolide treatment, FIG. 3F). Significant reductions in LEMD3-Smad2/3 complex formation were observed in both the cytoplasm (p<0.0001 for DMSO treated cells vs. both 100 nM and 200 nM jasplakinolide, FIG. 3F) and in the nucleus (p=0.0466 for DMSO treated cells vs. 100 nM jasplakinolide and p=0.002 for DMSO treated cells vs. 200 nM jasplakinolide, FIG. 3F). Considered with the results in FIG. 1A and FIG. 8, showing increased cell spreading, polarization, and stiffness as a function of substrate stiffness, these data suggested that actin polymerization in response to substrate stiffness helps coordinate the LEMD3-dependent stiffness response of cells to TGFβ.

Example 4

Figure 12A:
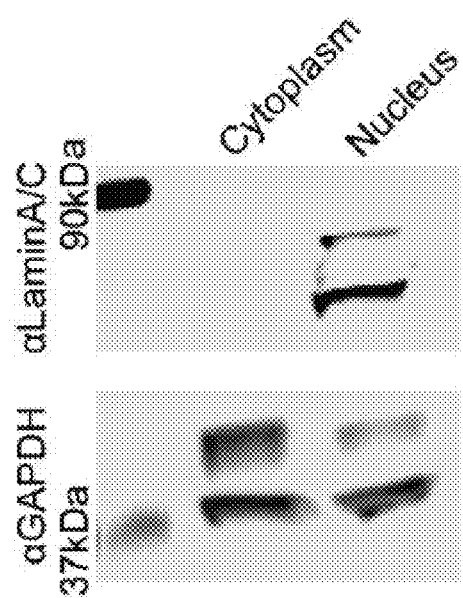
FIGS. 12A and 12B show that full length LEMD3 is localized to the nucleus but 46 kDa fragment is localized to the cytoplasm.
Figure 12B:
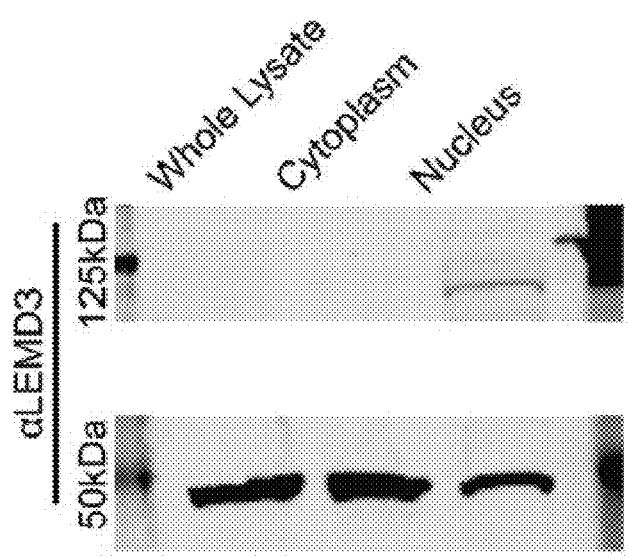

LEMD3 Fragments are Generated by a Serine Protease and Differentially Regulated by the Integrity of the Nuclear Lamina We observed cytosolic LEMD3-Smad2/3 interactions with PLA antibody pairs against the native protein and against a full length recombinant LEMD3 protein, expressing a V5 epitope tag. These data were supported by fractionated cell western blots of endogenous LEMD3, which revealed an ≈50 kDa LEMD3 fragment in the cytosol (FIG. 12B). These cytosolic LEMD3-Smad2/3 interactions seemed to be stiffness-regulated given their negative correlation with actin polymerization (FIG. 3D-3E).

Figure 4A:
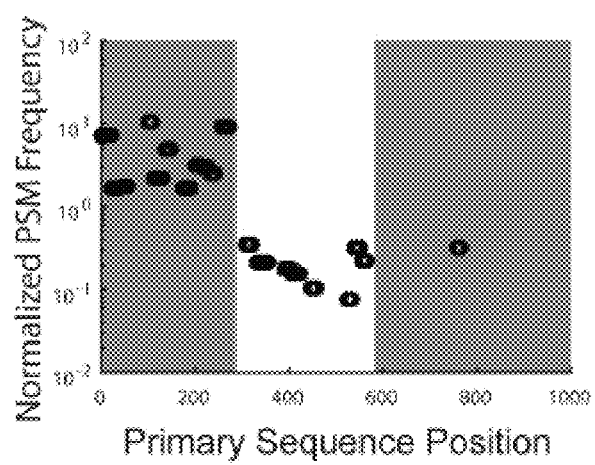
FIGS. 4A through 4E show LEMD3 is proteolytically modified by a serine protease.
Figure 4B:
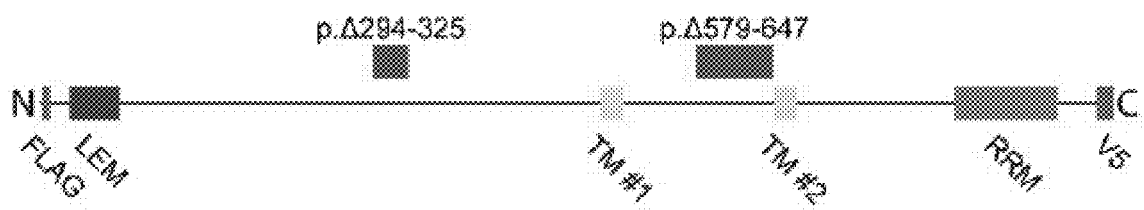
Figure 4C:
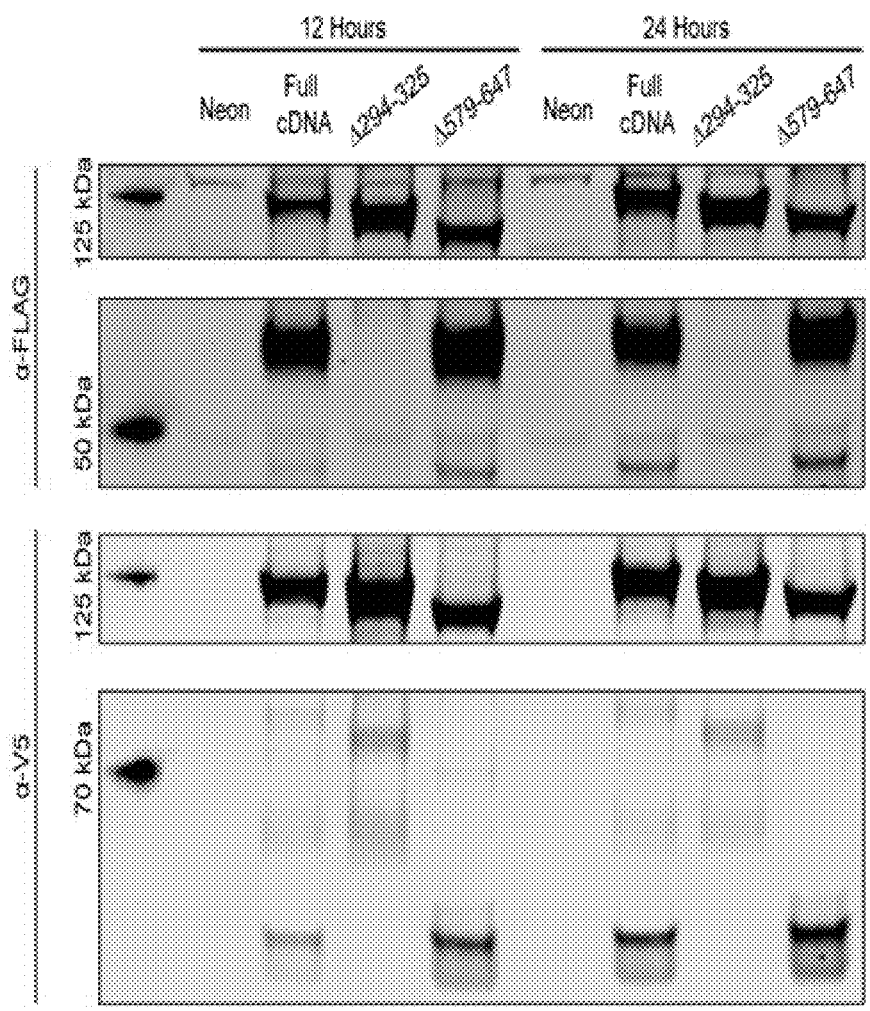

To understand how LEMD3 could interact with Smad2/3 in the cytosol, we performed mass spectroscopy on lysates from cells transfected with pFLAG-LEMD3-V5 constructs (FIG. 4A). Results from a FLAG-purified 60 kDa fragment showed two transitions in the peptide spectral matches to LEMD3's primary sequence—first at p.294-325 and second at p.579-647 (these protein coordinates are offset by 20 amino acids inserted with the N-terminal FLAG tag in the pFLAG-LEMD3-V5 construct from the native protein sequence). The primary sequence relationship between these two regions and other known domains of LEMD3 are shown in FIG. 4B. Deletion mutants (pFLAG-LEMD3p.Δ294-325-V5 & pFLAG-LEMD3p.Δ579-647-V5) exploring these two regions showed differential fragment presentation in western blots which probed either the N-terminal FLAG tag or C-terminal V5 tag of the recombinant protein (FIG. 4C). Specifically, pFLAG-LEMD3p.Δ294-325-V5 lysates lacked the 60 kDa FLAG fragment (the FLAG fragment at <50 kDa was also missing but was not consistently found in all blots) and the 46 kDa V5 fragment. Interestingly, the 46 kDa V5 fragment was similar in size to the cytoplasmically localized fragment of LEMD3 noted earlier from endogenous lysates (FIG. 12B). The pFLAG-LEMD3p.Δ579-647-V5 lysates did not appear to change the FLAG fragment presentation but did eliminate V5 fragments at 60 kDa and 85 kDa. These genetic data suggested that the protein is modified in at least two regions, one in the nucleoplasm (Δ294-325) and one in the perinuclear membrane space (Δ579-647). Moreover, all the V/C-terminal fragments identified by our genetic mutations contained the CTF used in FIGS. 10A-10B, indicating that they are sufficient for binding Smad2/3 in a stiffness-dependent fashion and binding Smad2/3 in the cytoplasm.

Figure 4D:
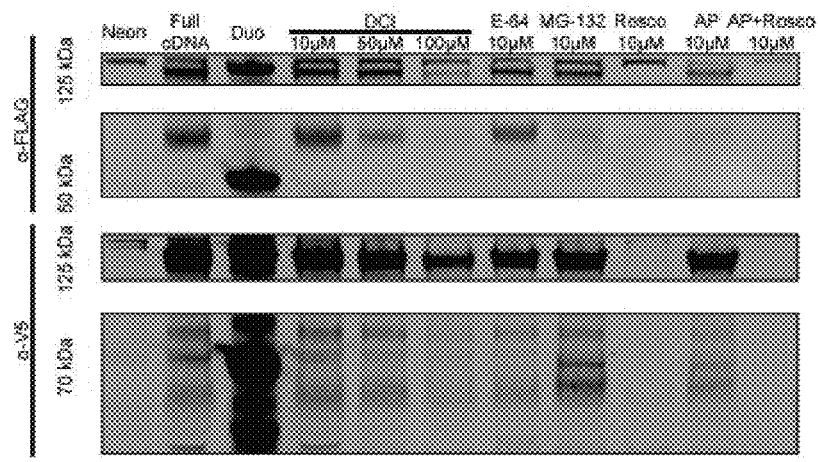
Figure 4E:
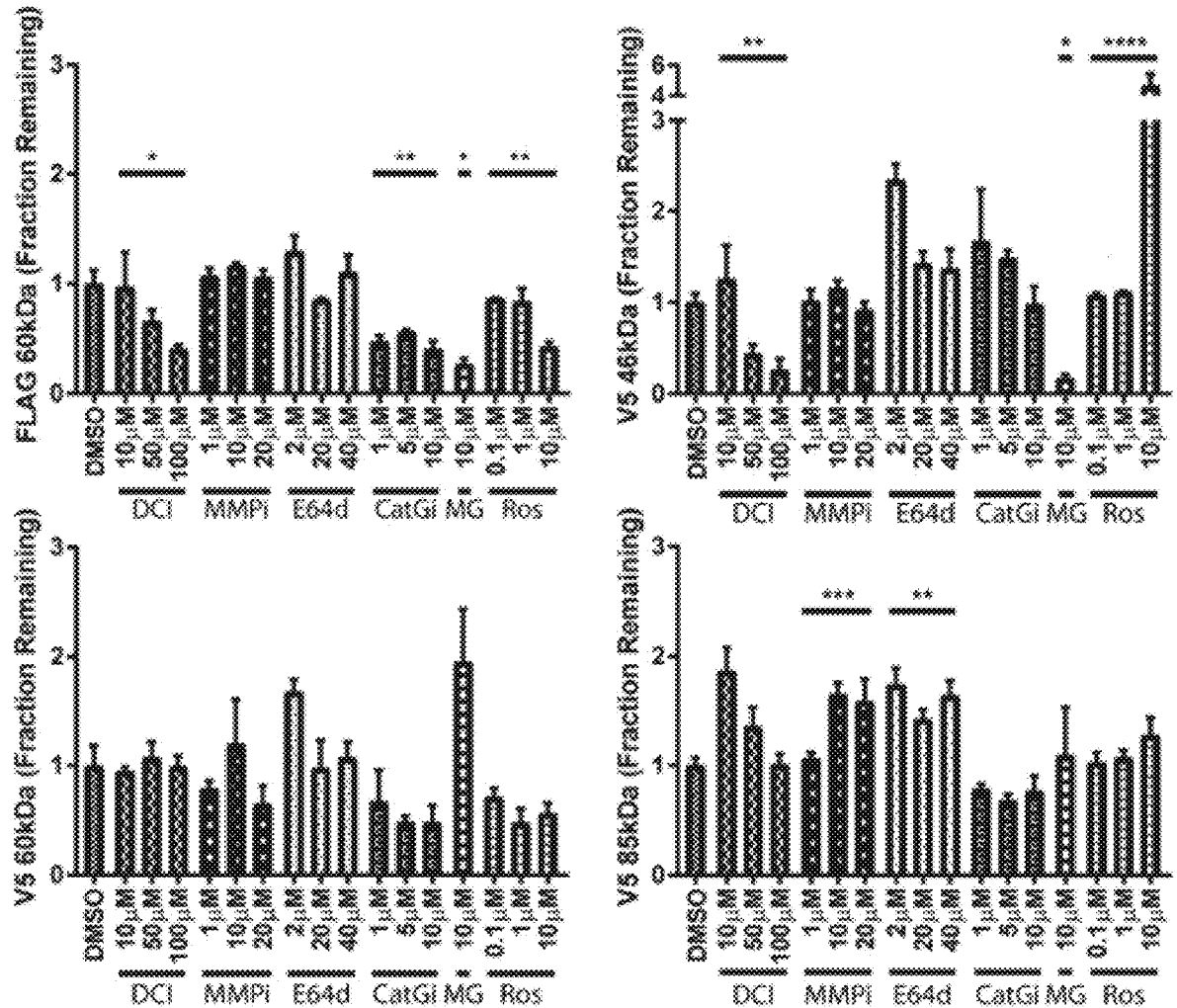

Following the observation of cytoplasmic interactions with an intron-less LEMD3 cDNA construct, we hypothesized that these fragments were generated proteolytically. We used western blots to determine the effects of several broad-spectrum protease inhibitors against cysteine (E64 & E64d), serine (3,4 dichloroisocoumarin, DCI) and matrix metalloproteinases (MMP inhibitor III—MMPi) as seen in FIGS. 4D & 4E. From fragments controlled by the Δ294-325 region, the 60 kDa FLAG frag-ment was reduced relative to the full length transcript in cells treated with DCI (p=0.0153, FIG. 4E), which is a known inhibitor of cathepsin G, elastase, thrombin, plasmin, factors Xa & XIa, and granzymes A, B and H. (44) This fragment was also reduced when cells were treated with MG-132 (p=0.0238, FIG. 4E), an inhibitor of the 26S proteosome complex, an important regulator of overall protein homeostasis and particularly critical for degrading ubitquinated proteins (reviewed recently in (45)). These same trends were observed for the 46 kDa V5 fragment (DCI: p<0.0001; MG-132: p=0.0238, FIG. 4E), which is also controlled by the A294-325 region. Monash University's PROSPER (Protease specificity Prediction Server as described in (46)) predicted only a single serine protease, cathepsin G, cleaving between p.V275-L276 (native protein coordinates, score=1.14) in pFLAG-LEMD3p.Δ294-325-V5's deletion region. Using a more selective cathepsin G inhibitor, we found a significant reduction in the 60 kDa FLAG fragment (p=0.0075, FIG. 4E) but no significant trend with the 46 kDa V5 fragment. From the A579-647 region, the 60 kDa V5 fragment was not significantly modified by any protease inhibitor treatments explored here. Interestingly, the 85 kDa fragment's abundance was only potentiated by MMPi (p=0.0004, FIG. 4E) and E64d (p=0.0044, FIG. 4E) treatment. These fragment data together suggested that a serine protease, possibly cathepsin G, operates in the Δ294-325-V5 region, with a distinct mechanism of fragment generation occurring in the Δ579-647 region.

Because pFLAG-LEMD3p.Δ579-647-V5's deletion region lies in the peri-nuclear membrane space, we hypothesized that this location might only be susceptible to degradation during mitosis. Because LEMD3's localization is controlled necessarily by its association to the nuclear lamina through its LEM domain (14, 15, 35-37), we chose roscovitine, a selective inhibitor of cdk1, which prevents cell cycle progression in part by preventing lamin phosphorylation and disassembly. (47) Interestingly, roscovitine only modulated fragments associated with the nucleoplasmic site (sites controlled by pFLAG-LEMD3p.Δ294-325-V5)—significantly reducing the generation of the 60 kDa FLAG fragment (p=0.0051, FIG. 4E) and significantly increasing the generation of the 46 kDa fragment (p<0.0001, FIG. 4E).

Figure 13A:
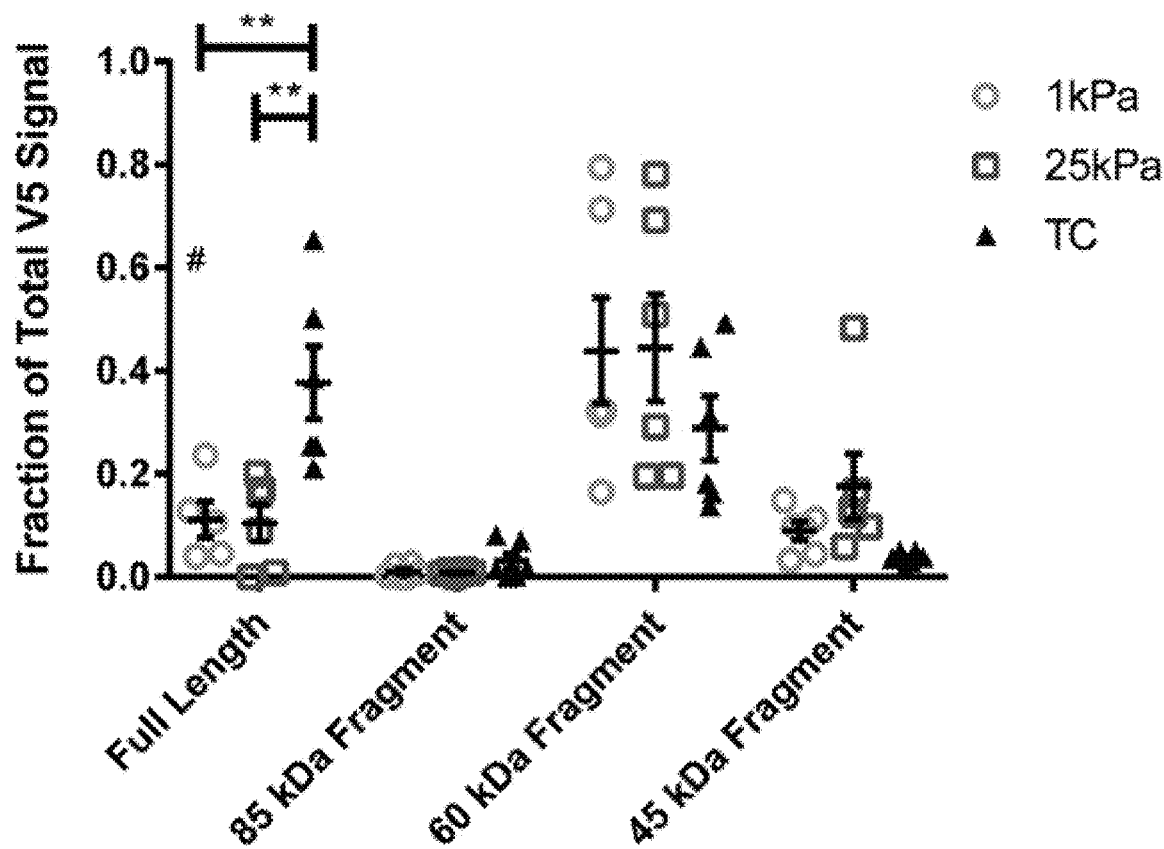
FIGS. 13A and 13B show LEMD3 C-terminal fragments are not significantly differentially abundant in HFFs cultured on 1 and 25 kPa hydrogels.
Figure 13B:
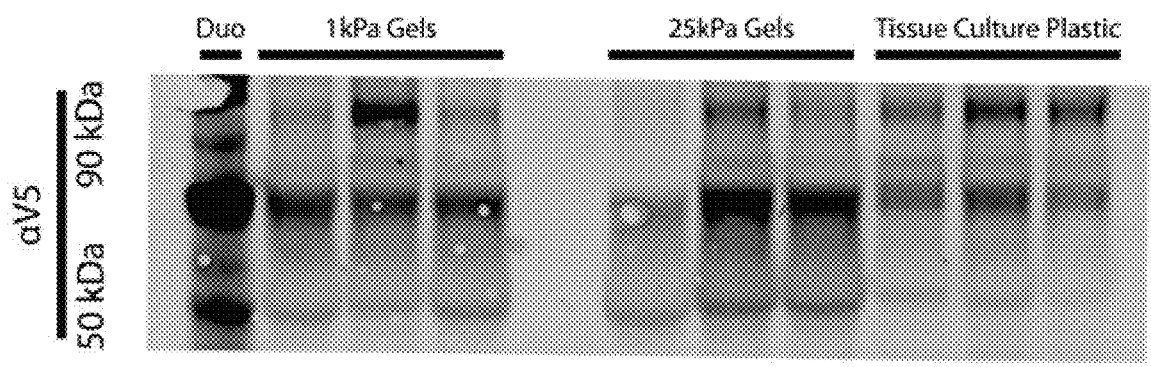
Figure 14A:
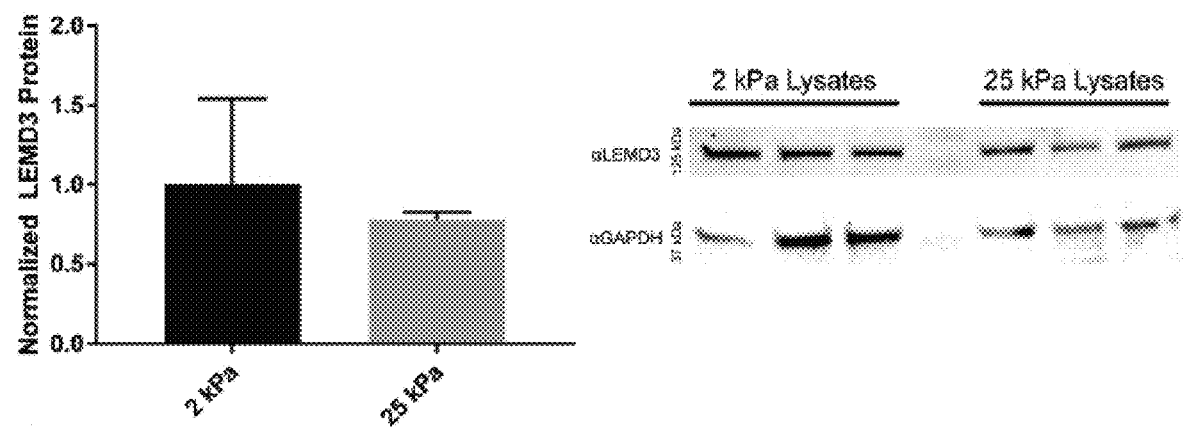
FIGS. 14A and 14B show LEMD3 is not directly regulated by substrate stiffness at the mRNA or protein level.
Figure 14B:
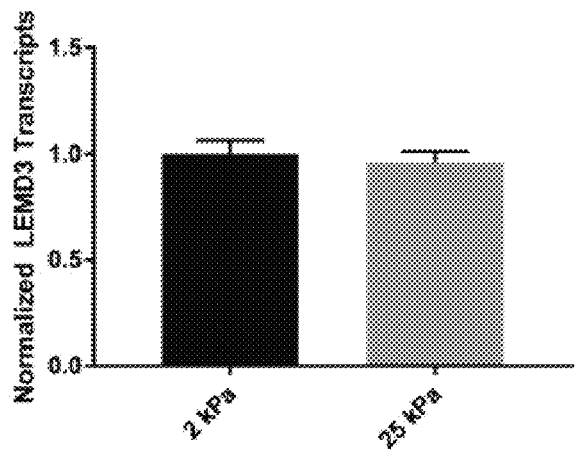

Finally, FIG. 2D showed that LEMD3-Smad2/3 interactions shifted towards the cytoplasm with increasing substrate stiffness. We tested whether this shift was driven by alterations in C-terminal LEMD3 fragment abundances as a function of substrate stiffness with western blots assaying HFFs transfected with pFLAG-LEMD3-V5 (FIGS. 13A & 13B). After 24 hours, cells grown on 1 kPa and 25 kPa hydrogels each had decreased proportions of full length LEMD3 relative to fibroblasts cultured on tissue culture plastic (p=0.0062 and p=0.0031 for TC vs. 1 kPa and TC vs. 25 kPa, respectively, FIG. 13A). Lysates from 1 kPa and 25 kPa hydrogels had similar abundances of the 85 kDa and 60 kDa fragments, though the 45 kDa fragment was almost twice as abundant on 25 kPa hydrogels as on 1 kPa hydrogels (p=0.5196, FIG. 13A). We extended our findings to endogenous LEMD3 and found that full length native LEMD3's abundance was not modulated significantly by culture on 1 kPa or 25 kPa surfaces (FIG. 14A). LEMD3's mRNA expression level was also invariant to culture on these surfaces (FIG. 14B).

Example 5

The C-terminal Fragment of LEMD3 Binds Smad2/3 in a Stiffness-Dependent Fashion, Antagonizes Smad2/3-Smad4 Complexes, and Binds PPM1α

To understand the biological significance of these novel C-terminal fragments of LEMD3 ("CTF") in the regulation of TGFβ signaling, we used PLA to ascertain their association with Smad2/3 and their ability to antagonize TGFβ signaling. The consensus (i.e. cloned past the 2nd cleavage site so as to contain the conserved sequence from all C-terminal fragments) CTF described earlier for FIGS. 10A and 10B has been shown to be sufficient for Smad2/3 binding (16, 18, 19, 21, 41) and lacks the necessary domains for nuclear localization (14, 18, 33). We repeated the recombinant PLA experiments from FIGS. 2B & 2F between CTF's V5 epitope and Smad2/3 to ascertain 1) whether this fragment of LEMD3 was sufficient for generating stiffness-dependent Smad2/3 interactions; 2) whether these fragments were uniquely localized to the cytoplasm; and, 3) whether the CTF-Smad2/3 interactions were dependent on the phosphorylation state of Smad2/3.

Figure 15:
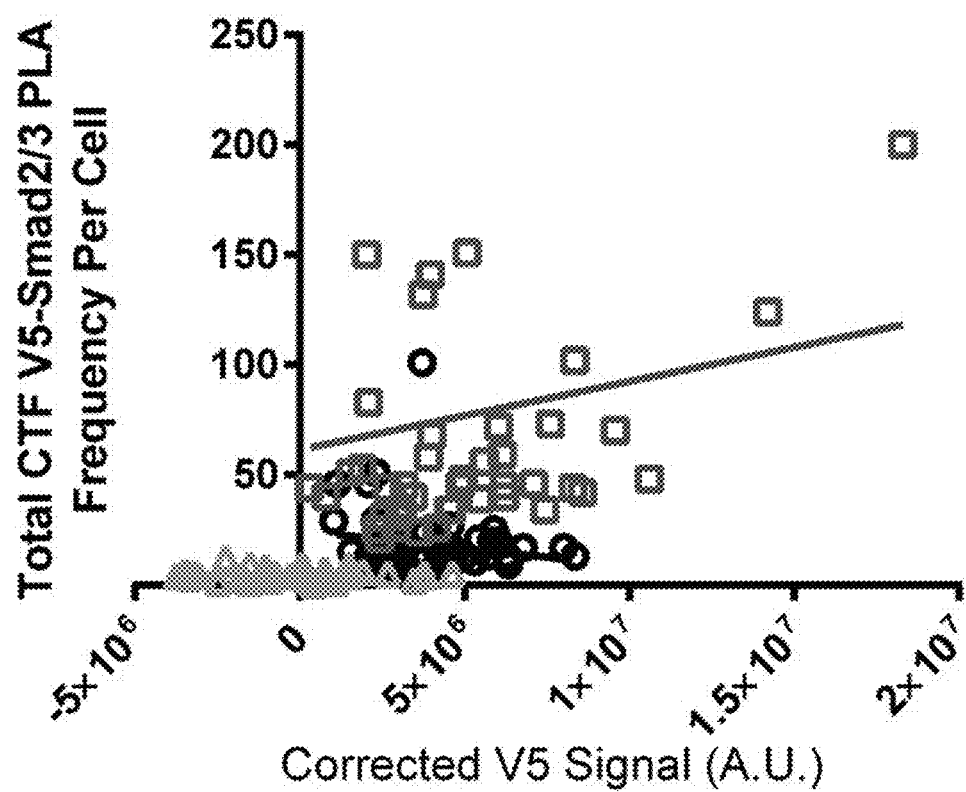
FIG. 15 shows that a C-terminal fragment of LEMD3 binds Smad2/3 preferentially on soft substrates independent of recombinant protein expression. The higher V5-Smad2/3 PLA frequencies observed in fibroblasts on 1 kPa hydrogels in FIG. 5a&b was independent of the degree of V5 expression. The linear regressions of individual cells' PLA vs. V5 staining intensity was higher for cells on 1 kPa hydrogels than on 25 kPa hydrogels ($p=0.1476$, difference in slopes).
Figure 16:
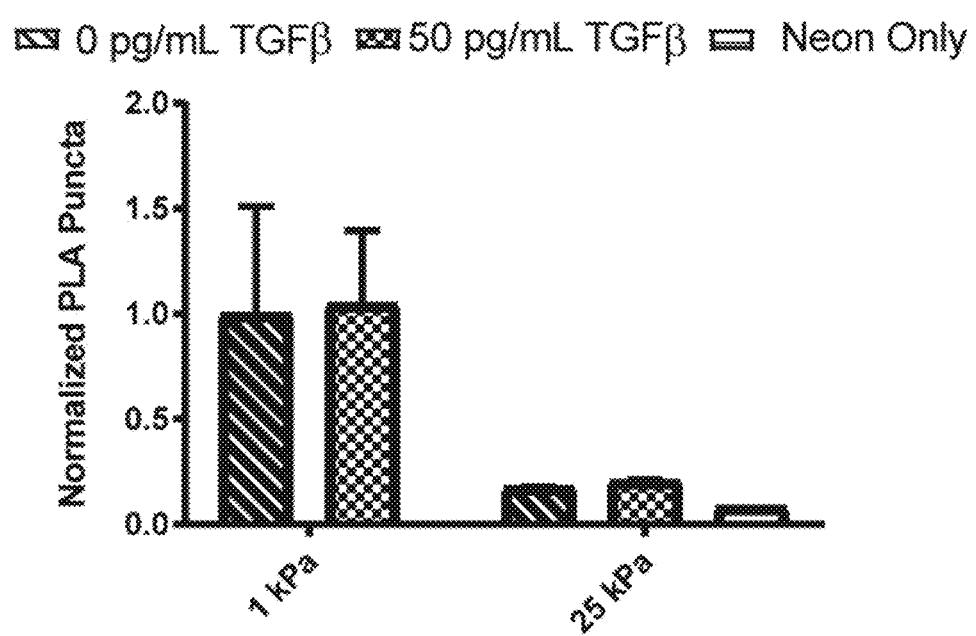
FIG. 16 shows a C-terminal fragment of LEMD3 binds Smad2/3 independent of TGFβ dosing. Interaction frequencies as measured by V5-Smad2/3 PLA revealed no significant difference in C-terminal fragment ("CTF") binding to Smad2/3 with or without TGFβ dosing on 1 kPa or 25 kPa hydrogels ($p=0.98$ and $p=0.99$ for comparisons of treated and untreated cells on 1 kPa and 25 kPa hydrogels, respectively). Both stiffness pairs of dose groups were compared using 2-way ANOVA with Sidak's post-test. All data represented by the mean with SEM.

The CTF-expressing fibroblasts on 1 kPa hydrogels had significantly more Smad2/3 interactions overall (p<0.0001, FIG. 5B), in the cytoplasm (p<0.0001, FIG. 5B), and in the nucleus (p=0.0082, FIG. 5B) relative to CTF-expressing HFFs on 25 kPa hydrogels. Transfected fibroblasts on 1 kPa and 25 kPa hydrogels had significantly more overall CTF-Smad2/3 interactions than electroporation control fibroblasts (p<0.0001 and p=0.0227 for 1 kPa and 25 kPa conditions, respectively, FIG. 5B). To control for degree of recombinant CTF expression we compared the V5 signal and the PLA interactions per cell across each group. We found that fibroblasts on 1 kPa hydrogels had a steeper slope (i.e. more PLA per arbitrary unit of V5 expressed) than fibroblasts on 25 kPa hydrogels (p=0.1476, FIG. 15). Furthermore, we found that TGFβ dosing (50 μg/mL) did not significantly vary the CTF-Smad2/3 interaction frequency on 1 kPa or 25 kPa substrates (p=0.98 and p=0.99, respectively, FIG. 16).

Unexpectedly, a significant fraction (≈40-55%, depending on stiffness) of CTF-Smad2/3 interactions took place in the nucleus (FIG. 5B). While the N-terminus of LEMD3 up to the first transmembrane domain has been shown to be necessary for faithful localization of full length LEMD3 to the nucleus (14, 33), the CTF does have an independent ability to bind both barrier-to-autointegration factor (BAF, a nuclear chromatin protein, (34)) and DNA directly (41), which may allow for enrichment of the CTF in the nucleus. Overall, these V5-Smad2/3 PLA assays with recombinant LEMD3 proteins confirmed 1) the negative stiffness correlation and TGFβ-independence of CTF-Smad2/3 complexes, mirroring the results observed with endogenous LEMD3 assays; and 2) that the CTF was sufficient for cytoplasmic LEMD3-Smad2/3 interactions.

Having demonstrated the CTF binds Smad2/3 in a stiffness—but not TGFβ dose-dependent fashion, we assayed whether CTF over-expression could antagonize TGFβ signaling by examining the effect of CTF's expression on the abundance of Smad2/3-Smad4 complexes. Smad2/3-Smad4 complexation is a necessary step for efficient nuclear translocation and activity as a transcription factor and is sensitive to Smad2/3's phosphorylation state. (48, 49) HFFs treated with 500 μg/mL TGFβ on 1 kPa hydrogels showed an increase in Smad2/3-Smad4 complexes relative to untreated HFFs (p=0.001, FIG. 5D). Over-expression of the CTF significantly abrogated this TGFβ-driven increase in Smad2/3-Smad4 complexes (p=0.0081, FIG. 5D). We queried whether endogenous LEMD3 and the CTF could bind PPM1α in the cytoplasm and nucleus by PLA. Both endogenous LEMD3 and the CTF bound PPM1α, demonstrated by interaction frequencies significantly above their respective negative controls (FIG. 5F, Total Interactions: p<0.0001 for both endogenous LEMD3 vs. a "No primary" control, and electroporation only/"Neon Only" control vs. CTF). Both endogenous LEMD3 and the CTF bound PPM1α significantly above background in the cytoplasm (FIG. 5F, Cytoplasmic Interactions: p<0.0001 for endogenous LEMD3 and p=0.0081 for the CTF) though only endogenous LEMD3 was found to significantly bind PPM1α in the nucleus (FIG. 5F, Nuclear Interactions: p<0.0001 for endogenous LEMD3 and p=0.2569 for the CTF). These data specifically demonstrated the CTF's ability to antagonize Smad2/3 signaling and its connection to PPM1α, a known LEMD3-associated phosphatase that antagonizes TGFβ signaling.

Example 6

Figure 6A:
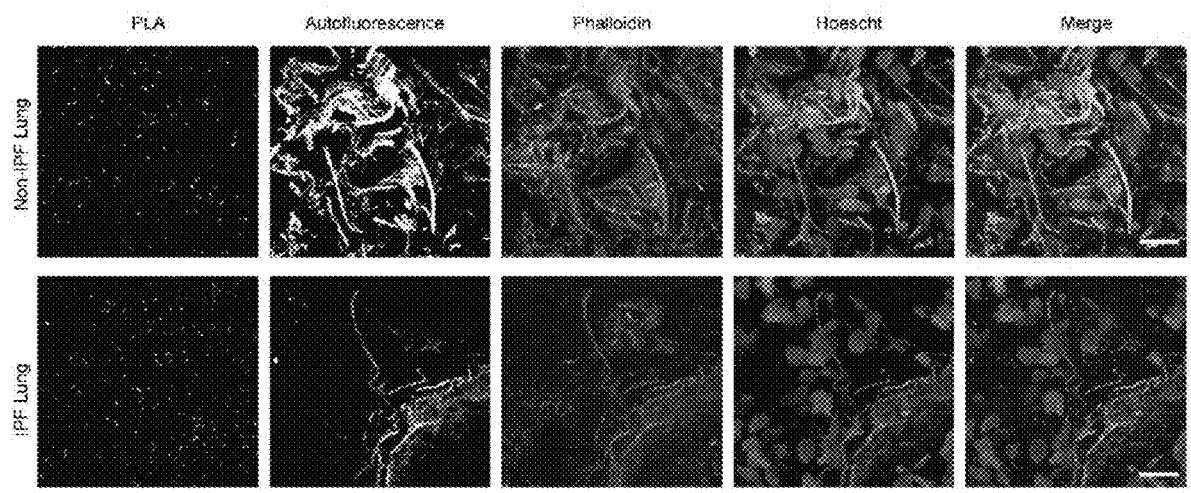
FIGS. 6A through 6D show that LEMD3-Smad2/3 PLA interactions are more cytoplasmic and more varied in frequency in IPF vs. non-IPF human lung tissue.
Figure 6B:
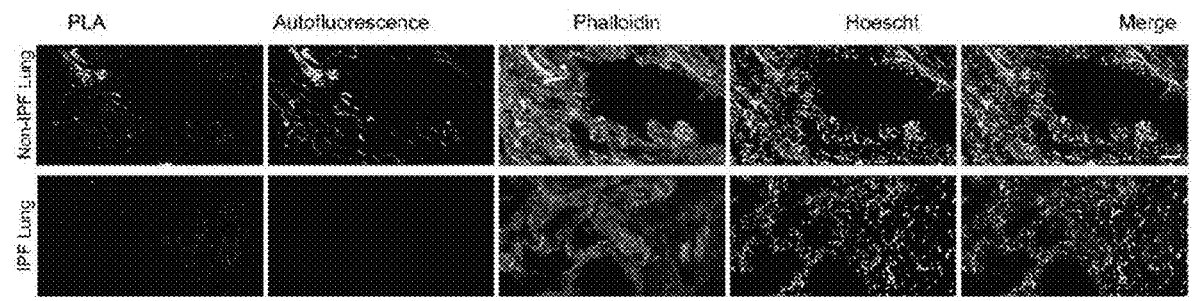
Figure 6C:
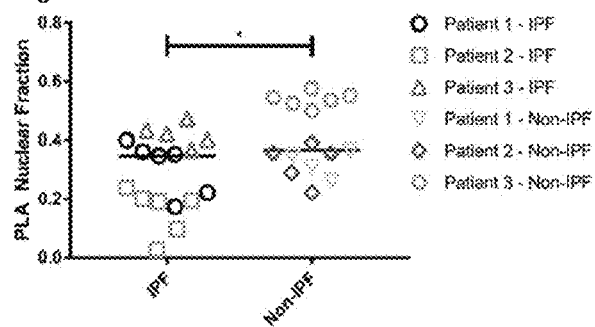

LEMD3-SMAD2/3 Complexes are More Cytosolic and their Frequencies are More Varied in IPF Biopsies than Non-IPF Biopsies We sought to validate our in vitro findings in human lung core biopsies from six patients (three with and three without IPF). IPF patients had significantly more cytosolic LEMD3-Smad2/3 interactions than non-IPF patients (p=0.0307, FIGS. 6A & 6C). These data are compelling because they connect the cytoplasmic PLA localization trend seen with increasing stiffness in vitro in FIG. 2D and the pattern observed in fibrosed relative to non-fibrotic human tissue ex vivo. Additionally, these data directly demonstrate that extra-nuclear LEMD3-Smad2/3 interactions occur in human lung tissue, which we also discovered in FIGS. 2A-2G, indicating that extra-nuclear LEMD3 is not an artifact of in vitro culture.

Figure 6D:
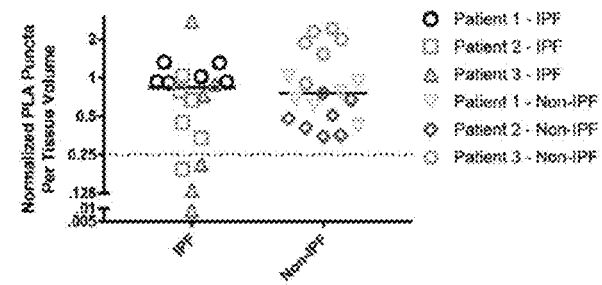

Patients with IPF also had a slightly higher median frequency of LEMD3-Smad2/3 interactions relative to patients without IPF (FIG. 6D, p=0.5783). However, while each non-IPF patient had a fairly consistent LEMD3-Smad2/3 interaction "set-point," IPF patients displayed a higher degree of intra-patient heterogeneity across their sampled tissue regions (67% vs. 30% average coefficient of variance for IPF and non-IPF patients, respectively). Overall, the whole IPF data set had a higher degree of kurtosis (4.765 vs. −0.1391 for IPF and non-IPF patients, respectively), indicating that more of the LEMD3-Smad2/3 variance in IPF tissue comes from extreme deviations in interaction frequency. In particular, ~22% of tissue regions in IPF patients had uniquely low LEMD3-Smad2/3 interaction rates (<25% the mean interaction frequency), not observed in non-IPF tissue. Previous micro-mechanical investigations of IPF tissue revealed a high degree of spatial heterogeneity to tissue stiffness in IPF lungs. (43) Our findings were consistent with the interpretation that spatially heterogeneous regions of fibrosis in the IPF tissue create both in increased variability in the LEMD3-Smad2/3 interaction rate and regions of locally lower LEMD3-Smad2/3 interactions. These data in aggregate showed that LEMD3 regulation of TGFβ through Smad2/3 is locally diminished in IPF tissue relative to non-IPF tissue and that LEMD3's role is not confined to the nucleus in human tissue.

Discussion of Examples

Figure 7:
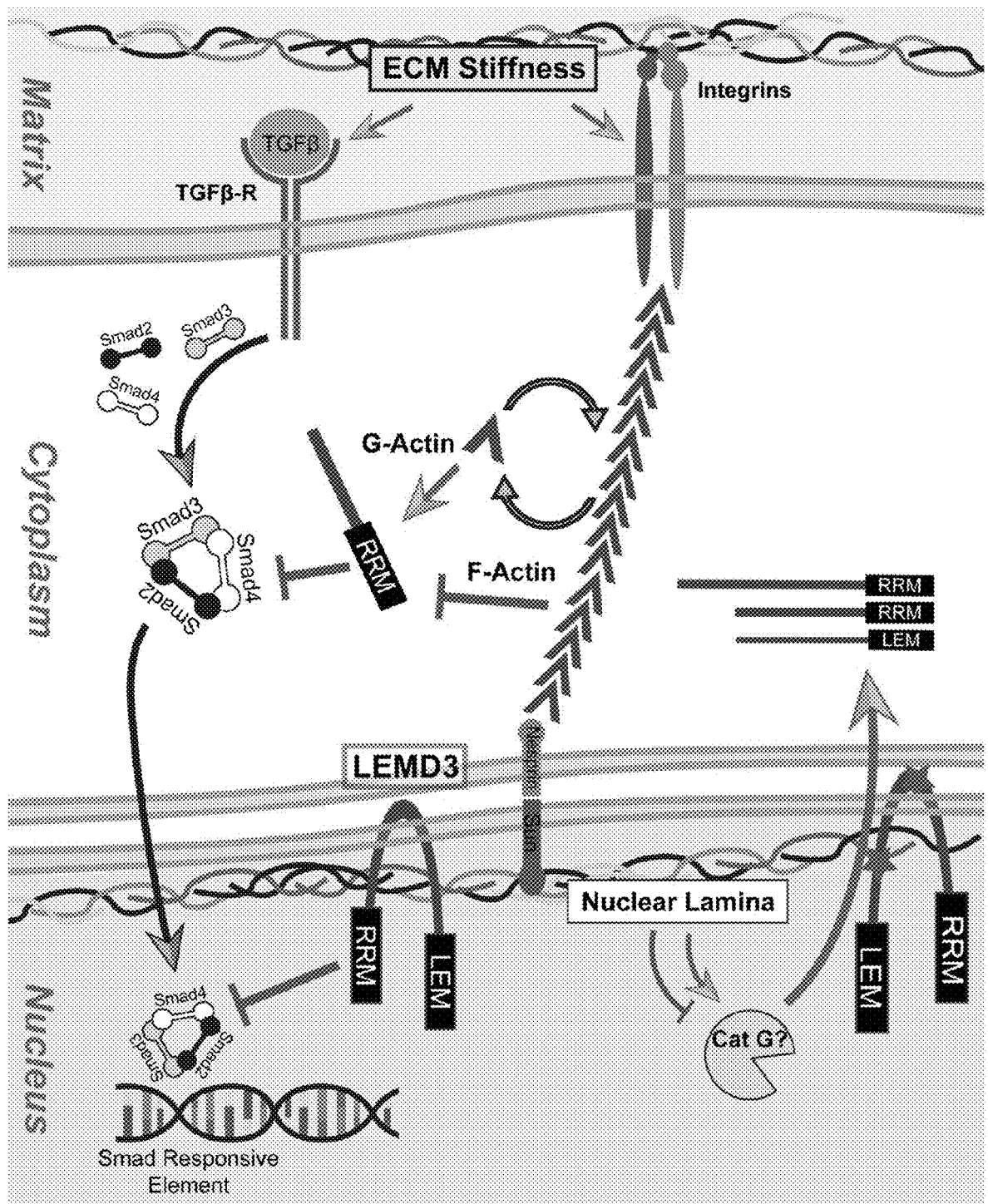
FIG. 7 is a summary cartoon showing mechanical cues from the extracellular matrix potentiate TGFβ activation, which ultimately drives the phosphorylation-dependent formation of Smad2/3/4 complexes. These complexes translocate to Smad Response Elements in the nucleus and facilitate the transcription of TGFβ-dependent genes. LEMD3 antagonizes this TGFβ/Smad2/3 signaling in a stiffness-dependent fashion, altering the stiffness-response of fibroblasts to activated TGFβ. LEMD3 achieves this by binding both Smad2/3 and PPM1α, a protein phosphatase previously shown to be coordinated by LEMD3, both in the nucleus and in the cytosol. Cytosolic LEMD3 fragments are post-translationally generated at two sites, which separate the nuclear localizing LEM domain or the Smad2/3 interacting RRM domain. Processing at the nucleoplasmic site (bottom red star) generates a LEM- and RRM-containing fragment, which is reduced in abundance by serine protease inhibitors but has differential responses to lamin phosphorylation inhibitors. Both nuclear and cytosolic LEMD3-Smad2/3 complexes are inhibited by actin polymerization, which is driven by mechanical cues from the matrix, thereby connecting ECM mechanics to the inhibition of an inhibitor of Smad2/3. Inhibitory interactions are shown with red block-end arrows while activating signals are denoted with green arrows. Black arrows indicate translocation. Abbreviations: Cat G: Cathepsin G; RRM: RNA Recognition Motif, LEM: Lap2b-Emerin-MAN1 domain; TGFβ-R: TGFβ receptor; PPM1α: Protein phosphatase, $Mg^{2+}/Mn^{2+}$ Dependent 1α.

The medical management of fibrotic diseases, such as pulmonary fibrosis, has enjoyed recent success with the approval of pirfenidone, an "anti-fibrotic agent," and nintedanib, an inhibitor of multiple tyrosine kinase receptors, after years of failed clinical trials with a variety of other agents including anti-inflammatory and anti-oxidant drugs. (4, 6, 50, 51) Subsequent study of the mechanisms of pirfenidone has shown that pirfenidone antagonizes fibrotic progression in part by inhibiting the synthesis of TGFβ (5, 7), which is preferentially activated in fibrotic matrices. (8, 9) While pirfenidone may successfully decrease the supply of TGFβ available in fibrotic pathology, ours and others' findings indicate that the fibrotic matrix also potentiates cellular responses (e.g. synthesis of extracellular matrix and increased cellular contractility) to remaining TGFβ. (10-13) We focused on the role of LEMD3 in this matrix-driven sensitization and a graphical summary of our working model for LEMD3-Smad2/3 stiffness-driven interactions is shown in FIG. 7. We showed in vitro that LEMD3 over-expression antagonized TGFβ-driven transcription and "stiff-shifts" the responsiveness of these fibroblasts to TGFβ while LEMD3 knockdown by siRNA "soft-shifts" the mechanical response to TGFβ and potentiates TGFβ signaling. We also showed in vitro that LEMD3-Smad2/3 interactions are inhibited and cytoplasmically shifted with increasing substrate stiffness and actin polymerization. Ex vivo, we identified these same phenotypic correlates in IPF biopsies relative to non-IPF tissue: IPF tissue had a pronounced cytoplasmic shift in PLA subcellular localization; and, ≈22% of IPF tissue regions had a unique reduction in LEMD3-Smad2/3 interactions relative to non-IPF tissue and a higher degree of variation in the LEMD3-Smad2/3 interaction rate across various tissue regions, both in individual patients and overall. These low interaction regions in IPF are not likely attributable to changes in overall LEMD3 abundance in pathology. Ours and others' data showed that full length LEMD3 was not regulated by ECM stiffness at the mRNA or protein level in vitro for endogenous LEMD3 (FIGS. 14A and 14B) or for recombinant LEMD3 (FIGS. 13A and 13B). (52, 53) Moreover, IPF patients do not show evidence of altered LEMD3 transcription in either microarray or NGS sequencing of IPF and control patients. (54-56)

Supporting our discovery of LEMD3-Smad2/3 cytoplasmic interactions, we have discovered here that LEMD3 was post-translationally cleaved at two sites and have implicated serine proteases (possibly cathepsin G) in the generation of C-terminal fragments that lack the necessary LEM domain for nuclear targeting. (33, 34, 57) We have also shown that a C-terminal fragment of LEMD3 bound Smad2/3 throughout the cell, associated with PPM1α, and antagonized Smad2/3-Smad4 complex abundance. These results were consistent with previous studies showing that the C-terminal RRM domain is sufficient for LEMD3's antagonism of Smad2/3. (16, 18, 19, 21, 41)

However, the underlying mechanism for a cytoplasmic shift in LEMD3-Smad2/3 interactions with increasing substrate stiffness in vitro and in IPF patient ex vivo is not clear. In vivo, there is strong evidence for an altered and generally more active serine (58), cysteine (59, 60), and matrix metalloproteinases (61-65) landscape in IPF tissue, though much of the attention has focused on extra-cellular proteolysis. This more pronounced proteolytic environment could contribute to the cytoplasmic shift seen in IPF patients in our study. In vitro, we found that stiffness representative of scarred tissue in IPF (25 kPa) and physiologic lung tissue (1 kPa) produced statistically similar abundances of all the LEMD3 fragments we identified (FIGS. 13A-13B). However, the 46 kDa fragment was nearly twice as abundant on 25 kPa matrices, prompting a need for further investigation. Overall, we have demonstrated that LEMD3 sits at an interesting intersection of mechanical and biochemical cues in pulmonary fibrosis and LEMD3 expression may be a promising adjunctive avenue for addressing fibrosis-driven cellular sensitivity to TGFβ in combination with pirfenidone.

Our original hypothesis for the stiffness regulation of LEMD3-Smad2/3 complexes was that LEMD3's affinity for Smad2/3 would be negatively regulated by biophysical stress from the actin network transmitted to LEMD3 through the LINC-lamina-LEM set of complexes. However, this hypothesis requires critical re-evaluation in light of our discovery of cytosolic LEMD3 fragments that bind Smad2/3 and the apparent lack of efficacy of cytosol-nuclear and lamin-LEM disrupting constructs (DN-Kash and DN-LEM) in decreasing LEMD3-Smad2/3 complex formation in the nucleus. We have also observed that LEMD3-Smad2/3 complexes are negatively correlated to actin polymerization. However, it is not obvious how actin polymerization itself would directly modulate LEMD3-Smad2/3 complex formation given that neither LEMD3 nor Smad2/3 has a known direct association with actin. One parsimonious explanation would be that LEMD3 competes for Smad2/3 binding with other actin-regulated proteins, namely, yes-associated protein (YAP)/transcriptional coactivator with PDZ-binding motif (TAZ) and/or Rho-associated protein kinase (ROCK). YAP/7AZ and ROCK bind Smad2/3 and have been shown to be necessary for nuclear accumulation of Smad2/3 in response to TGFβ stimulus. (13, 66-69) ROCK inhibition has been shown to modulate phosphorylation in Smad3's linker region (Ser203, Ser207, Ser212) (66), while TAZ has been shown to bind to the MH1 domain of Smad2. (67) Interestingly, yeast two-hybrid assays indicate that LEMD3 binds to the MH2 domain of both Smad2 and Smad3 (14). While YAP/TAZ and LEMD3 seem to bind different locations in Smads, YAP/TAZ have been shown to negatively regulate the Smad binding of forkhead box protein H1 (FOXH1), which competes for binding to Smad2/3's MH2 domain with LEMD3 in embryonic stem cell CHIP assays (16, 70). These data indicate that YAP/TAZ, in particular, are promising candidates for modulating LEMD3's ability to bind Smad2/3 in an actin polymerization-dependent fashion.

LEMD3 is also directly implicated in the development of Buschke-Ollendorff syndrome (BOS) with and without melorheostosis. Our findings that LEMD3 was post-translationally processed proteolytically and has cytosolic forms raises new questions regarding the pathogenesis of BOS. Many of the identified BOS patients possess nonsense or splice-site mutations which eliminate the Smad-binding C-terminal end of LEMD3. (20, 24-31) Interestingly, there are a five missense mutations of unknown clinical significance associated with BOS in NCBI's ClinVar database, which are associated with one of the two deletion mutants (p.Δ294-325 and p.Δ579-647) identified in this study. (71) These missense mutations could suggest that alterations to the fragment controlling regions of LEMD3 might play a role in the development of BOS. Additionally, our finding that LEMD3 was processed by a serine protease and the 26S proteosome might suggest ad-ditional targets/mechanisms in individuals with BOS who lack mutations in LEMD3. (32)

Finally, we have characterized several N- and C-terminal LEMD3 fragments and demonstrated their varying sensitivities to: 1) genetic perturbation through deletion mutants; 2) serine (DCI), cathepsin G and 26S proteosome (MG-132) inhibitors; 3) lamin integrity/disassembly through cdk1 inhibition; and 4) substrate stiffness. One particular pair of fragments, the 60 kDa N-terminal FLAG and 46 kDa C-terminal V5 fragments, are particularly interesting because they are both sensitive to the same mutation region (p.Δ294-325), both fragments' abundance is reduced with respect to DCI and MG-132 treatment, and they plausibly sum to the mass of full length LEMD3. However, these two fragments are differentially regulated by integrity of the lamin network (following inhibition of cdk1 by roscovitine) and by cathepsin G inhibition, making it less likely that these fragments are generated in a concerted proteolytic reaction. Additionally, we do not have a straight-forward explanation relating the position of our deletion mutations and the fragments' sizes they seemingly control. It is not possible to direct align our western blot fragment data and mass spec data because of the unknown distributions of post-translational modifications in LEMD3; however, the fragments' relative masses controlled by either deletion mutant do not logically correspond with expected size of products from cleavage in those areas.

This is, to our knowledge, the first report of an integral, inner nuclear membrane protein processed proteolytically into cytosolic forms. However, our observations fit a broader pattern of a more locationally dispersed role for nuclear envelope integral proteins. Several integral members of the nuclear membrane have alternative splice forms that both include and omit their trans-membrane domain(s), including nesprin, lamina-associated polypeptide 2, (LAP2), torsin-1α-interacting protein 1 (LAP1), and nurim. (72-75) Moreover, some "localized" elements of the nuclear envelope have been found dispersed throughout the cytosol based on the cellular context. For example, nesprins, structural elements of the outer nuclear membrane that link the cytoskeleton and nucleus are restricted to the nuclear envelop in myoblasts but not in differentiated myotubes (76, 77), and certain nesprin isoforms are also de-compartmentalized during muscle regeneration in Duchenne muscular dystrophy. (77) Additionally, alternatively spliced, "KASH-less" nesprins, which lack the nuclear envelope anchoring domain, KASH, have recently been linked to a variety of cytosolic locations, including focal adhesions and actin stress fibers (72), Golgi bodies, (78) and RNA-processing bodies. (79, 80) Our findings expand on the observed mechanisms that regulate the localization of nuclear envelope proteins in the cell.

TABLE 3

Oligos used in this work for SDM, siRNA, or RT-qPCR

| SEQ ID No. | Oligo Name | 5'-3' Sequence | Purpose | Tm | Concentration Used | Vendor | Cat # |
|---|---|---|---|---|---|---|---|
| 1 | siLemD1 | GGAUAGAGCUGUUGACUUC | siRNA anti-LEMD3 | NA | Pooled to 200 nM | Dharmacon | siGENOME SMARTpool siRNA D-006306-01 |
| 2 | siLEMD2 | GAACUUCUCCAGCAAUUUA | siRNA anti-LEMD3 | NA | | Dharmacon | siGENOME SMARTpool siRNA D-006306-02 |
| 3 | siLEMD3 | GGAAUAAGGUGUGUUGGUU | siRNA anti-LEMD3 | NA | | Dharmacon | siGENOME SMARTpool siRNA D-006306-03 |
| 4 | siLEMD4 | CAAGGCAGAUGUAUGAUAU | siRNA anti-LEMD3 | NA | | Dharmacon | siGENOME SMARTpool siRNA D-006306-04 |
| 5 | siGFP | CAAGCUGACCCUGAAGUUCUU | siRNA Control | NA | 200 nM | IDT | Gift from Dr. MG Finn's Lab |
| 6 | insV5 For | CTGCTGGGCTGGATAGCACCTGAAAAGCTCGAGCTCGA | p.S931-Ter932insGKPIPNPL LGLDST in pSVK3-FLAG-LEMD3 | 68C | 500 nM | IDT | Custom |
| 7 | insV5 Rev | CGGGTTCGAATCGGTTTGCCGGAACTTCCTTGAGAATTGG | | | 500 nM | IDT | Custom |
| 8 | LEM GA For | TTAAATGATCCCGCCACCATGGCGGCGGCA | DN LEM Construction from pCDH-EF1-MCS1-puro-KASH-mCherry | 54C | 500 nM | IDT | Custom |
| 9 | LEM GA Rev | TGCTCACCATTCGATATTTCATGTAACGCAG | | 52C | 500 nM | IDT | Custom |
| 10 | mCherry GA For | GAAATATCGAATGGTGAGCAAGGGCGAG | | 58C | 500 nM | IDT | Custom |
| 11 | mCherry GA Rev | ATCCTTGCGCCGCTCAC | | 62C | 500 nM | IDT | Custom |
| 12 | del294-325 For | CTGGAGACTTCAGTTCAGGGAG | p.delQ294-R325 in pSVK3-FLAG-LEMD3-V5 | 68C | 500 nM | IDT | Custom |
| 13 | del294-325 Rev | TCTGCTGGAGGCCACGTC | | | 500 nM | IDT | Custom |
| 14 | del579-647 For | TTTGTTACTGTAACTCACAG | p.delE579-A647 in pSVK3-FLAG-LEMD3-V5 | 57C | 500 nM | IDT | Custom |
| 15 | del579-647 Rev | TTGAACAGAAAGCGTTCTTTG | | | 500 nM | IDT | Custom |
| 16 | del21-668 For | CTGCGTTACATGAAATATCG | p.delM21-V668 in pSVK3-FLAG-LEMD3-V5 | 60C | 500 nM | IDT | Custom |
| 17 | del21-668 Rev | TTTCTCGTCCGAATTCCTG | | | 500 nM | IDT | Custom |
| 18 | qLEMD3 For | TTTTCGACGTGCTTTTGTTACTG | RT-qPCR - Human LEMD3, Exons 6-7 | 60C | 250 nM | IDT | Hs.PT.58.38449009 |
| 19 | qLEMD3 Rev | TGTTTCCTCCTCTTCTTTTTGTCC | | | 250 nM | IDT | |
| 20 | q18S For | GTAACCCGTTGAACCCCATT | RT-qPCR - Human 18S | 60C | 250 nM | IDT | Originally found in (83) |
| 21 | q18S Rev | CCATCCAATCGGTAGTAGCG | | | 250 nM | IDT | |
| 22 | qACTB For | AGGCACCAGGGCGTGAT | RT-qPCR - Human β-Actin | 60C | 250 nM | IDT | Originally found in (84) |
| 23 | qACTB Rev | GCCCACATAGGAATCCTTCTGAC | | | 250 nM | IDT | |

TABLE 4

Primary, secondary and other antibodies used in this work

|  | Target | Clone | Host | Application WB | IF | PLA | Other | Vendor | Cat # |
|---|---|---|---|---|---|---|---|---|---|
| Primary | LEMD3 | 4E1 | Mouse | 1:1000 | | 1:1000 (cells), 1:100 (tissue), used with EPR19557-4 & D27114 | | LsBio | LS-C114872 |
| | LEMD3 | Polyclonal | Rabbit | | | 1:1000, used with 7F12 | | Abcam | 124148 |
| | V5 | V5-10 | Mouse | 1:1000 | | | | Sigma | V8012 |
| | V5 | Polyclonal | Rabbit | | | 1:2000, used with 18/Smad213; 1:1500, used with 7F12 | | Abcam | ab9116 |
| | 647 labeled V5 | 1036H | Rabbit | | 1:200 | | | R&D Systems | FAB8926R |
| | PPM1α | 7F12 | Mouse | | | 1:1000, used with LEMD3 Poly; 1:1500, used with V5 Poly | | Abcam | 135249 |
| | Smad4 | Polyclonal | Rabbit | | | 1:1000, used with 18/Smad2/3 | | CST | 9515 |
| | Smad2/3 | 18/Smad2/3 | Mouse | | | 1:2000, used with Abcam ab9116; 1:1000, used with Smad4 poly | | BD Bioscience | 610842 |
| | Smad2/3 | EPR19557-4 | Rabbit | | | 1:1000 (cells), 1:100 (tissue), used with 4E1 | | Abcam | ab202445 |
| | phospho-Smad2/3 | D27F4 | Rabbit | 1:1000 | | 1:1000, used with 4E1 | | CST | #8828 |
| | FLAG | Polyclonal | Rabbit | 1:1000 | 1:1000 | | | Sigma | F7425 |
| | GAPDH | D-6 | Mouse | 1:1000 | | | | Santa Cruz | sc166545 |
| | Lamin A/C | EPR4068 | Rabbit | 1:1000 | | | | Abcam | ab108922 |
| Secondary | Goat αMouse-HRP | N/A | Goat | 1:15000 | | | | Abcam | ab7023 |
| | Goat αRabbit-HRP | N/A | Goat | 1:15000 | | | | ThermoFisher | A-27036 |
| | Donkey αRabbit-IR680 | N/A | Donkey | 1:20000 | | | | Licor | 926-68073 |
| | Donkey αMouse-CW800 | N/A | Donkey | 1:20000 | | | | Licor | 926-32212 |
| | Goat αRabbit-546 | N/A | Goat | | 1:500 | | | ThermoFisher | A-11010 |
| Blocking | Donkey αRabbit | N/A | Donkey | | | | 1:10 | Jackson ImmunoResearh | 711-066-152 |

TABLE 5

Chemicals and recombinant proteins used in this work

| Name | CAS | Working Concentration | Solvent | Use | Vendor | Cat # |
|---|---|---|---|---|---|---|
| Cytochalasin D | 22144-77-0 | 2 μM | DMSO | Stablizes g-actin | Sigma | C8273 |
| Blebbistatin | 674289-55-5 | 2 μM | DMSO | Inhibits myosin II | Sigma | 203389 |
| Jasplakinolide | 102396-24-7 | 100-200 nM | DMSO | Stablizes f-actin | Enzo | ALX-350-275 |
| E-64D | 88321-09-9 | 2-40 μm | DMSO | Irreversible cystein protease inhibitor: calpain, papain, actinidase, cathepsins B, H, and L | Sigma | E8640 |
| E-64 | 66701-25-5 | 10-100 μM | DMSO | Irreversible cystein protease inhibitor: calpain, papain, actinidase, cathepsins B, H, and L | Sigma | E3132 |
| DCI | 51050-59-0 | 10-100 μM | DMSO | Irreversible serine protease/esterase inihibitor: cathepsin G, elastase, thrombin, plasmin, factor Xa & X11a, granzymes A, B, and H | Sigma | D7910 |
| MMPi III | 927827-98-3 | 1-20 μM | DMSO | Reversible MMP inhibitor: MMP1, MMP2, MMP3, MMP7, MMP13 | Millipore | 444264 |
| MG-132 | 133407-82-6 | 10 μM | DMSO | Inhibits 26S proteosome | Sigma | M7449 |
| Roscotine | 186692-46-6 | 0.1-35 μM | DMSO | Inhibits cdc2/cyclin B, cdk2/cyclin A, cdk2/cyclin E, cdk5/p35 | Tocris | 1332 |
| TGFβ | N/A | 50-1000 pg/mL | 4 mM HCL with 10% BSA | Recombinant human TGF-β | R&D Systems | 240-B |

TABLE 6

LEMD3 Sequences

| SEQ ID No. | Name | Sequence |
|---|---|---|
| 24 | Full LEMD3, human consensus | MAAAAASAPQQLSDEELFSQLRRYGLSPGPVTESTRPVYLKKLKKLREEEQQQHRSGGRGNKTRNSNNNNTAAATVAAAGPAAAAAAGMG VRPVSGDLSYLRTPGGLCRISASGPESLLGGPGGASAAPAAGSKVLLGFSSDESDVEASPRDQAGGGGRKDRASLQYRGLKAPPAPLAASEVT NSNSAERRKPHSWWGARRPAGPELQTPPGKDGAVEDEEGEGEDGEEERDPETEEPLWASRTVNGSRLVPYSCRENYSDSEEEDDDDVASSRQ VLKDDSLSRHRPRRTHSKPLPPLTAKSAGGRLETSVQGGGGLAMNDRAAAAGSLDRSRNLEEAAAAEQGGGCDQVDSSPVPRYRVNAKKLT PLLPPPLTDMDSTLDSSTGSLLKTNNHIGGGAFSVDSPRIYSNSLPPSAAVAASSSLRINHANHTGSNHTYLKNTYNKPKLSEPEEELLQQFK REEVSPTGSFSAHYLSMFLLTAACLFFLILGLTYLGMRGTGVSEDGELSIENPFGETFGKIQESEKTLMMNTLYKLHDRLAQLAGDHECGSSS QRTLSVQEAAAYLKDLGPEYEGIFNTSLQWILENGKDVGIRCVGFGPEEELTNITDVQFLQSTRPLMSFWCRFRRAFVTVTHRLLLLCLGVVM VCVVLRYMKYRWTKEEEETRQMYDMVVKIIDVLRSHNEACQENKDLQPYMPIPHVRDSLIQPHDRKKMKKVWDRAVDFLAANESRVRTETRRI GGADFLVWRWIQPSASCDKILVIPSKVWQGQAFHLDRRNSPPNSLTPCLKIRNMFDPVMEIGDQWHLAIQEAILEKCSDNDGIVHIAVDKNSR EGCVYVKCLSPEYAGKAFKALHGSWFDGKLVTVKYLRLDRYHHRFPQALTSNTPLKPSNKHMNSMSHLRLRTGLTNSQGSS |
| 25 | C-Terminal Fragment, CTF | MAAAAASAPQQLSDEELFSQRDSLIQPHDRKKMKKVWDRAVDFLAANESRVRTETRRIGGADFLVWRWIQPSASCDKILVIPSKVWQGQAF HLDRRNSPPNSLTPCLKIRNMFDPVMEIGDQWHLAIQEAILEKCSDNDGIVHIAVDKNSREGCVYVKCLSPEYAGKAFKALHGSWFDGKLVT VKYLRLDRYHHRFPQALTSNTPLKPSNKHMNSMSHLRLRTGLINSQGSS |
| 26 | Full LEMD3 DNA | ATGGCGGCGGCAGCAGCTTCGGCGCCTCAGCAGCTCTCGGATGAGGAGCTTTTCTCTCAGCTCCGCCGTTACGGCCTGTCTCCCGGACC AGTGACGGAGAGCACCCGCCCGGTCTACCTCAAGAAGCTGAAGAAGCTTCGAGAGGAAGAGCAGCAACAGCACCGGTCAGGGGGCCG CGGCAACAAGACGCGGAACAGTAATAACAATAACACGGCAGCCGCCACGGTCGCAGCCGCGGGACGCGGCGGCGGCGGCTGCGG GATGGGGGTCCGGCCGGTCTCGGGCGACCTCTCCTACTTACGGACTCCTGGGGGCCTGTGCCGAATCTCGGCCTCTGGCCAGAGAGCC TCCTGGGAGGGCCCGGGGGCGCCTCCGCCGCCCCCGCGGCTGGCAGCAAAGTGCTGCTGGGCTTCAGCTCGGACGAGTCGGACGTGGA GGCCAGTCCCCGGGACCAGGCCGGCGGCGGCGGGAGGAAAGACCGGGCTTCGCTCCAGTACCGCGGGCTCAAAGCGCCGCCGGCGCC CCTGGCCGCCAGCGAGGTGACTAACAGCGCTGAGCGGAGGAAGCCCCACTCGTGGTGGGGGCGCAGGAGGCCGGCGGGCCC CGAGCTGCAGACCCCGCCGGGGAAAGATGGAGCAGTGGAGGACGAGGAAGGGGAGGGAGGAGGCGGTGAGGAGAGGGACCCGGAGA CCGAGGAGCCGCTCTGGGCGAGCCGGACCGTGAATGGCAGCCGGCTTGTCCCCTACAGCTGCCGGGAAAACTATTCGGACTCAGAGGA AGAGGACGACGACGACGTGGCCTCCAGCAGACAGGTATTAAAGGACGACTCCCTTTCCCGGCATCGGCCCAGACGAACCCATAGTAAG CCTCTCCCCCGCTGACTGCTAAATCGGCCGGCGGCAGGCTGGAGACTTCAGTTCAGGGAGGGGGAGGACTCGCGATGAATGACAGGG CGGCGGCTGCCGGGAGTCTAGACAGGAGCCGAAACCTCGAAGAGGCGGCGGCCGCGGAGCAGGGAGGAGGGTGTGATCAAGTGGACT CCAGCCCCGTTCCTAGATACCGTGTTAACGCTAAGAAACTGACCCCTCTCCTGCCCCCGCCACTTACTGACATGGACTCAACCTTGATT CGTCAACAGGCTCCCTTCTGAAAACCAATAATCATATTGGCGGTGGGGCCTTCAGTGTGGACTCCCCCAGGATTTATTCTAACAGTCTCC CTCCCAGTGCGGCGGTGGCCGCCTCTAGTTCACTCAGGATCAATCACGCCAATCATCGGGCTCCAATCATACCTACCTGAAAACACA TACAACAAACCGAAGCTTTCCGAACCCGAAGAGGAACTTCTCCAGCAATTTAAACGGGAGGAGGTGTCCCCAACAGGGAGTTTCAGTG CCCACTACTTGTCGATGTTTCTCTTAACTGCTGCCTGCTTATTTTTCCTAATACTGGGACTGACTTACCTAGGAATGAGAGGGACAGGAG TATCTGAGGATGGAGAACTCAGCATAGAAAACCCTTTGGTGAAAACATTTGGAAAAATACAAGAAAGTGAAAAACTCTTATGATGAA CACATTATATAAGCTTCATGATCGATTGGCACAGCTTCAGGAGATCATGAATGTGGCAGTTCTAGTCAAAAACGCTTTCTGTTCAAG AGGCAGCTGCGTATTTAAAAGATTTAGGTCCTGAATATGAAGGTATATTTAACACTTCATTGCAGTGGATCTTAGAAAATGGAAAAGAT GTTGGAATAAGGTGTGTTGGTTTTGGCCCTGAGGAAGAATTGACAAATATAACTGATGTGCAGTTTTTACAGTCCACAAGACCACTGAT GTCTTTTTGGTGTCGTTTTCGACGTGCTTTTGTTACTGTAACTCACAGATTATTGTTGTTATGCTTAGGTGTAGTGATGGTTTGTGTCGTTC TGCGTTACATGAAATATCGATGGACAAAAGAAGAGGAGGAAACAAGGCAGATGTATGATATGGTGGTAAAGATTATAGATGTTTTACG AAGTCATAATGAAGCCTGCCAGGAAAACAAAGATTTACAACCTTACATGCCTATTCCACATGTACGCGATTCCTTAATACAGCCTCATG ACAGGAAAAAAATGAAGAAAGTCTGGGATAGAGCTGTTGACTTCCTTGCTGCTAATGAGTCTAGAGTTCGCACGGAAACACGAAGAAT AGGTGGTGCAGATTTTCTGGTTTGGCGGTGGATCCAGCCTTCTGCATCCTGTGACAAAATATTAGTTATACCTTCTAAAGTATGGCAAGG TCAAGCATTTCATTTAGATAGAAGAAATTCACCACCAAATAGTTTGACACCGTGTCTAAAGATTCGGAATATGTTTGATCCCGTTATGGA AATAGGGGATCAGTGGCATTTGGCAATTCAAGAAGCAATTTTAGAAAATGCAGTGATAATGATGGCATTGTTCACATTGCAGTAGACA AAAATTCACGTGAGGGTTGTGTATATGTTAAATGTCTGTCTCCAGAATATGCTGGAAAGGCTTTTAAAGCATTGCATGGCTCTTGGTTTG ATGGGAAATTGGTTACAGTAAAATATTTACGACTAGATAGATACCACCATCGCTTTCCCCAGGCTCTCACTTCCAACACTCCATTGAAGC CATCAAATAAACATATGAACTCCATGTCTCATCTTCGTCTTCGGACTGGCCTAACCAATTCTCAAGGAAGTTCC |
| 27 | CTF DNA | ATGGCGGCGGCAGCAGCTTCGGCGCCTCAGCAGCTCTCGGATGAGGAGCTTTTCTCTCAG CGCGATTCCTTAATACAGCCTCATGACAGGAAAAAAATGAAGAAAGTCTGGGATAGAGCTGTTGACTTCCTTGCTGCTAATGAGTCTAG AGTTCGCACGGAAACACGAAGAATAGGTGGTGCAGATTTTCTGGTTTGGCGGTGGATCCAGCCTTCTGCATCCTGTGACAAAATATTAG TTATACCTTCTAAAGTATGGCAAGGTCAAGCATTTCATTTAGATAGAAGAAATTCACCACCAAATAGTTTGACACCGTGTCTAAAGATT CGGAATATGTTTGATCCCGTTATGGAAATAGGGGATCAGTGGCATTTGGCAATTCAAGAAGCAATTTTAGAAAATGCAGTGATAATGA TGGCATTGTTCACATTGCAGTAGACAAAAATTCACGTGAGGGTTGTGTATATGTTAAATGTCTGTCTCCAGAATATGCTGGAAAGGCTTT TAAAGCATTGCATGGCTCTTGGTTTGATGGGAAATTGGTTACAGTAAAATATTTACGACTAGATAGATACCACCATCGCTTTCCCCAGGC TCTCACTTCCAACACTCCATTGAAGCCATCAAATAAACATATGAACTCCATGTCTCATCTTCGTCTTCGGACTGGCCTAACCAATTCTCA AGGAAGTTCC |
| 28 | LEMD3 RRM DOMAIN, DNA | GTACGCGATTCCTTAATACAGCCTCATGACAGGAAAAAAATGAAGAAAGTCTGGGATAGAGCTGTTGACTTCCTTGCTGCTAATGAGTC TAGAGTTCGCACGGAAACACGAAGAATAGGTGGTGCAGATTTTCTGGTTTGGCGGTGGATCCAGCCTTCTGCATCCTGTGACAAAATAT TAGTTATACCTTCTAAAGTATGGCAAGGTCAAGCATTTCATTTAGATAGAAGAAATTCACCACCAAATAGTTTGACACCGTGTCTAAAG ATTCGGAATATGTTTGATCCCGTTATGGAAATAGGGGATCAGTGGCATTTGGCAATTCAAGAAGCAATTTTAGAAAATGCAGTGATAA TGATGGCATTGTTCACATTGCAGTAGACAAAAATTCACGTGAGGGTTGTGTATATGTTAAATGTCTGTCTCCAGAATATGCTGGAAAGG CTTTTAAAGCATTGCATGGCTCTTGGTTTGATGGGAAATTGGTTACAGTAAAATATTTACGACTAGATAGATACCACCATCGCTTTCCCC AGGCTCTCACTTCCAACACTCCATTGAAGCCATCAAATAAACATATGAACTCCATGTCTCATCTTCGTCTTCGGACTGGCCTAACCAATT CTCAAGGAAGTTCC |

TABLE 6-continued

LEMD3 Sequences

| SEQ ID No. | Name | Sequence |
|---|---|---|
| 29 | LEMD3 RRM DO- MAIN, AA | VRDSLIQPHDRKKMKKVWDRAVDFLAANESRVRTETRRIGGADFLVWRWIQPSASCDKILVIPSKVWQGQAFHLDRRNSPPNSLTPCLKIRN MFDPVMEIGDQWHLAIQEAILEKCSDNDGIVHIAVDKNSREGCVYVKCLSPEYAGKAFKALHGSWFDGKLVTVKYLRLDRYHHRFPQALTS NTPLKPSNKHMNSMSHLRLRTGLTNSQGSS |

REFERENCES

All references listed in the instant disclosure, including but not limited to all patents, patent applications and publications thereof, scientific journal articles, and database entries (including but not limited to UniProt, EMBL, and GENBANK® biosequence database entries and including all annotations available therein) are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. Applicants reserve the right to challenge the accuracy and pertinence of any cited reference.

1. Zeisberg, M. and Kalluri, R. (2013) Cellular mechanisms of tissue fibrosis. 1. common and organ-specific mechanisms associated with tissue fibrosis. *Am J Physiol Cell Physiol* 304, C216-25, 10.1152/ajpcell.00328.2012
2. Morikawa, M., Derynck, R., and Miyazono, K. (2016) Tgf-beta and the tgf-beta family: Context-dependent roles in cell and tissue physiology. *Cold Spring Harb Perspect Biol* 8, 10.1101/cshper-spect.a021873
3. Walton, K. L., Johnson, K. E., and Harrison, C. A. (2017) Targeting tgf-beta mediated smad signaling for the prevention of fibrosis. *Front Pharmacol* 8, 461, 10.3389/fphar.2017.00461
4. King, T. E., J., Bradford, W. Z., Castro-Bernardini, S., Fagan, E. A., Glaspole, I., Glassberg, M. K., Gorina, E., Hopkins, P. M., Kardatzke, D., Lancaster, L., Lederer, D. J., Nathan, S. D., Pereira, C. A., Sahn, S. A., Sussman, R., Swigris, J. J., Noble, P. W., and Group, A. S. (2014) A phase 3 trial of pirfenidone in patients with idiopathic pulmonary fibrosis. *N Engl J Med* 370, 2083-92.
5. Stahnke, T., Kowtharapu, B. S., Stachs, O., Schmitz, K. P., Wurm, J., Wree, A., Guthoff, R. F., and Hovakimyan, M. (2017) Suppression of tgf-beta pathway by pirfenidone decreases extracel-lular matrix deposition in ocular fibroblasts in vitro. *PLoS One* 12, e0172592, 10.1371/journal.pone.0172592
6. Vancheri, C., Kreuter, M., Richeldi, L., Ryerson, C. J., Valeyre, D., Grutters, J. C., Wiebe, S., Stansen, W., Quaresma, M., Stowasser, S., Wuyts, W. A., and investigators, I. t. (2017) Nintedanib with add-on pirfenidone in idiopathic pulmonary fibrosis: Results of the in journey trial. *Am J Respir Crit Care Med*, 10.1164/rccm.201706-13010C
7. Du, J., Paz, K., Flynn, R., Vulic, A., Robinson, T. M., Lineburg, K. E., Alexander, K. A., Meng, J., Roy, S., Panoskaltsis-Mortari, A., Loschi, M., Hill, G. R., Serody, J. S., Maillard, I., Miklos, D., Koreth, J., Cutler, C. S., Antin, J. H., Ritz, J., MacDonald, K. P., Schacker, T. W., Luznik, L., and Blazar, B. R. (2017) Pirfenidone ameliorates murine chronic gvhd through inhibition of macrophage infiltration and tgf-beta production. *Blood* 129, 2570-2580, 10.1182/blood-2017-01-758854
8. Wipff, P. J., Rifin, D. B., Meister, J. J., and Hinz, B. (2007) Myofibroblast contraction activates latent tgf-beta1 from the extracellular matrix. *J Cell Biol* 179, 1311-23, 10.1083/jcb.200704042
9. Klingberg, F., Chow, M. L., Koehler, A., Boo, S., Buscemi, L., Quinn, T. M., Costell, M., Alman, B. A., Genot, E., and Hinz, B. (2014) Prestress in the extracellular matrix sensitizes latent tgf-beta1 for activation. *J Cell Biol* 207, 283-97, 10.1083/jcb.201402006
10. Olsen, A. L., Bloomer, S. A., Chan, E. P., Gaca, M. D., Georges, P. C., Sackey, B., Uemura, M., Jan-mey, P. A., and Wells, R. G. (2011) Hepatic stellate cells require a stiff environment for myofibroblas-tic differentiation. *Am J Physiol Gastrointest Liver Physiol* 301, G110-8, 10.1152/ajpgi.00412.2010
11. Park, J. S., Chu, J. S., Tsou, A. D., Diop, R., Tang, Z., Wang, A., and Li, S. (2011) The effect of matrix stiffness on the differentiation of mesenchymal stem cells in response to tgf-beta. *Biomaterials* 32, 3921-30, 10.1016/j.biomaterials.2011.02.019
12. Shi, Y., Dong, Y., Duan, Y., Jiang, X., Chen, C., and Deng, L. (2013) Substrate stiffness influences tgf-beta1-induced differentiation of bronchial fibroblasts into myofibroblasts in airway remodeling. *Mol Med Rep* 7, 419-24, 10.3892/mmr.2012.1213
13. Szeto, S. G., Narimatsu, M., Lu, M., He, X., Sidiqi, A. M., Tolosa, M. F., Chan, L., De Freitas, K., Bialik, J. F., Majumder, S., Boo, S., Hinz, B., Dan, Q., Advani, A., John, R., Wrana, J. L., Kapus, A., and Yuen, D. A. (2016) Yap/taz are mechanoregulators of tgf-beta-smad signaling and renal fibrogenesis. *J Am Soc Nephrol* 27, 3117-3128, 10.1681/ASN.2015050499
14. Lin, F., Morrison, J. M., Wu, W., and Worman, H. J. (2005) Man1, an integral protein of the inner nuclear membrane, binds smad2 and smad3 and antagonizes transforming growth factor-beta signaling. *Hum Mol Genet.* 14, 437-45, 10.1093/hmg/ddi040
15. Konde, E., Bourgeois, B., Tellier-Lebegue, C., Wu, W., Perez, J., Caputo, S., Attanda, W., Gasparini, S., Charbonnier, J. B., Gilquin, B., Worman, H. J., and Zinn-Justin, S. (2010) Structural analysis of the smad2-man1 interaction that regulates transforming growth factor-beta signaling at the inner nuclear membrane. *Biochemistry* 49, 8020-32, 10.1021/bi101153w
16. Bourgeois, B., Gilquin, B., Tellier-Lebegue, C., Ostlund, C., Wu, W., Perez, J., El Hage, P., Lallemand, F., Worman, H. J., and Zinn-Justin, S. (2013) Inhibition of tgf-beta signaling at the nuclear envelope: characterization of interactions between man1, smad2 and smad3, and ppm1a. *Sci Signal* 6, ra49, 10.1126/scisignal.2003411

17. Bermeo, S., Al-Saedi, A., Kassem, M., Vidal, C., and Duque, G. (2017) The role of the nuclear envelope protein man1 in mesenchymal stem cell differentiation. *J Cell Biochem.* 118, 4425-4435, 10.1002/jcb.26096

18. Osada, S.-I., Ohmori, S.-y., and Taira, M. (2003) Xman1, an inner nuclear membrane protein, antagonizes bmp signaling by interacting with smad1 in xenopus embryos. *Development* 130, 1783-1794, 10.1242/dev.00401

19. Raju, G. P., Dimova, N., Klein, P. S., and Huang, H. C. (2003) Sane, a novel lem domain protein, regulates bone morphogenetic protein signaling through interaction with smad1. *J Biol Chem* 278, 428-37, 10.1074/jbc.M210505200

20. Hellemans, J., Preobrazhenska, O., Willaert, A., Debeer, P., Verdonk, P. C., Costa, T., Janssens, K., Menten, B., Van Roy, N., Vermeulen, S. J., Savarirayan, R., Van Hul, W., Vanhoenacker, F., Huylebroeck, D., De Paepe, A., Naeyaert, J. M., Vandesompele, J., Speleman, F., Verschueren, K., Coucke, P. J., and Mortier, G. R. (2004) Loss-of-function mutations in lemd3 result in osteopoik-ilosis, buschke-ollendorff syndrome and melorheostosis. *Nat Genet.* 36, 1213-8, 10.1038/ng1453

21. Pan, D., Estevez-Salmeron, L. D., Stroschein, S. L., Zhu, X., He, J., Zhou, S., and Luo, K. (2005) The integral inner nuclear membrane protein man1 physically interacts with the r-smad proteins to repress signaling by the transforming growth factor-beta superfamily of cytokines. *J Biol Chem* 280, 15992-6001, 10.1074/jbc.M411234200

22. Lin, X., Duan, X., Liang, Y.-Y., Su, Y., Wrighton, K. H., Long, J., Hu, M., Davis, C. M., Wang, J., Brunicardi, F. C., Shi, Y., Chen, Y.-G., Meng, A., and Feng, X.-H. (2006) Ppm1a functions as a smad phosphatase to terminate tgfβ signaling. *Cell* 125, 915-928, https://doi.org/10.1016/j.cell.2006.03.044

23. Yadegari, M., Whyte, M. P., Mumm, S., Phelps, R. G., Shanske, A., Totty, W. G., and Cohen, S. R. (2010) Buschke-ollendorff syndrome: absence of lemd3 mutation in an affected family. *Arch Dermatol* 146, 63-8, 10.1001/archdermatol.2009.320

24. Couto, A. R., Bruges-Armas, J., Peach, C. A., Chapman, K., Brown, M. A., Wordsworth, B. P., and Zhang, Y. (2007) A novel lemd3 mutation common to patients with osteopoikilosis with and without melorheostosis. *Calcif Tissue Int* 81, 81-4, 10.1007/s00223-007-9043-z 25. Pope, V., Dupuis, L., Kannu, P., Mendoza-Londono, R., Sajic, D., So, J., Yoon, G., and Lara-Corrales, I. (2016) Buschke-ollendorff syndrome: anovel case series and systematic review. *Br J Dermatol* 174, 723-9, 10.1111/bjd.14366

26. Gass, J. K., Hellemans, J., Mortier, G., Griffiths, M., and Burrows, N. P. (2008) Buschke-ollendorff syndrome: a manifestation of a heterozygous nonsense mutation in the lemd3 gene. *J Am Acad Dermatol* 58, S103-4, 10.1016/j.jaad.2007.03.031

27. Yuste-Chaves, M., Canueto, J., Santos-Briz, A., Ciria, S., Gonzalez-Sarmiento, R., and Una-muno, P. (2011) Buschke-ollendorff syndrome with striking phenotypic variation resulting from a novel c.2203c>t nonsense mutation in lemd3. *Pediatr Dermatol* 28,447-50, 10.1111/j.1525-1470.2010.01206.x 28. Burger, B., Hershkovitz, D., Indelman, M., Kovac, M., Galambos, J., Haeusermann, P., Sprecher, E., and Itin, P. H. (2010) Buschke-ollendorff syndrome in a three-generation family: influence of a novel lemd3 mutation to tropoelastin expression. *Eur J Dermatol* 20, 693-7, 10.1684/ejd.2010.1051

29. Korekawa, A., Nakano, H., Toyomaki, Y., Takiyoshi, N., Rokunohe, D., Akasaka, E., Nakajima, K., and Sawamura, D. (2012) Buschke-ollendorff syndrome associated with hypertrophic scar formation: a possible role for lemd3 mutation. *Br J Dermatol* 166, 900-3, 10.1111/j.1365-2133.2011.10691.x 30. Gutierrez, D., Cooper, K. D., Mitchell, A. L., and Cohn, H. I. (2015) Novel somatic mutation in lemd3 splice site results in buschke-ollendorff syndrome with polyostotic melorheostosis and osteopoikilosis. *Pediatr Dermatol* 32, e219-20, 10.1111/pde.12634

31. Kratzsch, J., Mitter, D., Ziemer, M., Kohlhase, J., and Voth, H. (2016) Identification of a novel point mutation in the lemd3 gene in an infant with buschke-ollendorff syndrome. *JAMA Dermatol* 152, 844-5, 10.1001/jamadermatol.2016.0350

32. Condorelli, A., Musso, N., Scuderi, L., Condorelli, D. F., Barresi, V., and De Pasquale, R. (2017) Juvenile elastoma without germline mutations in lemd3 gene: A case of buschke-ollendorff syndrome?. *Pediatr Dermatol* 34, e345-e346, 10.1111/pde.13287

33. Wu, W., Lin, F., and Worman, H. J. (2002) Intracellular trafficking of man1, an integral protein of the nuclear envelope inner membrane. *J Cell Sci* 115, 1361-71

34. Mansharamani, M. and Wilson, K. L. (2005) Direct binding of nuclear membrane protein man1 to emerin in vitro and two modes of binding to barrier-to-autointegration factor. *J Biol Chem* 280, 13863-70, 10.1074/jbc.M413020200

35. Liu, J., Lee, K. K., Segura-Totten, M., Neufeld, E., Wilson, K. L., and Gruenbaum, Y. (2003) Man1 and emerin have overlapping function(s) essential for chromosome segregation and cell division in *Caenorhabditis elegans*. *Proc. Natl. Acad. Sci. United States Am.* 100, 4598-4603, 10.1073/pnas.0730821100

36. Ostlund, C., Sullivan, T., Stewart, C. L., and Worman, H. J. (2006) Dependence of diffusional mobility of integral inner nuclear membrane proteins on α-type lamins. *Biochemistry* 45, 1374-1382, 10.1021/bi052156n 37. Wagner, N., Kagermeier, B., Loserth, S., and Krohne, G. (2006) The *Drosophila melanogaster* lem-domain protein man1. *Eur. J. Cell Biol.* 85, 91-105, https://doi.org/10.1016/j.ejcb.2005.10.002

38. Starr, D. A. and Han, M. (2002) Role of anc-1 in tethering nuclei to the actin cytoskeleton. *Science* 298, 406-9, 10.1126/science.1075119

39. Padmakumar, V. C., Libotte, T., Lu, W., Zaim, H., Abraham, S., Noegel, A. A., Gotzmann, J., Foisner, R., and Karakesisoglou, I. (2005) The inner nuclear membrane protein sun1 mediates the anchorage of nesprin-2 to the nuclear envelope. *J Cell Sci* 118, 3419-30, 10.1242/jcs.02471

40. Lombardi, M. L., Jaalouk, D. E., Shanahan, C. M., Burke, B., Roux, K. J., and Lammerding J. (2011) The interaction between nesprins and sun proteins at the nuclear envelope is criti-cal for force transmission between the nucleus and cytoskeleton. *J Biol Chem* 286, 26743-53, 10.1074/jbc.M111.233700

41. Caputo, S., Couprie, J., Duband-Goulet, I., Konde, E., Lin, F., Braud, S., Gondry, M., Gilquin, B., Worman, H. J., and Zinn-Justin, S. (2006) The carboxyl-terminal nucleoplasmic region ofman1 exhibits a dna binding winged helix domain. *J Biol Chem* 281, 18208-15, 10.1074/jbc.M601980200

42. Zurla, C., Jung, J., Blanchard, E. L., and Santangelo, P. J. (2017) in *Enhancer RNAs: Methods and Protocols* (Ørom, U. A., ed), pp. 155-170, Springer New York, N.Y., N.Y.

43. Booth, A. J., Hadley, R., Cornett, A. M., Dreffs, A. A., Matthes, S. A., Tsui, J. L., Weiss, K., Horowitz, J. C., Fiore, V. F., Barker, T. H., Moore, B. B., Martinez, F. J., Niklason, L. E., and White, E. S. (2012) Acellular normal and fibrotic human lung matrices as a culture system for in vitro investigation. *Am. J. Respir. Critical Care Medicine* 186, 866-876, 10.1164/rccm.201204-0754OC, PMID: 22936357

44. Harper, J. W., Hemmi, K., and Powers, J. C. (1985) Reaction of serine proteases with substituted isocoumarins: discovery of 3,4-dichloroisocoumarin, a new general mechanism based serine protease inhibitor. *Biochemistry* 24, 1831-1841, 10.1021/bi00329a005, PMID: 3893537

45. Collins, G. A. and Goldberg, A. L. (2017) The logic of the 26s proteasome. *Cell* 169, 792-806, https://doi.org/10.1016/j.cell.2017.04.023

46. Song, J., Tan, H., Perry, A. J., Akutsu, T., Webb, G. I., Whisstock, J. C., and Pike, R. N. (2012) Prosper: An integrated feature-based tool for predicting protease substrate cleavage sites. *PLOS ONE* 7, 1-23, 10.1371/journal.pone.0050300

47. Peter, M., Nakagawa, J., Dorée, M., Labbé, J., and Nigg, E. (1990) In vitro disassembly of the nuclear lamina and m phase-specific phosphorylation oflamins by cdc2 kinase. *Cell* 61, 591-602, https://doi.org/10.1016/0092-8674(90)90471-P 48. Hill, C. S. (2009) Nucleocytoplasmic shuttling of smad proteins. *Cell Res* 19, 36-46, 10.1038/cr.2008.325

49. Massague, J. (2012) Tgfbeta signalling in context. *Nat Rev Mol Cell Biol* 13, 616-30, 10.1038/nrm3434

50. Jones, M. G., Fletcher, S., and Richeldi, L. (2013) Idiopathic pulmonary fibrosis: recent trials and current drug therapy. *Respiration* 86, 353-63, 10.1159/000356958

51. Richeldi, L., du Bois, R. M., Raghu, G., Azuma, A., Brown, K. K., Costabel, U., Cottin, V., Flaherty, K. R., Hansell, D. M., Inoue, Y., Kim, D. S., Kolb, M., Nicholson, A. G., Noble, P. W., Selman, M., Taniguchi, H., Brun, M., Le Maulf F., Girard, M., Stowasser, S., Schlenker-Herceg, R., Disse, B., Collard, H. R., and Investigators, I. T. (2014) Efficacy and safety of nintedanib in idiopathic pulmonary fibrosis. *N Engl J Med* 370, 2071-82, 10.1056/NEJMoa1402584

52. Liu, F., Mih, J. D., Shea, B. S., Kho, A. T., Sharif A. S., Tager, A. M., and Tschumperlin, D. J. (2010) Feedback amplification of fibrosis through matrix stiffening and cox-2 suppression. *J Cell Biol* 190, 693-706, 10.1083/jcb.201004082

53. Liu, F., Lagares, D., Choi, K. M., Stopfer, L., Marinkovic, A., Vrbanac, V., Probst, C. K., Hiemer, S. E., Sisson, T. H., Horowitz, J. C., Rosas, L O., Fredenburgh, L. E., Feghali-Bostwick, C., Varelas, X., Tager, A. M., and Tschumperlin, D. J. (2015) Mechanosignaling through yap and taz drives fibroblast activation and fibrosis. *Am J Physiol Lung Cell Mol Physiol* 308, L344-57, 10.1152/ajplung.00300.2014

54. Wang, Y., Yella, J., Chen, J., McCormack, F. X., Madala, S. K., and Jegga, A. G. (2017) Unsu-pervised gene expression analyses identify ipf-severity correlated signatures, associated genes and biomarkers. *BMC Pulm Med* 17, 133, 10.1186/s12890-017-0472-9

55. DePianto, D. J., Chandriani, S., Abbas, A. R., Jia, G., N'Diaye, E. N., Caplazi, P., Kauder, S. E., Biswas, S., Karnik, S. K., Ha, C., Modrusan, Z., Matthay, M. A., Kukreja, J., Collard, H. R., Egen, J. G., Wolters, P. J., and Arron, J. R. (2015) Heterogeneous gene expression signatures correspond to distinct lung pathologies and biomarkers of disease severity in idiopathic pulmonary fibrosis. *Thorax* 70, 48-56, 10.1136/thoraxjnl-2013-204596

56. Nance, T., Smith, K. S., Anaya, V., Richardson, R., Ho, L., Pala, M., Mostafavi, S., Battle, A., Feghali-Bostwick, C., Rosen, G., and Montgomery, S. B. (2014) Transcriptome analysis reveals differential splicing events in ipf lung tissue. *PLOS ONE* 9, 1-15, 10.1371/jounal.pone.0092111

57. Lin, F., Blake, D. L., Callebaut, I., Skerjanc, I. S., Holmer, L., McBurney, M. W., Paulin-Levasseur, M., and Worman, H. J. Man1, an inner nuclear membrane protein that shares the lem domain with lamina-associated polypeptide 2 and emerin. *J. biological chemistry.* 275, 4840-4847

58. Kristensen, J. H., Karsdal, M. A., Sand, J. M. B., Willumsen, N., Diefenbach, C., Svensson, B., Hägglund, P., and Oersnes-Leeming, D. J. (2015) Serological assessment of neutrophil elastase activity on elastin during lung ecm remodeling. *BMC Pulm Med* 15, 10.1186/s12890-015-0048-5

59. Bühling, F., Röcken, C., Brasch, F., Hartig, R., Yasuda, Y., Saftig, P., Brömme, D., and Welte, T. (2004) Pivotal role of cathepsin k in lung fibrosis. *Am J Pathol* 164, 2203-16

60. Srivastava, M., Steinwede, K., Kiviranta, R., Morko, J., Hoymann, H. G., LUnger, F., Buhling, F., Welte, T., and Maus, U. A. (2008) Overexpression of cathepsin k in mice decreases collagen deposition and lung resistance in response to bleomycin-induced pulmonary fibrosis. *Respir Res* 9, 54, 10.1186/1465-9921-9-54

61. Fukuda, Y., Ishizaki, M., Kudoh, S., Kitaichi, M., and Yamanaka, N. (1998) Localization of matrix metalloproteinases-1, -2, and -9 and tissue inhibitor of metalloproteinase-2 in interstitial lung diseases. *Lab Invest* 78, 687-98

62. Radisky, D. C., Levy, D. D., Littlepage, L. E., Liu, H., Nelson, C. M., Fata, J. E., Leake, D., Godden, E. L., Albertson, D. G., Nieto, M. A., Werb, Z., and Bissell, M. J. (2005) Rac1b and reactive oxygen species mediate mmp-3-induced emt and genomic instability. *Nature* 436, 123-7, 10.1038/nature03688

63. Yamashita, C. M., Dolgonos, L., Zemans, R. L., Young, S. K., Robertson, J., Briones, N., Suzuki, T., Campbell, M. N., Gauldie, J., Radisky, D. C., Riches, D. W. H., Yu, G., Kaminski, N., McCulloch, C. A. G., and Downey, G. P. (2011) Matrix metalloproteinase 3 is a mediator of pulmonary fibrosis. *Am J Pathol* 179, 1733-45, 10.1016/j.ajpath.2011.06.041

64. García-Prieto, E., González-López, A., Cabrera, S., Astudillo, A., Gutiérrez-Fernández, A., Fanjul-Fernandez, M., Batalla-Solis, E., Puente, X. S., Fueyo, A., López-Otln, C., and Albaiceta, G. M. (2010) Resistance to bleomycin-induced lung fibrosis in mmp-8 deficient mice is mediated by interleukin-10. *PLoS One* 5, 10.1371/journal.pone.0013242

65. Zuo, F., Kaminski, N., Eugui, E., Allard, J., Yakhini, Z., Ben-Dor, A., Lollini, L., Morris, D., Kim, Y., DeLustro, B., Sheppard, D., Pardo, A., Selman, M., and Heller, R. A. (2002) Gene expression analysis reveals matrilysin as akey regulator of pulmonary fibrosis in mice and humans. *Proc Natl Acad Sci USA* 99, 6292-7, 10.1073/pnas.092134099
66. Kamaraju, A. K. and Roberts, A. B. (2005) Role of rho/rock and p38 map kinase pathways in transforming growth factor-beta-mediated smad-dependent growth inhibition of human breast carcinoma cells in vivo. *J Biol Chem* 280, 1024-36, 10.1074/jbc.M403960200
67. Varelas, X., Sakuma, R., Samavarchi-Tehrani, P., Peerani, R., Rao, B. M., Dembowy, J., Yaffe, M. B., Zandstra, P. W., and Wrana, J. L. (2008) Taz controls smad nucleocytoplasmic shuttling and regulates human embryonic stem-cell self-renewal. *Nat Cell Biol* 10, 837-48, 10.1038/ncb1748
68. Samarakoon, R., Higgins, S. P., Higgins, C. E., and Higgins, P. J. (2008) Tgf-beta1-induced plasminogen activator inhibitor-1 expression in vascular smooth muscle cells re-quires pp60(c-src)/egfr(y845) and rho/rock signaling. *J Mol Cell Cardiol* 44, 527-38, 10.1016/j.yjmcc.2007.12.006
69. Grannas, K., Arngarden, L., Lonn, P., Mazurkiewicz, M., Blokzijl, A., Zieba, A., and Soderberg, O. (2015) Crosstalk between hippo and tgfbeta: Subcellular localization of yap/taz/smad complexes. *J Mol Biol* 427, 3407-15, 10.1016/j.jmb.2015.04.015
70. Beyer, T. A., Weiss, A., Khomchuk, Y., Huang, K., Ogunjimi, A. A., Varelas, X., and Wrana, L. (2013) Switch enhancers interpret tgf-beta and hippo signaling to control cell fate in human embryonic stem cells. *Cell Rep* 5, 1611-24, 10.1016/j.celrep.2013.11.021
71. Landrum, M. J., Lee, J. M., Benson, M., Brown, G., Chao, C., Chitipiralla, S., Gu, B., Hart, J., Hoffman, D., Hoover, J., Jang, W., Katz, K., Ovetsky, M., Riley, G., Sethi, A., Tully, R., Villamarin-Salomon, R., Rubinstein, W., and Maglott, D. R. (2016) Clinvar: public archive of interpretations of clinically relevant variants. *Nucleic Acids Res* 44, D862-8, 10.1093/nar/gkv1222
72. Rajgor, D., Mellad, J. A., Autore, F., Zhang, Q., and Shanahan, C. M. (2012) Multiple novel nesprin-1 and nesprin-2 variants act as versatile tissue-specific intracellular scaffolds. *PLoS One* 7, e40098, 10.1371/journal.pone.0040098
73. Santos, M., Domingues, S. C., Costa, P., Muller, T., Galozzi, S., Marcus, K., da Cruz e Silva, E. F., da Cruz e Silva, O. A., and Rebelo, S. (2014) Identification of a novel human lap1 isoform that is regulated by protein phosphorylation. *PLoS One* 9, e113732, 10.1371/journal.pone.0113732
74. Abascal, F., Tress, M. L., and Valencia, A. (2015) Alternative splicing and co-option of transposable elements: the case of tmpo/lap2alpha and znf451 in mammals. *Bioinformatics* 31, 2257-61, 10.1093/bioinformatics/btv132
75. Zhang, W., Bai, T., Zhang, S., Xu, S., Chen, H., and Li, C. (2017) Isoforms of the nuclear envelope protein nurim are differentially expressed during heart development in mice. *Gene* 627, 123-128, 10.1016/j.gene.2017.06.009
76. Zhang, Q., Skepper, J. N., Yang, F., Davies, J. D., Hegyi, L., Roberts, R. G., Weissberg, P. L., Ellis, A., and Shanahan, C. M. (2001) Nesprins: a novel family of spectrin-repeat-containing proteins that localize to the nuclear membrane in multiple tissues. *J Cell Sci* 114, 4485-98
77. Holt, L, Duong, N. T., Zhang, Q., Lam le, T., Sewry, C. A., Mamchaoui, K., Shanahan, C. M., and Morris, G. E. (2016) Specific localization of nesprin-1-alpha2, the short isoform of nesprin-1 with a kash domain, in developing, fetal and regenerating muscle, using a new monoclonal antibody. *BMC Cell Biol* 17, 26, 10.1186/s12860-016-0105-9
78. Kobayashi, Y., Katanosaka, Y., Iwata, Y., Matsuoka, M., Shigekawa, M., and Wakabayashi, S. (2006) Identification and characterization of gsrp-56, a novel golgi-localized spectrin repeat-containing protein. *Exp Cell Res* 312, 3152-64, 10.1016/j.yexcr.2006.06.026
79. Rajgor, D., Mellad, J. A., Soong, D., Rattner, J. B., Fritzler, M. J., and Shanahan, C. M. (2014) Mammalian microtubule p-body dynamics are mediated by nesprin-1. *J Cell Biol* 205, 457-75, 10.1083/jcb.201306076
80. Rajgor, D., Hanley, J. G., and Shanahan, C. M. (2016) Identification of novel nesprin-1 bind-ing partners and cytoplasmic matrin-3 in processing bodies. *Mol Biol Cell* 27, 3894-3902, 10.1091/mbc.E16-06-0346
81. Ruijter, J. M., Lorenz, P., Tuomi, J. M., Hecker, M., and van den Hoff, M. J. B. (2014) Fluorescent-increase kinetics of different fluorescent reporters used for qpcr depend on monitoring chem-istry, targeted sequence, type of dna input and pcr efficiency. *Mikrochim Acta* 181, 1689-96, 10.1007/s00604-013-1155-8
82. Rinker, T. E., Philbrick, B. D., Hettiaratchi, M. H., Smalley, D. M., McDevitt, T. C., and Temenoff S. (2017) Microparticle-mediated sequestration of cell-secreted proteins to modulate chondro-cytic differentiation. *Acta Biomater,* 10.1016/j.actbio.2017.12.038
83. Rho, H.-W., Lee, B.-C., Choi, E.-S., Choi, I.-J., Lee, Y.-S., and Goh, S.-H. (2010) Identification of valid reference genes for gene expression studies of human stomach cancer by reverse transcription-qpcr. *BMC Cancer* 10, 240.
84. Gardinassi, L. G., Garcia, G. R., Costa, C. H. N., Costa Silva, V., and de Miranda Santos, I. K. F. (2016) Blood transcriptional profiling reveals immunological signatures of distinct states of infection of humans with *Leishmania infantum*. *PLOS Neglected Trop. Dis.* 10, 1-24.

While the presently disclosed subject matter has been disclosed with reference to specific embodiments, it is apparent that other embodiments and variations of this presently disclosed subject matter may be devised by others skilled in the art without departing from the true spirit and scope of the presently disclosed subject matter.

What is claimed is:

1. A composition comprising a substance capable of modulating activity of LEMD3 in a vertebrate subject, wherein the substance is selected from the group consisting of:
   (a) an isolated LEMD3 polypeptide comprising an amino acid sequence of SEQ ID NO: 25;
   (b) an effective amount of an isolated siRNA that modulates expression of a LEMD3-encoding nucleic acid molecule, a vector encoding a siRNA that modulates expression of a LEMD3-encoding nucleic acid molecule, or combinations thereof, wherein the LEMD3-encoding nucleic acid molecule encodes a LEMD3 polypeptide comprising an amino acid sequence of SEQ ID NO: 25; and
   (c) a vector comprising a nucleic acid sequence encoding a LEMD3 polypeptide operatively linked to a promoter, wherein the LEMD3 polypeptide comprises an amino acid sequence of SEQ ID NO: 25.

2. The composition of claim 1, wherein the LEMD3 polypeptide comprises a polypeptide selected from the group consisting of a polypeptide having an amino acid sequence having 95% homology to SEQ ID NO:25 and a fragment thereof.

3. The composition of claim 2, wherein the LEMD3 polypeptide is encoded by a nucleic acid sequence is selected from the group consisting of:
   (a) a nucleic acid sequence encoding a polypeptide comprising an amino acid sequence as set forth in SEQ ID NO: 25, a fragment thereof, a polypeptide having an amino acid sequence having 95% homology to SEQ ID: 25, and a fragment thereof;
   (b) a nucleic acid sequence as set forth in SEQ ID NO: 27 or its complementary strands;
   (c) a nucleic acid sequence having 95% homology to a nucleic acid sequence as set forth in SEQ ID NO: 27, and which encodes a LEMD3 polypeptide; and
   (d) a nucleic acid sequence differing from a nucleic acid molecule of (a), (b), or (c) above due to degeneracy of the genetic code, and which encodes a LEMD3 polypeptide encoded by the nucleic acid molecule of (a), (b), or (c) above.

4. The composition of claim 3, wherein the amino acid sequence comprises at least one modification selected from the group consisting of an amino acid deletion, an amino acid addition, an amino acid substitution, and combinations thereof.

5. The composition of claim 1, wherein the vector encoding the siRNA comprises: a promoter operatively linked to a nucleic acid molecule encoding the siRNA molecule; and a transcription termination sequence.

6. The composition of claim 1, comprising a pharmaceutically acceptable diluent or vehicle.

7. A kit comprising the composition of claim 1 and at least one reagent and/or device for introducing the composition into a cell, tissue, and/or subject.

8. The kit of claim 7, further comprising instructions for introducing the composition in a cell, tissue, or subject.

* * * * *

SEQUENCE LISTING

<160> NUMBER OF SEQ ID NOS: 29

<210> SEQ ID NO 1
<211> LENGTH: 19
<212> TYPE: RNA
<213> ORGANISM: Homo sapiens

<400> SEQUENCE: 1

-continued

```
ggauagagcu guugacuuc                                                   19

<210> SEQ ID NO 2
<211> LENGTH: 19
<212> TYPE: RNA
<213> ORGANISM: Homo sapiens

<400> SEQUENCE: 2
gaacuucucc agcaauuua                                                   19

<210> SEQ ID NO 3
<211> LENGTH: 19
<212> TYPE: RNA
<213> ORGANISM: Homo sapiens

<400> SEQUENCE: 3
ggaauaaggu guguugguu                                                   19

<210> SEQ ID NO 4
<211> LENGTH: 19
<212> TYPE: RNA
<213> ORGANISM: Homo sapiens

<400> SEQUENCE: 4
caaggcagau guaugauau                                                   19

<210> SEQ ID NO 5
<211> LENGTH: 21
<212> TYPE: RNA
<213> ORGANISM: Homo sapiens

<400> SEQUENCE: 5
caagcugacc cugaaguucu u                                                21

<210> SEQ ID NO 6
<211> LENGTH: 39
<212> TYPE: DNA
<213> ORGANISM: Homo sapiens

<400> SEQUENCE: 6
ctgctgggcc tggatagcac ctgaaaagct cgagctcga                             39

<210> SEQ ID NO 7
<211> LENGTH: 41
<212> TYPE: DNA
<213> ORGANISM: Homo sapiens

<400> SEQUENCE: 7
cgggttcgga atcggtttgc cggaacttcc ttgagaattg g                          41

<210> SEQ ID NO 8
<211> LENGTH: 32
<212> TYPE: DNA
<213> ORGANISM: Homo sapiens

<400> SEQUENCE: 8
ttaaatggat ccccgccacc atggcggcgg ca                                    32

<210> SEQ ID NO 9
<211> LENGTH: 31
<212> TYPE: DNA
<213> ORGANISM: Homo sapiens
```

```
<400> SEQUENCE: 9
tgctcaccat tcgatatttc atgtaacgca g                              31

<210> SEQ ID NO 10
<211> LENGTH: 28
<212> TYPE: DNA
<213> ORGANISM: Homo sapiens

<400> SEQUENCE: 10
gaaatatcga atggtgagca agggcgag                                  28

<210> SEQ ID NO 11
<211> LENGTH: 18
<212> TYPE: DNA
<213> ORGANISM: Homo sapiens

<400> SEQUENCE: 11
atccttgcgg ccgctcac                                             18

<210> SEQ ID NO 12
<211> LENGTH: 22
<212> TYPE: DNA
<213> ORGANISM: Homo sapiens

<400> SEQUENCE: 12
ctggagactt cagttcaggg ag                                        22

<210> SEQ ID NO 13
<211> LENGTH: 18
<212> TYPE: DNA
<213> ORGANISM: Homo sapiens

<400> SEQUENCE: 13
tctgctggag gccacgtc                                             18

<210> SEQ ID NO 14
<211> LENGTH: 20
<212> TYPE: DNA
<213> ORGANISM: Homo sapiens

<400> SEQUENCE: 14
tttgttactg taactcacag                                           20

<210> SEQ ID NO 15
<211> LENGTH: 21
<212> TYPE: DNA
<213> ORGANISM: Homo sapiens

<400> SEQUENCE: 15
ttgaacagaa agcgttcttt g                                         21

<210> SEQ ID NO 16
<211> LENGTH: 20
<212> TYPE: DNA
<213> ORGANISM: Homo sapiens

<400> SEQUENCE: 16
ctgcgttaca tgaaatatcg                                           20

<210> SEQ ID NO 17
<211> LENGTH: 19
<212> TYPE: DNA
<213> ORGANISM: Homo sapiens
```

-continued

```
<400> SEQUENCE: 17
tttctcgtcc gaattcctg                                                   19

<210> SEQ ID NO 18
<211> LENGTH: 22
<212> TYPE: DNA
<213> ORGANISM: Homo sapiens

<400> SEQUENCE: 18
tttcgacgtg cttttgttac tg                                               22

<210> SEQ ID NO 19
<211> LENGTH: 23
<212> TYPE: DNA
<213> ORGANISM: Homo sapiens

<400> SEQUENCE: 19
tgtttcctcc tcttcttttg tcc                                              23

<210> SEQ ID NO 20
<211> LENGTH: 20
<212> TYPE: DNA
<213> ORGANISM: Homo sapiens

<400> SEQUENCE: 20
gtaacccgtt gaaccccatt                                                  20

<210> SEQ ID NO 21
<211> LENGTH: 20
<212> TYPE: DNA
<213> ORGANISM: Homo sapiens

<400> SEQUENCE: 21
ccatccaatc ggtagtagcg                                                  20

<210> SEQ ID NO 22
<211> LENGTH: 17
<212> TYPE: DNA
<213> ORGANISM: Homo sapiens

<400> SEQUENCE: 22
aggcaccagg gcgtgat                                                     17

<210> SEQ ID NO 23
<211> LENGTH: 23
<212> TYPE: DNA
<213> ORGANISM: Homo sapiens

<400> SEQUENCE: 23
gcccacatag gaatccttct gac                                              23

<210> SEQ ID NO 24
<211> LENGTH: 911
<212> TYPE: PRT
<213> ORGANISM: Homo sapiens

<400> SEQUENCE: 24

Met Ala Ala Ala Ala Ala Ser Ala Pro Gln Gln Leu Ser Asp Glu Glu
1               5                   10                  15

Leu Phe Ser Gln Leu Arg Arg Tyr Gly Leu Ser Pro Gly Pro Val Thr
            20                  25                  30
```

```
Glu Ser Thr Arg Pro Val Tyr Leu Lys Lys Leu Lys Lys Leu Arg Glu
         35                  40                  45

Glu Glu Gln Gln Gln His Arg Ser Gly Gly Arg Gly Asn Lys Thr Arg
 50                      55                  60

Asn Ser Asn Asn Asn Thr Ala Ala Ala Thr Val Ala Ala Ala Gly
 65                  70                  75                  80

Pro Ala Ala Ala Ala Ala Gly Met Gly Val Arg Pro Val Ser Gly
                 85              90                  95

Asp Leu Ser Tyr Leu Arg Thr Pro Gly Gly Leu Cys Arg Ile Ser Ala
             100                 105                 110

Ser Gly Pro Glu Ser Leu Leu Gly Gly Pro Gly Gly Ala Ser Ala Ala
             115                 120                 125

Pro Ala Ala Gly Ser Lys Val Leu Leu Gly Phe Ser Ser Asp Glu Ser
    130                 135                 140

Asp Val Glu Ala Ser Pro Arg Asp Gln Ala Gly Gly Gly Arg Lys
145                 150                 155                 160

Asp Arg Ala Ser Leu Gln Tyr Arg Gly Leu Lys Ala Pro Pro Ala Pro
                165                 170                 175

Leu Ala Ala Ser Glu Val Thr Asn Ser Asn Ser Ala Glu Arg Arg Lys
            180                 185                 190

Pro His Ser Trp Trp Gly Ala Arg Arg Pro Ala Gly Pro Glu Leu Gln
            195                 200                 205

Thr Pro Pro Gly Lys Asp Gly Ala Val Glu Asp Glu Gly Glu Gly
    210                 215                 220

Glu Asp Gly Glu Glu Arg Asp Pro Glu Thr Glu Glu Pro Leu Trp Ala
225                 230                 235                 240

Ser Arg Thr Val Asn Gly Ser Arg Leu Val Pro Tyr Ser Cys Arg Glu
                245                 250                 255

Asn Tyr Ser Asp Ser Glu Glu Glu Asp Asp Asp Val Ala Ser Ser
            260                 265                 270

Arg Gln Val Leu Lys Asp Asp Ser Leu Ser Arg His Arg Pro Arg Arg
            275                 280                 285

Thr His Ser Lys Pro Leu Pro Pro Leu Thr Ala Lys Ser Ala Gly Gly
    290                 295                 300

Arg Leu Glu Thr Ser Val Gln Gly Gly Gly Leu Ala Met Asn Asp
305                 310                 315                 320

Arg Ala Ala Ala Gly Ser Leu Asp Arg Ser Arg Asn Leu Glu Glu
                325                 330                 335

Ala Ala Ala Ala Glu Gln Gly Gly Gly Cys Asp Gln Val Asp Ser Ser
            340                 345                 350

Pro Val Pro Arg Tyr Arg Val Asn Ala Lys Lys Leu Thr Pro Leu Leu
    355                 360                 365

Pro Pro Pro Leu Thr Asp Met Asp Ser Thr Leu Asp Ser Ser Thr Gly
    370                 375                 380

Ser Leu Leu Lys Thr Asn Asn His Ile Gly Gly Gly Ala Phe Ser Val
385                 390                 395                 400

Asp Ser Pro Arg Ile Tyr Ser Asn Ser Leu Pro Pro Ser Ala Ala Val
                405                 410                 415

Ala Ala Ser Ser Ser Leu Arg Ile Asn His Ala Asn His Thr Gly Ser
            420                 425                 430

Asn His Thr Tyr Leu Lys Asn Thr Tyr Asn Lys Pro Lys Leu Ser Glu
            435                 440                 445

Pro Glu Glu Glu Leu Leu Gln Gln Phe Lys Arg Glu Glu Val Ser Pro
```

-continued

```
            450                 455                 460
Thr Gly Ser Phe Ser Ala His Tyr Leu Ser Met Phe Leu Leu Thr Ala
465                 470                 475                 480

Ala Cys Leu Phe Phe Leu Ile Leu Gly Leu Thr Tyr Leu Gly Met Arg
                485                 490                 495

Gly Thr Gly Val Ser Glu Asp Gly Glu Leu Ser Ile Glu Asn Pro Phe
                500                 505                 510

Gly Glu Thr Phe Gly Lys Ile Gln Glu Ser Glu Lys Thr Leu Met Met
                515                 520                 525

Asn Thr Leu Tyr Lys Leu His Asp Arg Leu Ala Gln Leu Ala Gly Asp
            530                 535                 540

His Glu Cys Gly Ser Ser Ser Gln Arg Thr Leu Ser Val Gln Glu Ala
545                 550                 555                 560

Ala Ala Tyr Leu Lys Asp Leu Gly Pro Glu Tyr Glu Gly Ile Phe Asn
                565                 570                 575

Thr Ser Leu Gln Trp Ile Leu Glu Asn Gly Lys Asp Val Gly Ile Arg
                580                 585                 590

Cys Val Gly Phe Gly Pro Glu Glu Leu Thr Asn Ile Thr Asp Val
                595                 600                 605

Gln Phe Leu Gln Ser Thr Arg Pro Leu Met Ser Phe Trp Cys Arg Phe
610                 615                 620

Arg Arg Ala Phe Val Thr Val Thr His Arg Leu Leu Leu Cys Leu
625                 630                 635                 640

Gly Val Val Met Val Cys Val Val Leu Arg Tyr Met Lys Tyr Arg Trp
                645                 650                 655

Thr Lys Glu Glu Glu Thr Arg Gln Met Tyr Asp Met Val Val Lys
                660                 665                 670

Ile Ile Asp Val Leu Arg Ser His Asn Glu Ala Cys Gln Glu Asn Lys
            675                 680                 685

Asp Leu Gln Pro Tyr Met Pro Ile Pro His Val Arg Asp Ser Leu Ile
            690                 695                 700

Gln Pro His Asp Arg Lys Lys Met Lys Lys Val Trp Asp Arg Ala Val
705                 710                 715                 720

Asp Phe Leu Ala Ala Asn Glu Ser Arg Val Arg Thr Glu Thr Arg Arg
                725                 730                 735

Ile Gly Gly Ala Asp Phe Leu Val Trp Arg Trp Ile Gln Pro Ser Ala
                740                 745                 750

Ser Cys Asp Lys Ile Leu Val Ile Pro Ser Lys Val Trp Gln Gly Gln
                755                 760                 765

Ala Phe His Leu Asp Arg Arg Asn Ser Pro Pro Asn Ser Leu Thr Pro
                770                 775                 780

Cys Leu Lys Ile Arg Asn Met Phe Asp Pro Val Met Glu Ile Gly Asp
785                 790                 795                 800

Gln Trp His Leu Ala Ile Gln Glu Ala Ile Leu Glu Lys Cys Ser Asp
                805                 810                 815

Asn Asp Gly Ile Val His Ile Ala Val Asp Lys Asn Ser Arg Glu Gly
                820                 825                 830

Cys Val Tyr Val Lys Cys Leu Ser Pro Glu Tyr Ala Gly Lys Ala Phe
                835                 840                 845

Lys Ala Leu His Gly Ser Trp Phe Asp Gly Lys Leu Val Thr Val Lys
                850                 855                 860

Tyr Leu Arg Leu Asp Arg Tyr His His Arg Phe Pro Gln Ala Leu Thr
865                 870                 875                 880
```

Ser Asn Thr Pro Leu Lys Pro Ser Asn Lys His Met Asn Ser Met Ser
            885                 890                 895

His Leu Arg Leu Arg Thr Gly Leu Thr Asn Ser Gln Gly Ser Ser
        900                 905                 910

<210> SEQ ID NO 25
<211> LENGTH: 232
<212> TYPE: PRT
<213> ORGANISM: Homo sapiens

<400> SEQUENCE: 25

Met Ala Ala Ala Ala Ser Ala Pro Gln Gln Leu Ser Asp Glu Glu
1               5                   10                  15

Leu Phe Ser Gln Arg Asp Ser Leu Ile Gln Pro His Asp Arg Lys Lys
            20                  25                  30

Met Lys Lys Val Trp Asp Arg Ala Val Asp Phe Leu Ala Ala Asn Glu
        35                  40                  45

Ser Arg Val Arg Thr Glu Thr Arg Arg Ile Gly Gly Ala Asp Phe Leu
    50                  55                  60

Val Trp Arg Trp Ile Gln Pro Ser Ala Ser Cys Asp Lys Ile Leu Val
65                  70                  75                  80

Ile Pro Ser Lys Val Trp Gln Gly Gln Ala Phe His Leu Asp Arg Arg
                85                  90                  95

Asn Ser Pro Pro Asn Ser Leu Thr Pro Cys Leu Lys Ile Arg Asn Met
            100                 105                 110

Phe Asp Pro Val Met Glu Ile Gly Asp Gln Trp His Leu Ala Ile Gln
        115                 120                 125

Glu Ala Ile Leu Glu Lys Cys Ser Asp Asn Asp Gly Ile Val His Ile
    130                 135                 140

Ala Val Asp Lys Asn Ser Arg Glu Gly Cys Val Tyr Val Lys Cys Leu
145                 150                 155                 160

Ser Pro Glu Tyr Ala Gly Lys Ala Phe Lys Ala Leu His Gly Ser Trp
                165                 170                 175

Phe Asp Gly Lys Leu Val Thr Val Lys Tyr Leu Arg Leu Asp Arg Tyr
            180                 185                 190

His His Arg Phe Pro Gln Ala Leu Thr Ser Asn Thr Pro Leu Lys Pro
        195                 200                 205

Ser Asn Lys His Met Asn Ser Met Ser His Leu Arg Leu Arg Thr Gly
    210                 215                 220

Leu Thr Asn Ser Gln Gly Ser Ser
225                 230

<210> SEQ ID NO 26
<211> LENGTH: 2733
<212> TYPE: DNA
<213> ORGANISM: Homo sapiens

<400> SEQUENCE: 26
atggcggcgg cagcagcttc ggcgcctcag cagctctcgg atgaggagct tttctctcag     60
ctccgccgtt acggcctgtc tcccggacca gtgacggaga gcaccgccc ggtctacctc    120 aagaagctga agaagcttcg agaggaagag cagcaacagc accggtcagg gggccgcggc    180
aacaagacgc ggaacagtaa taacaataac acggcagccg ccacggtcgc agccgcggga    240
ccagcggcgc cggcggccgc ggggatgggg gtccggccgg tctcgggcga cctctcctac    300
ttacggactc ctggggggct gtgccgaatc tcggcctctg gcccagagag cctcctggga    360

| | |
|---|---|
| gggcccgggg gcgcctccgc cgcccccgcg gctggcagca aagtgctgct gggcttcagc | 420 |
| tcggacgagt cggacgtgga ggccagtccc cgggaccagg ccggcggcgg cgggaggaaa | 480 |
| gaccgggctt cgctccagta ccgcgggctc aaagcgccgc cggcgcccct ggccgccagc | 540 |
| gaggtgacta acagcaactc tgcagagcga aggaagcccc actcgtggtg gggggccagg | 600 |
| aggccggcgg gccccgagct gcagaccccg ccggggaaag atggagcagt ggaggacgag | 660 |
| gaagggggag gagaggacgg tgaggagagg gaccccgaga ccgaggagcc gctctgggcg | 720 |
| agccggaccg tgaatggcag ccggcttgtc ccctacagct gccgggaaaa ctattcggac | 780 |
| tcagaggaag aggacgacga cgacgtggcc tccagcagac aggtattaaa ggacgactcc | 840 |
| ctttcccggc atcggcccag acgaacccat agtaagcctc tcccccgct gactgctaaa | 900 |
| tcggccggcg gcaggctgga gacttcagtt caggagggg gaggactcgc gatgaatgac | 960 |
| agggcggcgg ctgccgggag tctagacagg agccgaaacc tcgaagaggc ggcggccgcg | 1020 |
| gagcagggag gagggtgtga tcaagtggac tccagccccg ttcctagata ccgtgttaac | 1080 |
| gctaagaaac tgacccctct cctgcccccg ccacttactg acatggactc aaccttggat | 1140 |
| tcgtcaacag gctcccttct gaaaaccaat aatcatattg gcggtggggc cttcagtgtg | 1200 |
| gactccccca ggatttattc taacagtctc cctcccagtg cggcggtggc cgcctctagt | 1260 |
| tcactcagga tcaatcacgc caatcatacg ggctccaatc ataccacct gaaaaacaca | 1320 |
| tacaacaaac cgaagctttc cgaacccgaa gaggaacttc tccagcaatt taaacgggag | 1380 |
| gaggtgtccc caacagggag tttcagtgcc cactacttgt cgatgtttct cttaactgct | 1440 |
| gcctgcttat ttttcctaat actgggactg acttacctag aatgagagg gacaggagta | 1500 |
| tctgaggatg gagaactcag catagaaaac cccttggtg aaacatttgg aaaaatacaa | 1560 |
| gaaagtgaaa aaactcttat gatgaacaca ttatataagc ttcatgatcg attggcacag | 1620 |
| cttgcaggag atcatgaatg tggcagttct agtcaaagaa cgctttctgt tcaagaggca | 1680 |
| gctgcgtatt taaaagattt aggtcctgaa tatgaaggta tatttaacac ttcattgcag | 1740 |
| tggatcttag aaaatggaaa agatgttgga ataaggtgtg ttggttttgg ccctgaggaa | 1800 |
| gaattgacaa atataactga tgtgcagttt ttacagtcca caagaccact gatgtctttt | 1860 |
| tggtgtcgtt ttcgacgtgc ttttgttact gtaactcaca gattattgtt gttatgctta | 1920 |
| ggtgtagtga tggtttgtgt cgttctgcgt tacatgaaat atcgatggac aaaagaagag | 1980 |
| gaggaaacaa ggcagatgta tgatatggtg gtaaagatta tagatgtttt acgaagtcat | 2040 |
| aatgaagcct gccaggaaaa caagatttta caaccttaca tgcctattcc acatgtacgc | 2100 |
| gattccttaa tacagcctca tgacaggaaa aaatgaaga agtctgggat agagctgtt | 2160 |
| gacttccttg ctgctaatga gtctagagtt cgcacgaaaa cacgaagaat aggtggtgca | 2220 |
| gattttctgg tttggcggtg gatccagcct tctgcatcct gtgacaaaat attagttata | 2280 |
| ccttctaaag tatggcaagg tcaagcattt catttagata gaagaaattc accaccaaat | 2340 |
| agtttgacac cgtgtctaaa gattcggaat atgtttgatc ccgttatgga aatagggat | 2400 |
| cagtggcatt tggcaattca agaagcaatt ttagaaaaat gcagtgataa tgatggcatt | 2460 |
| gttcacattg cagtagacaa aaattcacgt gagggttgtg tatatgttaa atgtctgtct | 2520 |
| ccagaatatg ctggaaaggc ttttaaagca ttgcatggct cttggtttga tgggaaattg | 2580 |
| gttacagtaa atatttacg actagataga taccaccatc gctttcccca ggctctcact | 2640 |
| tccaacactc cattgaagcc atcaaataaa catatgaact ccatgtctca tcttcgtctt | 2700 |

```
cggactggcc taaccaattc tcaaggaagt tcc                                   2733
```

<210> SEQ ID NO 27
<211> LENGTH: 696
<212> TYPE: DNA
<213> ORGANISM: Homo sapiens

<400> SEQUENCE: 27

```
atggcggcgg cagcagcttc ggcgcctcag cagctctcgg atgaggagct tttctctcag       60
cgcgattcct taatacagcc tcatgacagg aaaaaaatga agaaagtctg ggatagagct      120
gttgacttcc ttgctgctaa tgagtctaga gttcgcacgg aaacacgaag aataggtggt      180
gcagattttc tggtttggcg gtggatccag ccttctgcat cctgtgacaa atattagtt      240
ataccttcta agtatggcaa ggtcaagca tttcatttag atagaagaaa ttcaccacca       300
aatagtttga caccgtgtct aaagattcgg aatatgtttg atcccgttat ggaaataggg      360
gatcagtggc atttggcaat tcaagaagca attttagaaa atgcagtga taatgatggc       420
attgttcaca ttgcagtaga caaaaattca cgtgagggtt gtgtatatgt taaatgtctg      480
tctccagaat atgctggaaa ggcttttaaa gcattgcatg gctcttggtt tgatgggaaa      540
ttggttacag taaaatattt acgactagat agataccacc atcgctttcc ccaggctctc      600
acttccaaca ctccattgaa gccatcaaat aaacatatga actccatgtc tcatcttcgt      660
cttcggactg gcctaaccaa ttctcaagga agttcc                                696
```

<210> SEQ ID NO 28
<211> LENGTH: 639
<212> TYPE: DNA
<213> ORGANISM: Homo sapiens

<400> SEQUENCE: 28

```
gtacgcgatt ccttaataca gcctcatgac aggaaaaaaa tgaagaaagt ctgggataga       60
gctgttgact tccttgctgc taatgagtct agagttcgca cggaaacacg aagaataggt      120
ggtgcagatt ttctggtttg gcggtggatc cagccttctg catcctgtga caaaatatta      180
gttataccct tctaaagtatg gcaaggtcaa gcatttcatt tagatagaag aaattcacca      240
ccaaatagtt tgacaccgtg tctaaagatt cggaatatgt ttgatcccgt tatggaaata      300
ggggatcagt ggcatttggc aattcaagaa gcaattttag aaaaatgcag tgataatgat      360
ggcattgttc acattgcagt agacaaaaat tcacgtgagg gttgtgtata tgttaaatgt      420
ctgtctccag aatatgctgg aaaggctttt aaagcattgc atggctcttg gtttgatggg      480
aaattggtta cagtaaaata tttacgacta gatagatacc accatcgctt tccccaggct      540
ctcacttcca acactccatt gaagccatca aataaacata tgaactccat gtctcatctt      600
cgtcttcgga ctggcctaac caattctcaa ggaagttcc                             639
```

<210> SEQ ID NO 29
<211> LENGTH: 213
<212> TYPE: PRT
<213> ORGANISM: Homo sapiens

<400> SEQUENCE: 29

```
Val Arg Asp Ser Leu Ile Gln Pro His Asp Arg Lys Lys Met Lys Lys
1               5                   10                  15

Val Trp Asp Arg Ala Val Asp Phe Leu Ala Ala Asn Glu Ser Arg Val
            20                  25                  30

Arg Thr Glu Thr Arg Arg Ile Gly Gly Ala Asp Phe Leu Val Trp Arg
```

```
                    35                  40                  45
Trp Ile Gln Pro Ser Ala Ser Cys Asp Lys Ile Leu Val Ile Pro Ser
    50                  55                  60

Lys Val Trp Gln Gly Gln Ala Phe His Leu Asp Arg Arg Asn Ser Pro
65                  70                  75                  80

Pro Asn Ser Leu Thr Pro Cys Leu Lys Ile Arg Asn Met Phe Asp Pro
                85                  90                  95

Val Met Glu Ile Gly Asp Gln Trp His Leu Ala Ile Gln Glu Ala Ile
                100                 105                 110

Leu Glu Lys Cys Ser Asp Asn Asp Gly Ile Val His Ile Ala Val Asp
            115                 120                 125

Lys Asn Ser Arg Glu Gly Cys Val Tyr Val Lys Cys Leu Ser Pro Glu
            130                 135                 140

Tyr Ala Gly Lys Ala Phe Lys Ala Leu His Gly Ser Trp Phe Asp Gly
145                 150                 155                 160

Lys Leu Val Thr Val Lys Tyr Leu Arg Leu Asp Arg Tyr His His Arg
                165                 170                 175

Phe Pro Gln Ala Leu Thr Ser Asn Thr Pro Leu Lys Pro Ser Asn Lys
            180                 185                 190

His Met Asn Ser Met Ser His Leu Arg Leu Arg Thr Gly Leu Thr Asn
        195                 200                 205

Ser Gln Gly Ser Ser
    210
```